(12) United States Patent
Ashley et al.

(10) Patent No.: US 8,703,907 B2
(45) Date of Patent: Apr. 22, 2014

(54) CONTROLLED DRUG RELEASE FROM DENDRIMERS

(75) Inventors: Gary Ashley, Alameda, CA (US); Daniel V. Santi, San Francisco, CA (US)

(73) Assignee: Prolynx LLC, San Francisco, CA (US)

( * ) Notice: Subject to any disclaimer, the term of this patent is extended or adjusted under 35 U.S.C. 154(b) by 0 days.

(21) Appl. No.: 13/696,301

(22) PCT Filed: May 5, 2011

(86) PCT No.: PCT/US2011/035403
§ 371 (c)(1), (2), (4) Date: Jan. 28, 2013

(87) PCT Pub. No.: WO2011/140376
PCT Pub. Date: Nov. 10, 2011

(65) Prior Publication Data
US 2013/0123461 A1    May 16, 2013

Related U.S. Application Data

(60) Provisional application No. 61/331,749, filed on May 5, 2010.

(51) Int. Cl.
*A61K 38/26* (2006.01)
*A61K 38/28* (2006.01)
*C07K 5/00* (2006.01)
*C07K 7/00* (2006.01)
*C07K 16/00* (2006.01)
*C07K 17/00* (2006.01)
*A61K 38/00* (2006.01)
*A61K 38/04* (2006.01)

(52) U.S. Cl.
USPC .......................... 530/308; 530/323; 530/329

(58) Field of Classification Search
None
See application file for complete search history.

(56) References Cited

U.S. PATENT DOCUMENTS

| 7,585,837 | B2 | 9/2009 | Shechter et al. |
| 2008/0206183 | A1 | 8/2008 | Commeyras et al. |
| 2010/0003316 | A1 | 1/2010 | Dinh et al. |

FOREIGN PATENT DOCUMENTS

WO    WO 2009158668 A1 * 12/2009

OTHER PUBLICATIONS

Kaminskas et al "Pharmacokinetics and Tumor Disposition of PEGylated Methotrexate Conjugated Poly-L-lysine Dendrimers" Molecular Pharmaceutics 6:1190-1204. Published online May 19, 2009.*
Beaumont et al "Design of Ester Prodrugs to Enhance Oral Absorption of Poorly Permeable Compounds: Challenges to the Discover Scientist" Curr Drug Metabolism 4:461-485. Published 2003.*
Ettmayer et al "Lessons Learned from Marketed and Investigational Prodrugs" J Med Chem 47:2393-2404. Published online Apr. 13, 2004.*
Muller C "Prodrug Approaches for Enhancing the Bioavailability of Drugs with Low Solubility" Chem and Biodiversity 6:2071-2083. Published 2009.*
Singh et al "Recent Trends in Targeted Anticancer Prodrug and Conjugate Design" Curr Med Chem 15:1802-1826. Published 2008.*
Testa B "Prodrug Research: futile or fertile?" Biochem Pharmacology 68:2097-2106. Published 2004.*
Bhadra et al., "PEGylated-poly-l-lysine dendrimers for delivery of Chloroquine phosphate," Proceedings of the 2004 International Conference on MEMS, NANO and Smart Systems (ICMENS'04).
Cheng, "Dendrimers as Drug Carriers: Applications in Different Routes of Drug Administration," J. Pharm. Sci. (2007) 97:123-143.
International Search Report for PCT/US11/35103, mailed Aug. 9, 2011, 2 pages.
Kaminskas et al., "Impact of Surface Derivatization of Poly-l-lysine Dendrimers with Anionic Arylsulfonate or Succinate Groups on Intravenous Pharmacokinetics and Disposition," Mol. Pharm. (2007) 4:949-961.
Svenson et al., "Dendrimers as versatile platform in drug delivery applications," Eur. J. Pharm. Biopharm. (2009) 71:445-462.

* cited by examiner

*Primary Examiner* — Cecilia J Tsang
*Assistant Examiner* — Zachary J Miknis
(74) *Attorney, Agent, or Firm* — Morrison & Foerster, LLP

(57) ABSTRACT

The invention relates to compositions that comprise dendrimers useful in medical and veterinary applications that provide controlled release of drugs, such as peptides, nucleic acids and small molecules. The drugs are covalently coupled to the dendrimer through a linkage that releases the drug or a prodrug through controlled beta elimination.

18 Claims, 8 Drawing Sheets

Typical dendrimer structure starting from a core with three functional groups.

Polyamidoamine (PAMAM) Dendrimers

PAMAM$_{32}$-(PEG5000)$_{30}$ with therapeutic agents of varying sizes drawn to scale and immersed in the PEG shell. methotrexate (0.454 kDa), insulin (globular, 5.8 kDa), GLP1 (α-helix, 3.3 kDa), IL1-RA (Anakinra; globular, 17.3 kDa), erythropoietin protein (4-helix bundle, 18 kDa)

Linear free energy relationship of the half-lives for release of H-Lys(DNP)-OH from substituted (phenylsulfonyl)ethyl linked carbamates.

Linear free energy correlation between rate of H-Lys(DNP)-OH release where, $R^2$ = —$(CH_2)_3C\equiv CH$ at 25°C from compounds of Figure 5 and the Hammett $\sigma_p$; left to right, $R^1$ = —OMe, —$CH_3$, —H, —Cl Rat PK of Illustrative Conjugates

* Serum concentration of conjugates after i.v. administration

CONTROLLED DRUG RELEASE FROM DENDRIMERS

CROSS-REFERENCE TO RELATED APPLICATION

This application is the national phase of PCT application PCT/US2011/035403 having an international filing date of 5 May 2011, which claims benefit under 35 U.S.C. §119(e) to provisional application 61/331,749 filed 5 May 2010. The contents of the above patent applications are incorporated by reference herein in their entirety.

TECHNICAL FIELD

The invention relates to delivery systems for drug molecules coupled to dendrimers. More specifically, the invention relates to compositions that provide for the release of multiple molecules of drug from protected dendrimeric macromolecules.

BACKGROUND ART

There is a plethora of approaches to arranging for controlled release of drugs or growth factors useful in medicine. For example, compositions and methods have been described for controlled release of drugs covalently coupled to polyethylene glycol (PEG). As opposed to a drug bound irreversibly to PEG in order to enhance its half-life and diminish its immunogenicity, conjugates have been prepared wherein PEG is a releasable carrier of the drug or prodrug. Typically, the drug is attached by an ester or carbonate linkage that can be cleaved by esterase-catalyzed hydrolysis. The adjustment of release rates in these cases is, however, difficult. Examples are PEG-camptothecin, PEG-SN38, PEG-irinotecan and PEG-docetaxel. Additional adaptations have been made to accommodate amine-containing drugs whereby a PEG moiety is connected by a cleavable ester to a self-immolating carbamate. This technology has been applied to peptides and proteins as well as to daunorubicin, amphotericin, Ara-C and other small molecules.

Another system has been developed at the Weizmann Institute wherein PEG or other macromolecule is attached to beta elimination linkers such as fluorenyl methoxycarbonyl (Fmoc) or its 2-sulfo derivative (Fms). These are described in U.S. Pat. No. 7,585,837. However, rate-of-release control remains a problem.

PCT publication WO2009/158668 describes releasable drug conjugates to macromolecules wherein the rate of beta elimination is controlled by a trigger independent of the link to the macromolecule itself. This solves a problem left unsolved in the prior art.

The release mechanism set forth in the '668 PCT publication has not been applied to instances where a multiplicity of drug molecules is coupled covalently, but releasably, to dendrimeric macromolecules. It is also limited to drugs that contain an amine functional group. In addition to providing a controllable rate of release of more than one drug molecule from the dendrimer itself, this approach offers a means whereby the coupled drug is protected from hydrolysis by the presence of a protective polymer, such as PEG, on different sites at the surface or interstices of the solid support.

Dendrimers have been used as carriers for therapeutic compounds, either by entrapment of a drug in cavities within the dendrimer, or by covalently linking drug molecules to the surface. This is reviewed in Svenson, S., *Eur J Pharm Biopharm* (2009) 71:445-462 and Cheng, Y., *J. Pharm. Sci.* (2007) 97:123-143. Entrapment within dendrimer cavities is limited to small molecules, and covalent attachment approaches have thus far been limited to systems in which a small drug is hydrolytically or enzymatically cleaved from the dendrimer surface. Unmodified cationic dendrimers such as polyamidoamine dendrimer (PAMAM) or poly-L-lysine (PLL) have biocompatibility and toxicology shortcomings, for example, disruption of cell membranes and also have very short half-lives, typically <20 min. Toxicity may be reduced by functionalizing the surface of the dendrimer with non-ionic or anionic groups (Kaminskas, L., et al., *Mol Pharm* (2007) 4:949-961). PAMAM dendrimers are not biodegradable and are retained in the liver and kidney, raising a concern—albeit unproven—of toxicity upon chronic dosing, though PLL dendrimers while retained in the liver and kidney, appear to be broken down to constituent monomers.

It has been shown that PEGylation of PAMAM and PLL dendrimers neutralizes the surface positive charges and reduces or eliminates their propensity to lyse cells and cause acute toxicity. It has also been shown that the hydrophilic PEG moiety increases water solubility of guest drug molecules, and that PEGylated dendrimers effectively accumulate in tumor tissue via the enhanced permeability and retention and thus serve as targeting delivery vehicles for anti-tumor agents. PEGylated PLL shows almost complete (>90%) bioavailability when administered subcutaneously, providing downstream benefit in terms of patient compliance. Most importantly, PEGylation of cationic dendrimers can decrease renal filtration and dramatically increase the half-life from minutes to several days. Composite results show that long half-lives may be achieved with PEGylated dendrimers of MW≥40 kDa by varying either the number or size of the PEG chain. That is, the MW of the total dendrimer-PEG conjugate rather than the dendrimer or individual PEG chains dictates the extent of renal filtration. The size of PEGylated poly L-lysine dendrimer complexes can be specifically manipulated to dictate their pharmacokinetics, biodegradation and bioresorption behavior.

In particular, camptothecin attached to the dendrimer surface of $PLL_{16}(PEG5000)_8$ (i.e., a PLL with 16 functional groups at the surface, 8 of which are occupied by PEG of 5000 molecular weight) via an ester linker was completely protected from serum esterases, whereas an analogous PEG-camptothecin ester hydrolyzed ~10-fold faster in serum than buffer. A tetra-peptide chymotrypsin substrate attached to the dendrimer end groups of $PAMAM_{32}(PEG2000)_{20}$ was protected against chymotrypsin hydrolysis ($k_{cat}/K_M$ 0.1 uM$^{-1}$ s$^{-1}$) compared to the peptide-dendrimer without PEG (~5-fold), or to the free peptide (~8-fold), or to the peptide attached to PEG (~12-fold).* IFN-α-2b attached to the core of a 4-armed PEGylated-dendrimer showed ~10-fold lower cytotoxicity and anti-viral activity, as well as trypsin resistance and prolonged serum half-life compared to the free cytokine. Thus, it appears that molecules covalently bound to a dendrimer core and immersed within a PEG layer are protected against hydrolytic enzymes.

* The rate of diffusion of chymotrypsin into the PEG shell is $k_{cat}/K_M$; so the results indicate that proteins of at least this size (25 kDa) should as well escape out of the PEG layer.

The compositions of the invention overcome problems associated with coupling drugs to the conventional monovalent linear PEG carrier. In order to minimize kidney filtration, the molecular weight of the PEG carrier must be at least about 40,000 and the drug is limited therefore to about 1 μmole per 40 mg PEG. Thus, only very potent drugs can employ this system as a practical matter. Linear PEG's also provide only limited protection against enzymes that may modify and/or destroy the bound drug. Drugs bound to linear PEG may retain significant biological activity; while this is a requirement for a stably-modified drug, use of PEGylated-drug as a carrier for slow release of active free drug requires that the PEGylated form be substantially inactive due to the relatively higher dosages involved. The present invention permits increasing the drug payload and protects the drug against degrading enzymes as well as blocking access of the drug to its biological receptor. Like the technology described in the '668 publication, the activity of the drug is silenced until it is released, permitting administration of relatively large doses as depots.

DISCLOSURE OF THE INVENTION

The invention provides controlled release forms of multiple molecules of drugs, such as growth factors and small molecule drugs, coupled covalently to sites on dendrimeric macromolecules that can serve as delivery systems to extend the half-life of such drugs or growth factors. A linker is covalently bound to multiple sites on the dendrimer, which linker is in turn coupled to an appropriate drug or prodrug. The drug or prodrug is then released at the desired rate through a beta elimination reaction at physiological pH. In an additional embodiment, the drug sites on the dendrimer may be contained within a protective layer of polymer bound to adjacent sites on the solid support.

Thus, in one aspect, the invention is directed to a multiplicity of substituents of the formula

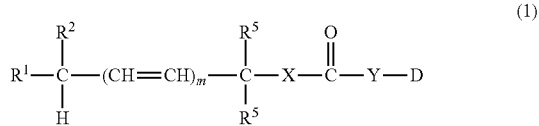

(1)

m=0-1 at least one, or both $R^1$ and $R^2$ is independently CN; $NO_2$;
optionally substituted aryl;
optionally substituted heteroaryl;
optionally substituted alkenyl;
optionally substituted alkynyl;
$COR^3$ or $SOR^3$ or $SO_2R^3$ wherein
  $R^3$ is H or optionally substituted alkyl;
  aryl or arylalkyl, each optionally substituted;
  heteroaryl or heteroarylalkyl, each optionally substituted; or
  OR or $NR_2$ wherein each R is independently H or optionally substituted alkyl;
$SR^4$ wherein
  $R^4$ is optionally substituted alkyl;
  aryl or arylalkyl, each optionally substituted; or
  heteroaryl or heteroarylalkyl, each optionally substituted;
wherein $R^1$ and $R^2$ may be joined to form a 3-8 member ring; and
wherein one and only one of $R^1$ and $R^2$ may be H or may be alkyl, arylalkyl or heteroarylalkyl, each optionally substituted;
each $R^5$ is independently H or is alkyl, alkenylalkyl, alkynylalkyl, aryl, arylalkyl, heteroaryl or heteroarylalkyl, each optionally substituted;

D is a residue of a drug or prodrug coupled through O, S, or N;
Y is absent and X is O or S; or
Y is $NBCH_2$ and X is O;
wherein B is alkyl, aryl, arylalkyl, heteroaryl or heteroarylalkyl, each optionally substituted; and
wherein one of $R^1$, $R^2$, $R^5$ or B is coupled to a dendrimeric macromolecule.

In some embodiments, said dendrimeric macromolecule has a G of at least 2, 3 or 4, wherein G is the number of generations included in the dendrimer, where the core of the dendrimer is assigned G=0. G values of 3 or 4 are preferred when Y is absent.

Said dendrimer may optionally also be further coupled to a protective inert polymer, such as PEG.

Alternatively phrased, the invention is directed to a dendrimeric macromolecule coupled, optionally through an additional linker, to a multiplicity of substituents of the formula

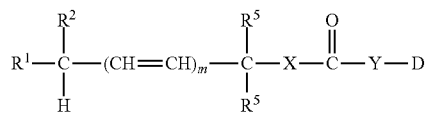

(2)

wherein the variables are defined as above—specifically
m=0-1
at least one or both of $R^1$ and $R^2$ is independently CN; $NO_2$;
optionally substituted aryl;
optionally substituted heteroaryl;
optionally substituted alkenyl;
optionally substituted alkynyl;
$COR^3$ or $SOR^3$ or $SO_2R^3$ wherein
  $R^3$ is H or optionally substituted alkyl;
  aryl or arylalkyl, each optionally substituted;
  heteroaryl or heteroarylalkyl, each optionally substituted; or
  OR or $NR_2$ wherein each R is independently H or optionally substituted alkyl;
$SR^4$ wherein
  $R^4$ is optionally substituted alkyl;
  aryl or arylalkyl, each optionally substituted; or
  heteroaryl or heteroarylalkyl, each optionally substituted;
wherein $R^1$ and $R^2$ may be joined to form a 3-8 member ring; and
wherein one and only one of $R^1$ and $R^2$ may be H, or may be alkyl, arylalkyl or heteroarylalkyl, each optionally substituted;
each $R^5$ is independently H or is alkyl, alkenylalkyl, alkynylalkyl, aryl, arylalkyl, heteroaryl or heteroarylalkyl, each optionally substituted;
D is a residue of a drug or prodrug coupled through O, S, or N;
Y is absent and X is O or S; or
Y is $NBCH_2$ and X is O;
wherein B is alkyl, aryl, arylalkyl, heteroaryl or heteroarylalkyl, each optionally substituted; and
wherein said coupling is through any of $R^1$, $R^2$, $R^5$ or B.

The dendrimer may also optionally comprise a multiplicity of protective inert polymers, such as PEG.

The compositions of the invention thus offer prolonged blood circulation times, protection of drugs against hydrolases/proteases, high capacity, and inactivity against targets until released.

In other aspects, the invention is directed to methods to prepare the compositions of the invention, and methods to employ them in medical/veterinary/physiological procedures. It also includes intermediates and precursors in the synthesis of formulas (1) and (2).

The invention thus further includes "precursor" molecules of formula (3) in which L is a nucleofuge—i.e., a leaving group that permits binding of a nucleophile. Thus, the invention includes compounds with formulas identical to that of formula (I), wherein multiple substituents are coupled to a dendrimeric macromolecule through $R^1$, $R^2$, $R^5$, or B except that in lieu of the drug or prodrug, the nucleofuge, of formula (3), instead, is present, i.e., the dendrimer macromolecule has substituents of formula (3)

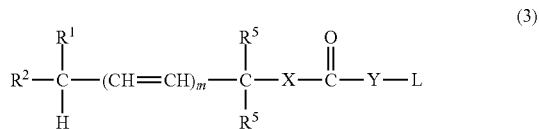

(3)

wherein $R^1$, $R^2$, $R^5$, X, Y and m are as defined in formula (1) or (2); and wherein L is a nucleofuge for coupling the drug or prodrug to the remainder of the molecule.

In some embodiments of formula (3), the dendrimer has not yet been coupled. Similarly, formula (1) or (2) without coupling to the dendrimer may be used as an intermediate. These intermediates can be summarized in formula (5):

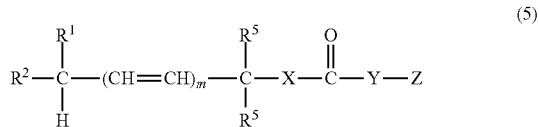

(5)

where Z is a drug or prodrug or a nucleofuge.

The coupling of any of these intermediates to dendrimer may employ a "connector"—i.e., one or more bifunctional organic molecules that connect the substituents on these formulas to the dendrimer.

More generally, the invention includes compounds of the formula:

M-(J-D)

wherein M is a dendrimer, D is a drug and J is a joining moiety that releases D by a beta elimination mechanism, wherein m is at least 8, and may by larger—e.g., 16, 32 or more. Intermediate values for m are also included.

MODES OF CARRYING OUT THE INVENTION

The present invention represents an improvement over standard PEGylation practices, and has additional advantages over the PEGylated releasable drug compositions such as those described in the above-referenced PCT publication WO2009/158668. Advantages include retaining a drug or prodrug in inactive form until released from the macromolecular carrier, a multiplicity of binding sites for the drug so that the drug dosage may be increased, thus permitting delivery of less potent drugs, and provision of protection against degrading enzymes or other inactivating conditions.

Another advantage of the compositions of the invention is that they afford effective delivery of drugs to the lymphatic system. Because the compounds of the invention have molecular weights that are significantly higher than the molecular weight of the drug, they are capable of maintaining the drug in the lymphatic system when the compounds are administered subcutaneously. Compounds with molecular weights of 40,000 or more are effectively maintained in the lymphatic system. Further, because the lymph lacks esterases present in plasma that might release drugs from esterified linkages, the favorable pH of the lymph (which is identical to that of plasma) permits release of the active drug from the conjugate. Thus, the compounds of the invention effectively release drug into the lymph when delivery to the lymph is desired, as would be the case, for example, with respect to lymphomas.

The compositions of the invention comprise dendrimer macromolecules coupled to multiple copies of one or more drugs and optionally further coupled to protective hydrophilic polymers such as PEG. In one embodiment, the dendrimer has a generation value of at least 4, where the core is assigned generation zero.

Dendrimers are synthetic polymers characterized by repeated chain branchings emanating from a central core, giving rise to a fractal-like topology and a large number of chain endings. Dendrimers are composed of a core, one or more layers (or generations) of branched monomers, and a layer of end-groups that double each "generation" and terminate the various chains.

Figure 1:
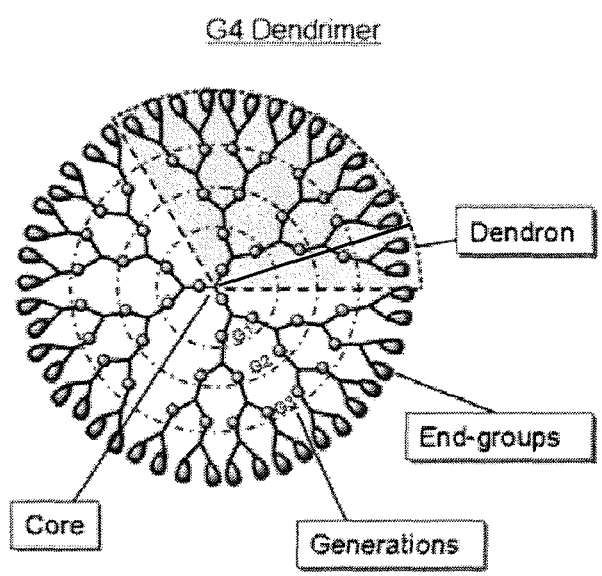
FIG. 1 shows a typical dendrimer structure that has a core with three functional groups.
Figure 2A:
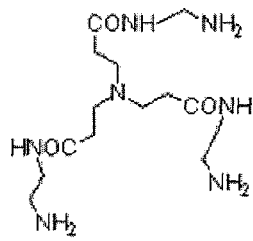
FIGS. 2A and 2B show a typical monomer for the production of a polyamidoamine dendrimer (PAMAM) and an early-stage phase of construction of said dendrimer, respectively.
Figure 2B:
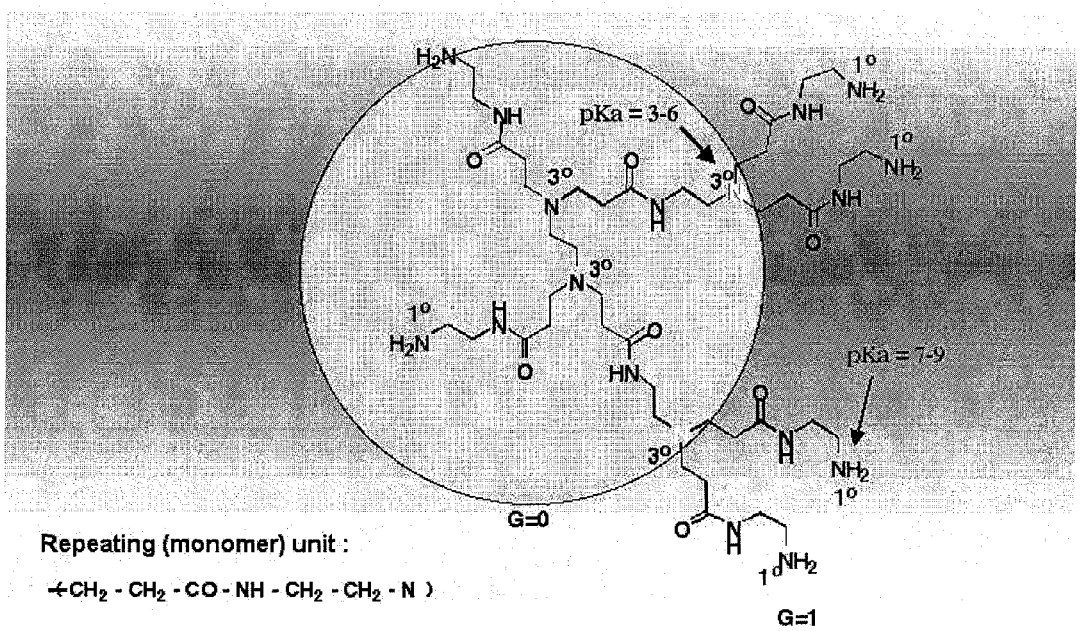

Dendrons are wedge-shaped structural sub-components of a parent dendrimer. Each functional group of a core gives rise to a dendron; at higher generations, branches arising from a functional group can be viewed as small dendrons. FIG. 2 shows a typical dendrimer structure.

Generation, G, refers to the number of layers in the dendrimer, and Z is the number of end groups on the dendrimer outer surface. As used herein, the core is generation 0 (G0). A monomer directly attached to the core can be considered a 1st generation monomer (G1); a monomer attached to a G1 monomer is a 2nd generation monomer (G2), etc. In this system of numbering $Z=2^{(G+1)}$. Thus, for a dendrimer where the core has 2 functional groups, for G0 $Z=2$ ($2^{(0+1)}$), for G1 $Z=4$ ($2^{(1+1)}$, etc.\

\ Some workers refer to the layer wherein a monomer is coupled to the core as G0, especially for polyamidoamine (PAMAM) dendrimers; thus, $Z=2^{(G+2)}$ and the designated G is one number lower than used here (i.e., G1 here is G0 in this alternative designation).

A variegated (i.e., multi-functional) dendrimer has more than one type of functional group incorporated into at least one generational layer (Roberts, B. P., et al., *New Journal of Chemistry* (2008) 32:1543-1555). Variegation of dendrimer end-groups allows detailed control over the chemical composition of the surface, while variegation of a more internal monomer provides control of its emanating branch(es) or an entire dendron.

Exemplary dendrimers include dendrimeric forms of poly-L-lysine (PLL) and polyamidoamine (PAMAM). The structure of one embodiment that may form the core of a PAMAM dendrimer is shown in FIG. 3A and an alternative form is shown in FIG. 3B where coupling has already occurred at two of four available amino groups.

Synthesis of Dendrimers

Four and eight-branched (Z=4 and 8) Fmoc-PLL-resin (Applied Biosystems) and t-Boc-PLL-benzhydryl amides (Aldrich) are commercially available, as are a large number of functionalized PEG derivatives (e.g., on the World Wide Web at creativepegworks.com).

Dendrimers can be synthesized by divergent or convergent approaches (Carlmark, A., et al., *Chem Soc Rev* (2009) 38:352-362). Divergent synthesis assembles the molecule from the core, extending radially in each generation to the periphery, whereas convergent methods start at the surface and pre-synthesized units (dendrons) are attached together. In some methods, a hybrid synthesis strategy is employed, for example a strategy wherein initial synthesis is divergent, and final synthesis employs attachment of more elaborate dendron units. Synthesis can be either in solution or on a solid support.

In an example of divergent dendrimer growth, starting from an initiator core containing two amino groups (e.g., Lys), a generation is grown by attaching monomers with two N-blocked functional groups (e.g., tBoc$_2$-Lys) to each core amino group, followed by blocking group removal to give a dendrimer with four amino end-groups. This can be repeated multiple times to form dendrimers with 8, 16, 32, etc., amino groups at the surface. As generations increase, steric congestion increases, surface groups become less accessible, and incomplete reactions may result in non-perfect dendrimers.

In convergent synthesis, individual dendrons are synthesized first and then coupled to a core molecule. The dendrons are typically constructed by the same strategies as for divergent growth, and once the dendrons have reached the desired generation they are coupled to a small core molecule. Thus, two PLL dendrons can be prepared as described above, and then connected to a Lys core to make a PLL dendrimer. The last coupling step is potentially difficult due to steric hindrance, but the large difference in size between the dendrimer and dendrons allows purification of the final product.

Characteristics of Dendrimers

Dendrimers have been extensively studied by a variety of physical, computational and experimental approaches (Caminade, A., et al., *Advanced drug delivery reviews* (2005) 57:2130-2146).

For example, Table 1 shows how PAMAM and PLL dendrimer diameters grow with increasing generation. With increasing generations, dendrimers develop through a continuum of molecular shapes ranging from open, extended structures to ellipsoids, to closed globular spheroids. Since the number of ends increase exponentially with generation, and surface area increases with the square, steric crowding of the branches at high generations results in a crowded surface; after about G5 (Z=64) there is a decrease in accessibility of the ends and thus their reactivity. The high surface and relatively lower interior densities of larger dendrimers supports cavities with diameters ranging from 5 to 15 Å that may be joined to channels connecting to the surface.

TABLE 1

Some properties of PAMAM and PLL dendrimers

| Generation * | MW | Diameter (Å) | Density (=MW/vol) | Surface area (Å$^2$) | Surface amines (Z) |
|---|---|---|---|---|---|
| PAMAM | | | | | |
| 1 | 517 | 15 | 0.29 | 707 | 4 |
| 2 | 1430 | 22 | 0.26 | 1520 | 8 |
| 3 | 3256 | 29 | 0.25 | 2641 | 16 |
| 4 | 6909 | 36 | 0.28 | 4069 | 32 |
| 5 | 14215 | 45 | 0.30 | 6359 | 64 |
| 6 | 28826 | 54 | 0.35 | 9156 | 128 |
| PolyLys | | | | | |
| 4 | 3962 | 34 | 0.19 | 3630 | 32 |
| 5 | 8065 | 45 | 0.17 | 6359 | 64 |
| 6 | 16269 | 59 | 0.15 | 10930 | 128 |

Synthesis of PEGylated Dendrimers

Cationic dendrimers up to 4 or 5 generations (Z=32 or 64) have been efficiently PEGylated on their surfaces (Kaminskas, L., *Mol Pharm* (2008) 5:449-463; Fox, M. E., et al., *Mol Pharm* (2009) 6:1562-1572; and Hedden R. C., et al., *Macromolecules* (2003) 36:1829-1835). Using variegated dendrimers (Roberts, B. P., supra), it is also possible to control the degree (i.e., density) and specific sites of PEGylation or drug conjugation of dendrimers. For example, using a residue containing two different (e.g., Glu, Cys) or orthogonally protected (e.g., α-Fmoc-ε-tBoc-Lys) functional groups at the last generation, selective deblocking allows a drug to be attached to one group and PEG to the other; hence, a drug:PEG of 1:1. It is also possible to attach a moiety (e.g., drug) to one functional group and another bifunctional monomer to the other; this terminates branching from one site, but allows continuation at the other; here, PEGylation of surface groups would provide a drug:PEG of 1:2. Numerous variations of structures are feasible using variegated dendrimers.

Table 2 summarizes the dimensions (i.e., outer radii of the dendrimer and PEG-dendrimer, thickness and volume of the PEG layer) of G3 to G5 PAMAM dendrimers conjugated to PEG 550 and 5000 with two different grafting densities (n=Z and Z/2). In general, the PEG molecules extend from the surface ~11 or 12 Å per 1,000 MW to form a shell or "brush" around the dendrimer. With increasing PEG density, ellipsoid dendrimers become almost spherical, and the PEG molecules more "stretched", thus increasing the PEG layer thickness. Each glycol unit of a PEG is 3.3 Å, so a 5,000 kDa PEG (113 units) has a fully extended length of 377 Å, considerably larger than the ~55 Å PEG shell of the PEGylated dendrimer.

TABLE 2

Dimensions of PEG-PAMAM constructs *

| | $R_d$ (nm) | R (nm) | L (=R − $R_d$) (nm) | shell vol (nm$^3$) |
|---|---|---|---|---|
| PAMAM$_{32}$(PEG5000)$_{30}$ | 2.42 | 8.06 | 5.64 | 2133 |
| PAMAM$_{64}$(PEG550)$_{32}$ | 2.31 | 3.02 | 0.71 | 64 |
| PAMAM$_{64}$(PEG550)$_{60}$ | 2.53 | 3.38 | 0.85 | 94 |
| PAMAM$_{64}$(PEG5000)$_{32}$ | 2.76 | 7.81 | 5.05 | 1906 |
| PAMAM$_{64}$(PEG5000)$_{60}$ | 2.74 | 8.87 | 6.13 | 2836 |
| PAMAM$_{128}$(PEG5000)$_{88}$ | 3.22 | 9.72 | 6.50 | 3705 |

* $R_d$ = dendrimer radius, R = total radius, L = thickness of PEG layer.

Figure 4:
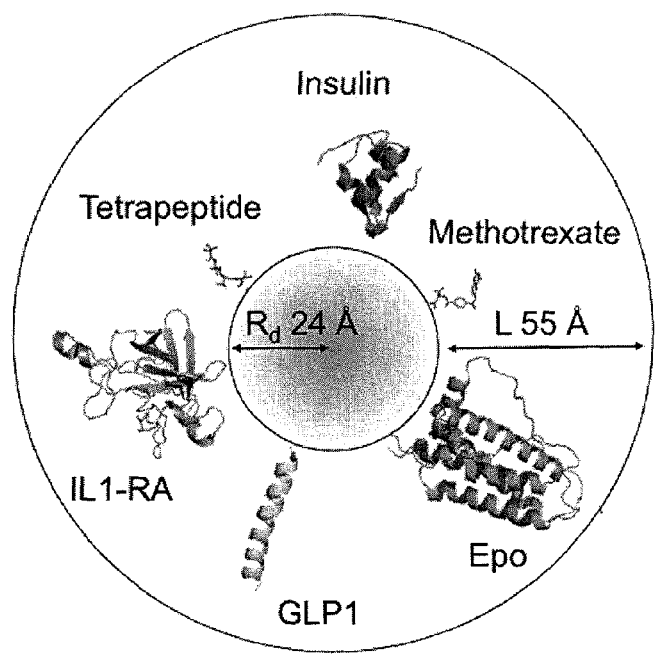
FIG. 4 is a diagram of a prior art description of a PEG protected PAMAM dendrimer showing relative dimensions of coupled drugs.

In the compositions of the present invention, suitable drugs are releasably coupled to multiple sites on a dendrimeric macromolecule through linkages which permit release of the drug or prodrug by β-elimination under physiological conditions. A depiction of the prior art (lacking the β-elimination release system) shown in FIG. 4 provides a conceptual understanding of the type of delivery system contemplated by the invention.

Additional PEGylated polylysine dendrimers useful in the invention have been described, recently, by Choi, J. S., et al., *Bioconjugate Chem.* (1999) 10:62-65. In these dendrimers, as shown in FIG. 4, the polyethylene glycol polymer is internal to the dendrimer and is essentially at the G0 level.

Figure 5:
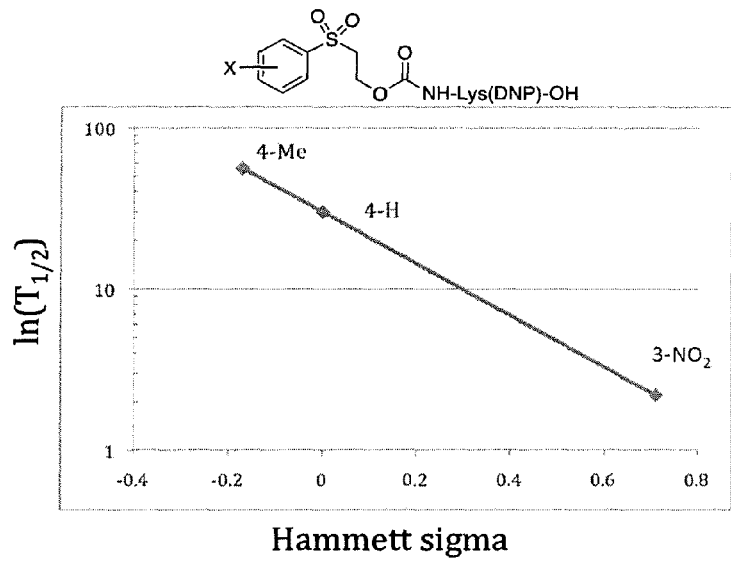
FIG. 5 is a graph showing the relationship of free energy to half-life for release of label from substituted β-elimination compounds.

FIG. 5 depicts the reported diameters of a G4 PAMAM dendrimer (Z=32; r~2.5 Å) in which surface residues are attached to PEG 5000 to give a ~55 Å shell thickness (Lee, H., et al., *J. Phys. Chem.* (2009) 113:13202-13207). Superimposed within the PEG shell are scaled drawings of a typical small molecule (ca. 10 Å), a 20 residue a-helix (~6-turns, 34×15 Å, 30 nm$^3$; e.g., type B1 gCPR peptide ligand), a ~20 kDa 4-helix bundle (v=19.5 nm$^3$), a 6 kDa globular protein (d=26 Å, v=78 nm$^3$) and 20 kDa globular protein (d=40 Å, v=260 nm$^3$). Thus, small molecules and many therapeutic peptides/proteins would fit within the dimensions/volume of a PEG 5000 shell, providing that a) suitable orientation of the guest molecule can be achieved, and b) that the PEG density is sterically accommodating. The PEG MW could be increased to 10,000 which, although not yet studied, should provide a larger shell, afford more protection, and accommodate the larger peptides/proteins.

Nature of the Drug Conjugate

The drug conjugate of formula (1) or (2) is designed to control the pharmacokinetics of the drug or prodrug the residue of which when coupled to the remainder of the molecule is designated as "D". The mechanism whereby the drug or prodrug is released is shown below. The rate is controlled according to a pH dependent β-elimination mechanism. The groups $R^1$ and $R^2$ are selected to provide the appropriate reactivity of the intervening proton in $R^1$—CH—$R^2$, thus providing control over the rate of drug or prodrug release. The properties of $R^1$ and $R^2$ may be modulated by the optional addition of electron-donating or electron-withdrawing substituents, for example, in aryl moieties contained therein.

In other words, either $R^1$ or $R^2$, or $R^1$ and $R^2$ in combination, can behave as the "trigger." The nature of the "trigger" controls the acidity of the intervening proton in $R^1$—CH—$R^2$, which, when released, permits the electron pair thus freed to effect β-elimination. For compounds wherein Y is absent; the half-life of the reaction may be in the range of that when Y is NBCH$_2$, depending on the nature of B. Half lives are very short for embodiments of B that are highly electronegative.

Examples of the ability to control release rates of drugs or prodrugs from these linkers are given in the Examples below and shown in FIGS. 9 and 10.

The mechanism of β-elimination release is shown below.

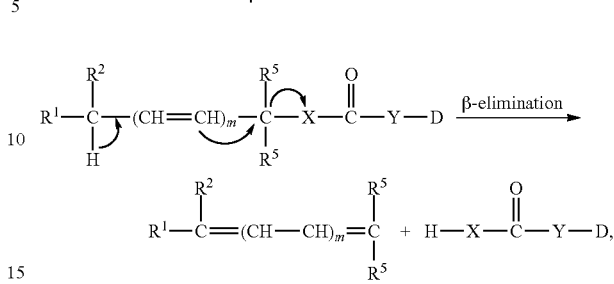

taking place under conditions typical of those of biological systems, for example a pH of between 6 and 8 and a temperature of between 25 and 40° C., at a rate such that the half-life of the reaction is between 1 and 10,000 hours, or between 1 and 5,000 hours, or between 1 and 1,000 hours or between 1 and 100 hours or between 1 and 10 hours. The product carbamic acids are typically highly unstable, and further decompose to release CO$_2$ (or COS) and DH when Y is absent, and CO$_2$, DH as well as B—NH$_2$ and H$_2$C=O when Y is NBCH$_2$.

In further detail, when X is O and Y is NBCH$_2$, the initial product of the β elimination is HX—(C=O)N(B)—CH$_2$D. In one mechanism, this intermediate may decompose according to:

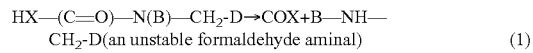

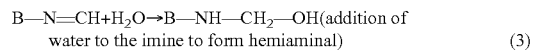

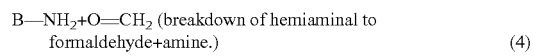

The various intermediates of the beta-elimination and subsequent decomposition reactions (1)-(4) shown above may be transient and therefore may not be detectable under physiological or other chemical reaction conditions.

When X is O or S and Y is absent, the drug itself has an amino group and the elimination leads directly to a carbamate which decomposes to drug and CO$_2$ or COS.

The degree to which the $R^1$ and/or $R^2$ groups activate the adjacent C—H bond may be expressed by the resulting acidity of the C—H bond; this acidity may in turn be expressed as the p$K_a$ of the C—H bond, wherein a lower p$K_a$ denotes a more acidic, more readily ionized C—H bond. Listings of approximate p$K_a$ values for various groups are common in the art, for example in Bordwell, F. G., "Equilibrium acidities in dimethyl sulfoxide solution," *Accounts of Chemical Research* (2002) 21:456-463 (incorporated herein by reference). Examples of suitably activating groups include, but are not limited to, optionally substituted aryls, optionally substituted heteroaryls, optionally substituted alkenes, optionally substituted alkynes, sulfones, sulfoxides, nitriles, ketones, esters, amides, and nitro groups. The $R^1$ and/or $R^2$ groups may be joined to form a cyclic structure, for example

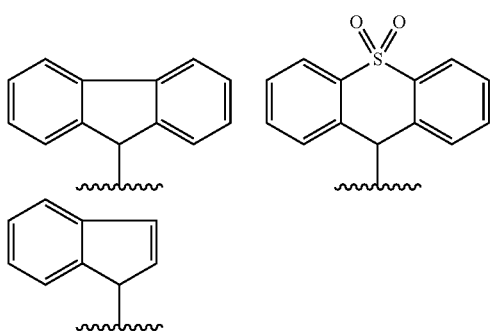

and substituted forms thereof.

Substituents on the $R^1$ and/or $R^2$ groups may optionally be added to provide further control over the acidity of the adjacent C—H, and thus the rate of the beta-elimination reaction. In general, electron-withdrawing substituents will increase the rate of the beta-elimination reaction, while electron-donating substituents will decrease the rate of the beta-elimination reaction. The electronic effect of various substituents is well-known in the art, and may be expressed for example as linear free-energy (Hammett) relationships. For aromatic systems, for example substituted aryl, heteroaryl, arylketones, heteroarylketone, arylsulfone, heteroarylsulfone, and arylsulfoxide, and heteroarylsulfoxide groups, the electronic effects of substituents are described by Hammett sigma parameters, with a positive sigma value denoting electron-withdrawing (rate-accelerating relative to H) and a negative sigma value denoting electron-donating (rate-retarding relative to H) effects. Table 3 provides a listing of Hammett sigma constants for various substituents.

An "electron-donating group" is substituent that will result in a decrease in the acidity of a benzylic hydrogen ion. Examples of suitable electron-donating substituents, include but are not limited to, lower alkyl, lower alkoxy, lower alkylthio, amino, alkylamino, and dialkylamino. "Electron-withdrawing groups" result in an increase in the acidity of a benzylic hydrogen ion. Examples of suitable electron-withdrawing substituents include, but are not limited to, halogen, difluoromethyl, trifluoromethyl, nitro, cyano, C(=O)—R, wherein R is H, lower alkyl, lower alkoxy, or amino, or SOR or $SO_2R$, where R is lower alkyl, aryl, or heteroaryl. Non-hydrogen electron-donating or electron-withdrawing substituents may be present in multiple positions on rings to which they are bound. While, for convenience, in most examples, only a single occurrence of a non-hydrogen substituent on a single ring is shown, multiple substituents may also be present and are within the scope of the invention. The substituents may be the same or different.

The foregoing is something of an oversimplification, because in some cases, whether a substituent is electron-withdrawing or electron-donating depends on its position in an aromatic ring. This is reflected in the following table of linear free energy (Hammett) relationships, where a positive sigma value denotes electron-withdrawing effect and a negative sigma value indicates an electron-donating effect. As shown in the table, for example, OMe is electron-withdrawing when present in the meta position but electron-donating in the para (or ortho) position.

TABLE 3

Selected Hammett Sigma Constants for Aromatic Substituents

| Substituent | σ(meta) | σ(para) |
|---|---|---|
| H | 0 | 0 |
| $CH_3$ | −0.07 | −0.17 |
| $CH_3CH_2$ | −0.07 | −0.15 |
| $Me_2CH$ | −0.05 | −0.15 |
| $Me_3C$ | −0.1 | −0.2 |
| $Me_3Si$ | −0.04 | −0.07 |
| $NH_2$ | −0.16 | −0.66 |
| $Me_2N$ | −0.15 | −0.83 |
| OH | +0.12 | −0.37 |
| OMe | +0.12 | −0.27 |
| $OCH_2CH_3$ | +0.10 | −0.24 |
| AcNH | +0.07 | −0.15 |
| Ph | +0.06 | −0.01 |
| $CH_2=CH$ | +0.05 | −0.02 |
| HC(=O)NH | +0.19 | 0 |
| F | +0.34 | +0.06 |
| Cl | +0.37 | +0.23 |
| Br | +0.39 | +0.23 |
| I | +0.35 | +0.18 |
| SH | +0.25 | +0.15 |
| MeS | +0.15 | 0 |
| $ClCH_2$ | +0.11 | +0.12 |
| $CF_3$ | +0.43 | +0.54 |
| CN | +0.56 | +0.66 |
| CHO | +0.35 | +0.42 |
| $CH_3C=O$ | +0.38 | +0.50 |
| $CO_2H$ | +0.37 | +0.45 |
| NO | +0.62 | +0.91 |
| $NO_2$ | +0.71 | +0.78 |
| $Me_3N^+$ | +0.88 | +0.82 |

When Y is $NBCH_2$, the nature of the B group influences the stability of the N-methylene-carbamate toward decomposition via E1-type elimination reactions.

E1 proceeds as shown:

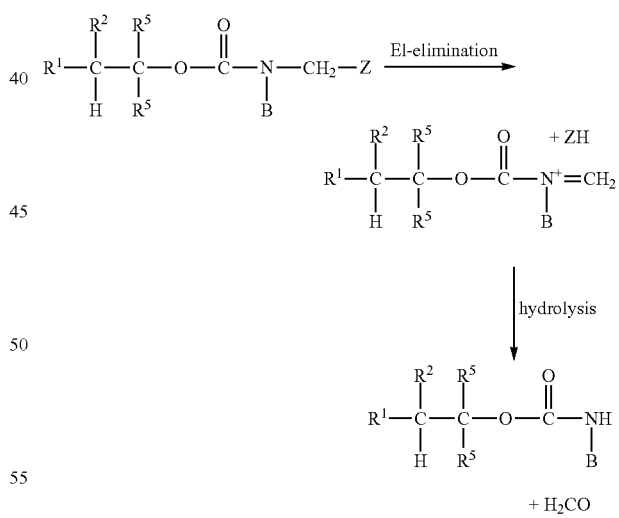

B groups that reduce the reactivity of the carbamate N lone pair, for example via extended conjugation and/or electron-withdrawing ability, reduce the rate of competing decomposition by the E1-elimination pathway. In preferred embodiments of the invention, B is optionally substituted aryl, or optionally substituted heteroaryl. In one embodiment of the invention, B is substituted aryl or substituted heteroaryl, substituted with groups having positive Hammett sigma constants (Table 3). In one specific embodiment of the invention, for example, B is phenyl or phenyl substituted with alkoxycarbonyl, CN, Br, $NO_2$, sulfonamide or carboxamide.

The embodiment wherein X is O and Y is $NBCH_2$, the $NBCH_2$ serves as an adaptor to provide the unstable carbamate thus permitting coupling to drugs that do not contain amino functional groups. It is estimated that only about 32% of the presently available small molecule drugs have primary or secondary amino groups available as functionalities. However, permitting the inclusion of groups with functional groups that are aliphatic primary or secondary alcohols permits about 45% of approved small molecule drugs to be included. Other functional groups that are acceptable to permit the constructs of the invention to contain the drug are sulfonamides, phenols, pyrroles, imides and thiols. Taken together, then, approximately 71% of currently approved drugs are amenable to inclusion in the constructs of the invention.

In embodiments where Y is $NBCH_2$, it is preferable that B include a stabilizer, such as an aryl group, which prevents spontaneous cleavage or hydrolysis.

SOME DEFINITIONS

The dendrimers may be coupled to Formulas 1, 2, or 3 through additional "connectors". The additional connectors are bifunctional organic compounds, such as DBCO—NHS. Many such connectors are commercially available, for example from Pierce Chemical Co, Rockford, Ill. Various bifunctional connecters are well known in the art, including dicarboxylic acids or anhydrides, diamines, or heterobifunctional connecters. The selection of the connector will, of course, depend on the nature of the functional groups on the substituents on the dendrimer and on the intermediates corresponding to formulas (1)-(3).

The term "alkyl" includes linear, branched, or cyclic saturated hydrocarbon groups of 1-8 carbons, or in some embodiments 1-6 or 1-4 carbon atoms.

The term "alkoxy" includes alkyl groups bonded to oxygen, including methoxy, ethoxy, isopropoxy, cyclopropoxy, cyclobutoxy, and similar.

The term "alkenyl" includes non-aromatic unsaturated hydrocarbons with carbon-carbon double bonds. By the term "alkenyl ($C_2$)" is meant a mono-, di-, tri-, or tetra-substituted carbon-carbon double bond of any geometric configuration.

The term "alkynyl" includes non-aromatic unsaturated hydrocarbons with carbon-carbon triple bonds. By the term "alkynyl ($C_2$)" is meant a mono- or di-substituted carbon-carbon triple bond.

The term "aryl" includes aromatic hydrocarbon groups of 6-18 carbons, preferably 6-10 carbons, including groups such as phenyl, naphthyl, and anthracenyl. The term "heteroaryl" includes aromatic rings comprising 3-15 carbons containing at least one N, O or S atom, preferably 3-7 carbons containing at least one N, O or S atom, including groups such as pyrrolyl, pyridyl, pyrimidinyl, imidazolyl, oxazolyl, isoxazolyl, thiazolyl, isothiazolyl, quinolyl, indolyl, indenyl, and similar.

In some instances, alkenyl, alkynyl, aryl or heteroaryl moieties may be coupled to the remainder of the molecule through an alkylene linkage. Under those circumstances, the substituent will be referred to as alkenylalkyl, alkynylalkyl, arylalkyl or heteroarylalkyl, indicating that an alkylene moiety is between the alkenyl, alkynyl, aryl or heteroaryl moiety and the molecule to which the alkenyl, alkynyl, aryl or heteroaryl is coupled.

The term "halogen" includes bromo, fluoro, chloro and iodo.

"Maleimido" refers to formula

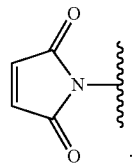

A "nucleofuge" is a leaving group that takes with it the electron pair by which it is bonded. Exemplary nucleofuges are halogen, OH, alkoxy, hydroxysuccinimide, paratoluenesulfonate, alkylsulfonate, and $R_2S^+$, wherein each R is independently alkyl, aryl, or heteroaryl.

The terms "protein" and "peptide" are used interchangeably regardless of chain length, and these terms further include pseudopeptides which comprise linkages other than amide linkages, such as $CH_2NH_2$ linkages as well as peptidomimetics.

The terms "nucleic acids" and "oligonucleotides" are also used interchangeably regardless of chain length. The nucleic acids or oligonucleotides may be single-chain or duplexed or may be DNA, RNA, or modified forms thereof with altered linkages, such as phosphodiesters, phosphoramidates, and the like. For both the proteins and nucleic acids useful as drugs in the invention, these terms also include those with side chains not found in nature in the case of proteins as well as pseudopeptide bonds and bases not found in nature in the case of nucleic acids as well as backbone modifications such as peptide nucleic acids.

Small molecules in the context of drugs is a term well understood in the art, and is meant to include compounds other than proteins and nucleic acids that either are synthesized or are isolated from nature and in general do not resemble proteins or nucleic acids. Typically, they have molecular weights <1,000, although there is no specific cutoff recognized. Nevertheless, the term is well understood in the fields of pharmacology and medicine.

A wide variety of drugs may be included as the embodiment of D. Each of these drugs will be coupled through a nitrogen, oxygen or sulfur to the remainder of the molecule. Examples of suitable drugs include those for human or veterinary use including, but not limited to, antidiabetic drugs; growth promoters; antibacterials including aminoglycosides, penicillins, cephalosporins, macrolides and peptides, trimethoprim, piromidic acid, and sulfamethazine; analgesic and anti-inflammatory drugs, antiallergic and antiasthmatic drugs, antihypercholesterolemic drugs, beta-adrenergic blockers and antihypertensive drugs, antineoplastic drugs, and antiviral drugs. As explained above, the inclusion of the "adaptor" $NBCH_2$ as Y permits drugs other than those bearing primary or secondary amines to be included.

Further examples of such drugs include alcohols such as paclitaxel and analogues, epothilones and analogues, camptothecin and analogues such as irinotecan, and nucleosides such as 5-fluorouracil and capecitabine. In another embodiment, the drug is a peptide comprising a serine residue. In another embodiment, the drug is a small molecule comprising an arylol group; examples of such drugs include sn-38, etilefrine, prenalterol, and estradiol. In another embodiment, the drug is a peptide comprising a tyrosine residue. If coupling is through S, the drug may be a small molecule comprising a thiol group. Examples of such drugs include penicillamine, captopril, and enalapril. The drug may be a small molecule comprising a thioaryl or thioheteroaryl group; examples of such drugs include 6-mercaptopurine. In another embodiment, the drug is a nitrogen-containing heterocycle; examples include 5-fluorouracil and allopurinol.

Other drugs are peptide, protein, and nucleic acid drugs. Examples of peptide drugs suitable for use in the invention include, e.g., glucagon-like peptide 1 (GLP-1), atrial natriuretic factor (ANF), and many others. Examples of protein drugs include immunotoxin SS1P, adenosine deaminase, arginase, and others.

Examples of nucleic acid-based drugs include the sense strand and antisense strand of any gene from an animal, and particularly from a mammal. Such genes can be those that are already the subjects of antisense DNAs or RNAs, or small interfering RNAs that have been provided with the purpose of treating various diseases, for example genes for protein kinase C-alpha, BCL-2, ICAM-1, tumor necrosis factor alpha and the like.

The term "precursor" refers to a dendrimeric macromolecule similar to formula (I), but wherein rather than linked to the drug or prodrug, the macromolecule is coupled to a nucleofuge for further binding to a drug or prodrug as in formula (3)

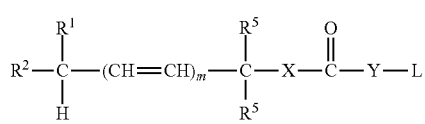
(3)

wherein $R^1$, $R^2$, $R^5$, X, Y and m are as defined in formula (1) or (2); and wherein L is a nucleofuge.

While typically, the active form of the drug is directly released from the conjugates of the invention, in some cases, it is possible to release the active drug in the form of a prodrug thereof. On example of such a system is shown below:

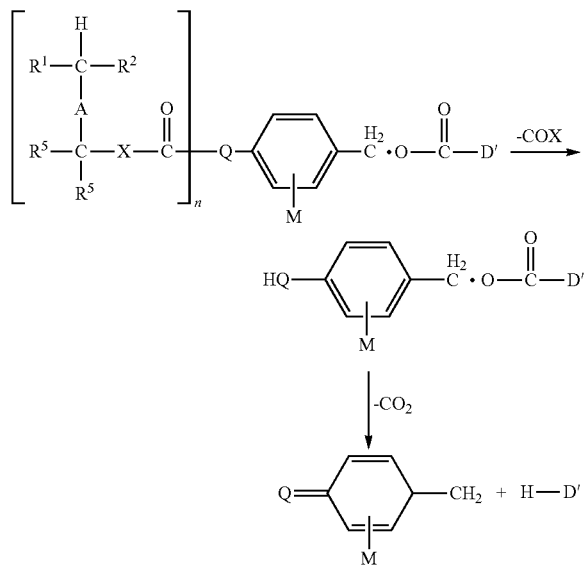

wherein Q=O or NH, D' is the active form of a drug,
M=usual aryl subsitutions.

To avoid misunderstanding, the "drug conjugates" described herein include conjugates both of drugs and prodrugs.

Exemplary Substituents

Because the substituents $R^1$, $R^2$, $R^5$, and X are shared by all of the compounds of formulas (1)-(3) and any intermediates in their preparation, the various embodiments of these substituents as presented in the alternative set forth below in connection with the compounds of formula (1) or (2) may be extrapolated to precursors and intermediates thereto.

When any substituent may itself be optionally substituted, the substitution on any ring system may be alkyl, alkenyl, alkynyl or an additional ring each optionally substituted. Optional substitutions on any substituent, including the above, include halo, nitro, cyano, OR, SR, $NR_2$, OCOR, NRCOR, COOR, $CONR_2$, SOR, $SO_2R$, $SONR_2$, $SO_2NR_2$, wherein each R is independently alkyl, alkenyl, alkynyl, aryl or heteroaryl.

As noted above, in the compounds of the invention, $R^1$ and $R^2$ together exert the most control over the release rate for the drug, though $R^5$ and m have some impact as well. In some instances, one of $R^1$ and $R^2$ is hydrogen or is alkyl, arylalkyl or heteroarylalkyl and the other comprises one of the remaining embodiments set forth hereinabove. In other instances, neither of $R^1$ and $R^2$ is hydrogen or is alkyl, arylalkyl or heteroarylalkyl.

For example, one of $R^1$ may be H and the other optionally substituted phenyl or both $R^1$ and $R^2$ may be optionally substituted phenyl. The substitutions on the phenyl rings may be at 1-5 positions but preferably 3 or less. If both $R^1$ and $R^2$ are optionally substituted phenyl, they need not be substituted identically, or may be identically substituted. Suitable substituents include methoxy, halo, nitro, cyano and the like for example as shown in Table 3 or the substitutions listed above.

In other embodiments, one or both of $R^1$ and $R^2$ is $R^6S$—, $R^6S(O)$ or $R^6S(O)_2$—, wherein $R^6$ is alkyl, substituted alkyl, aryl, substituted aryl, heteroaryl, or substituted heteroaryl. The remaining member of $R^1$ and $R^2$ may then be, H, for example, or any of the alternative embodiments set forth above.

In other instances, one or both of $R^1$ and $R^2$ may be cyano and the other optionally selected from the permissible substituents set forth above, in particular phenyl optionally substituted at one or more positions, for example, with halo, CN, $NO_2$, methoxy and the like.

In another set of instances, one or both of $R^1$ and $R^2$ is optionally substituted benzoyl and the other hydrogen or any of the other suitable choices, such as optionally substituted phenyl.

When $R^1$ and $R^2$ are joined to form cyclic structures, this includes groups wherein the $R^1$—CH—$R^2$ moiety forms a substructure such as, for example,

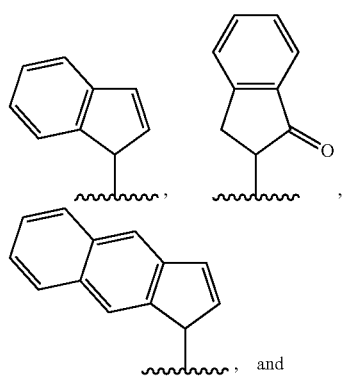

Figure 3:
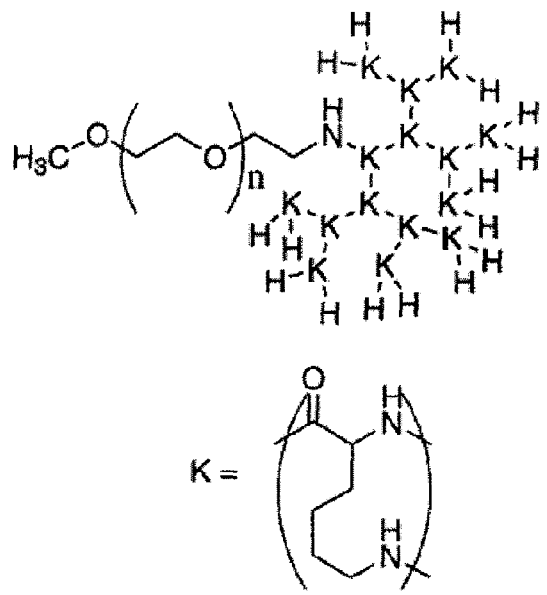
FIG. 3 is a diagram of a prior art description of a PEGylated polylysine wherein the PEGylation is contained within the dendrimer.

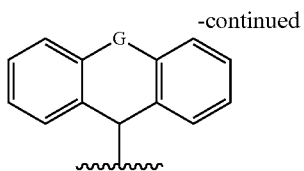

and forms thereof optionally substituted with electron-withdrawing and/or electron-donating groups as described above, wherein G is a bond; C=O; SO, $SO_2$, $CZ_2$, or $CZ_2CZ_2$ wherein each Z independently is H or Cl. In embodiments wherein Y is $NBCH_2$, the substituents D or a leaving group in general coupled to the $CH_2$ element may be released by a competing mechanism designated E1. This is illustrated in FIG. 3 where the leaving group or drug/prodrug, represented in the alternative by Z is removed as shown followed by the release of formaldehyde. This is a slower, competing reaction which is not controlled appreciably by Ph, and thus results in a lack of control of the rate of release. The level of competition by this E1 reaction is controlled by the nature of B which influences the stability of the N-methylene-carbamate by decomposition via E1 elimination. B groups that reduce the reactivity of the carbamate nitrogen loan pair reduce the rate of the E1 elimination pathway. These groups provide this control through extended conjugation and/or electron withdrawing ability and thus reduce the rate of E1. Thus, heteroaryl or aryl substituents are preferred especially those substituted with groups having positive Hammett sigma constants. For example, one embodiment is that wherein B is phenyl or phenyl substituted with alkoxycarbonyl, CN, $NO_2$ or Br.

Each $R^5$ is independently H, or is alkyl, alkenylalkyl, alkynylalkyl, aryl, arylalkyl, heteroaryl or heteroarylalkyl, each optionally substituted. In certain embodiments, each $R^5$ is H. In other embodiments, one of $R^5$ is H and the other is substituted alkyl or substituted phenyl, comprises an azidoalkyl group or is azido-$(CH_2)_{3-6}$, monoalkylamino-$(CH_2)_{3-6}$, $N_3(CH_2)_{3-6}N(Me)CO(CH_2)_{3-6}$—, or —$(CH_2)_{3-6}$—$CO_2H$, or a protected variant thereof. In additional embodiments, one of $R^5$ is any one of the particular embodiments described above, further comprising a dendrimer or a functional group allowing for connection to a dendrimer, and the other $R^5$ is H.

The B group may be alkyl, aryl, arylalkyl, heteroaryl, or heteroarylalkyl, each optionally substituted. The nature of the B group influences the stability of the N-methylene-carbamate toward decomposition via E1-type elimination reactions. B groups that reduce the reactivity of the carbamate N lone pair, for example via extended conjugation and/or electron-withdrawing ability, reduce the rate of competing decomposition by the E1-elimination pathway. In preferred embodiments of the invention, B is optionally substituted aryl, or optionally substituted heteroaryl. In one embodiment of the invention, B is aryl or heteroaryl, each substituted with at least one group having a positive Hammett sigma constant. In one specific embodiment of the invention, B is unsubstituted phenyl or phenyl substituted with alkoxycarbonyl, CN, $NO_2$, or Br, B may also be phenyl substituted with an aminocarbonyl, such as morpholinocarbonyl, or a sulfonamidyl, or B may be propargyl, 4-ethoxycarbonylphenyl, propyl, 4-(N,N-diethylcarboxamido)phenyl, 4-morpholinocarbonylphenyl, or 4-morpholinosulfonylphenyl. In additional embodiments, B is any one of the particular embodiments described above, further comprising a dendrimer or a functional group allowing for connection to a dendrimer.

Compounds of the invention either coupled to a dendrimer via one of $R^1$, $R^2$, $R^5$, and B or $R^1$, $R^2$, $R^5$, and B comprises a functional group that allows for connection to a dendrimer. Suitable functional groups that allow for connection to a dendrimer comprise an alkyl or aryl group, further substituted with a reactive chemical moiety. Thus, at least one of the $R^1$, $R^2$, $R^5$, and B groups comprises a dendrimer or an alkyl or aryl group further substituted with one or more amino, azido, hydroxy, carboxylic acid, alkynyl, thiol, maleimido, or 1,3-dicarbonyl groups, or protected variants thereof.

Synthesis of the Compounds of Formulas 1 or 2

The compounds of formulas (1) or (2) are derived from precursors and intermediates where either the drug/prodrug or the dendrimer is added as the last step. Thus, in one pathway, a compound of the formula

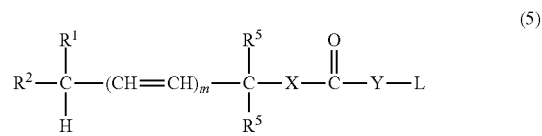

(5)

wherein $R^1$, $R^2$, $R^5$ or B (if present) are not yet coupled to the dendrimeric macromolecule can be used as an intermediate. Either the drug/prodrug or the dendrimer may be coupled first. If the dendrimer is coupled first, the novel compounds of formula (3) wherein a dendrimer is coupled to one of $R^1$, $R^2$, $R^5$ or B (if present) is formed. Alternatively, an intermediate containing the drug/prodrug can be first formed and then coupled to the dendrimer.

Thus, one step in the synthesis is coupling the remainder of the molecule to the dendrimer; thus, intermediates are synthesized which contain functional groups in the appropriate $R^1$, $R^2$, $R^5$ or B substituents that permit such coupling.

Methods for conjugation of the intermediates to the dendrimers are generally known in the art. In one method, an amide linkage is formed between an amino group and a carboxylic acid group; thus, a intermediate comprising an amino group can be conjugated to a dendrimer that contains or is modified to contain a carboxylic acid group, or a intermediate comprising a carboxylic acid group can be conjugated to a dendrimer comprising an amino group as the reactive group. The conjugation may be performed by reacting the intermediate and dendrimer in the presence of a condensing agent, for example a carbodiimide such as dicyclohexylcarbodiimide (DCC) or 1-(3-dimethylaminopropyl)-3-ethylcarbodiimide (EDCI), a uronium reagent such as O-benzotriazole-N,N,N', N'-tetramethyluronium-hexafluorophosphate (HBTU), or a phosphonium reagent such as benzotriazole-1-yl-oxy-tris-(dimethylamino)phosphonium hexafluorophosphate (BOP).

Alternately, the carboxylic acid group may be activated for conjugation in a prior step, for example by conversion to an acid chloride using thionyl chloride or oxalyl chloride, or to an active ester such as a pentafluorophenyl ester using a carbodiimide and pentafluorophenol or an N-hydroxysuccinimidyl ester using a carbodiimide and N-hydroxysuccinimide, and the resulting activated carboxylate may then be reacted with the amine in a second step. The amine and carboxylic acid groups may initially be present in protected form as required for stability and/or compatibility with additional chemical transformations, and deprotected prior to the conjugation step. Amine groups may be protected as carbamates, preferably tert-butoxycarbonyl ($^t$BOC), allyloxycarbonyl (Alloc), or other carbamate groups that may be removed under neutral-to-acidic conditions. Carboxylic acids may be protected as esters that may be removed under neutral-to-acidic conditions, such as tert-butyl (ᵗBu), trityl (Ph₃C), allyl (All), or methoxymethyl (MOM).

In a second method, a thioether linkage is formed between a thiol group and a maleimide group; thus, a intermediate comprising thiol group can be conjugated to a dendrimer comprising a maleimide group, or a intermediate comprising a maleimide group can be conjugated to a dendrimer that is modified, for example, by a bifunctional linker thiol group. The thiol group may initially be present in protected form as required for stability and/or compatibility with additional chemical transformations, and deprotected prior to the conjugation step. Suitable protecting groups include those that may be removed under neutral-to-acidic conditions, for example tert-butyl ethers (ᵗBu) or trityl ethers.

In a third method, a 1,2,3-triazole linkage is formed between an alkyne and an azide group; thus, a intermediate comprising an alkyne group can be conjugated to a dendrimer modified to contain an azide group, or a intermediate comprising an azide group can be conjugated to a solid support modified to contain an alkyne group. The conjugation reactions may be performed under metal catalysis, typically using copper or ruthenium, or may be performed in the absence of catalyst using an activated alkyne such as a cyclo-octyne. Related cycloaddition methods known in the art may be employed, for example Diels-Alder cycloadditions between a 1,3-diene and a dienophile.

In a fourth method, an enamino-ketone linkage is formed between an amino group and a 1,3-dicarbonyl group; thus, a intermediate comprising an amino group can be conjugated to a dendrimer modified to contain a 1,3-dicarbonyl group, or a intermediate comprising a 1,3-dicarbonyl group can be conjugated to a solid support comprising an amine group. In one embodiment, a intermediate comprising a 1,3-dicarbonyl group is reacted with an antibody such as m38C2 comprising a suitably reactive lysine 6-amino group (Doppalapudi, et al., *Bioorganic & Medicinal Chemistry Letters* (2007) 17:501-506, incorporated herein by reference).

Thus, the $R^1$, $R^2$, $R^5$, or B groups in the intermediate independently may optionally be substituted by optionally protected amine, optionally protected carboxylic acid, optionally protected thiol, maleimide, alkyne, or azide groups to allow for conjugation with dendrimers. Once conjugated, the $R^1$, $R^2$, $R^5$, or B groups independently are substituted by dendrimers connected via, for example, carboxylic amide, thioether, or 1,2,3-triazole groups.

Coupling of Drug/Prodrug

For conjugates where Y is absent, coupling of the drug is illustrated below. In formula (A), coupling to dendrimer may or may not have already been conducted. Typically, the drug is coupled prior to coupling to dendrimers. Thus, $R^1$, $R^2$ and $R^5$ are as above-defined or alternatively, one of $R^1$, $R^2$ and $R^5$ is coupled to a dendrimer.

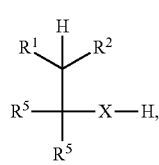

(A)

with a drug or prodrug molecule D. The compound of formula (A) is first activated for condensation by reaction with a suitable reagent, for example phosgene or triphosgene, optionally in the presence of N-hydroxysuccinimide; 1,1-carbonyldiimidazole; 1,1-carbonylditriazole; N,N-disuccinimidyl carbonate, or similar reagents for the conversion of a compound of formula (A) into an activated compound, wherein W=F, Cl, imidazolyl, triazolyl, or O-succinimidyl, and then coupled to the drug.

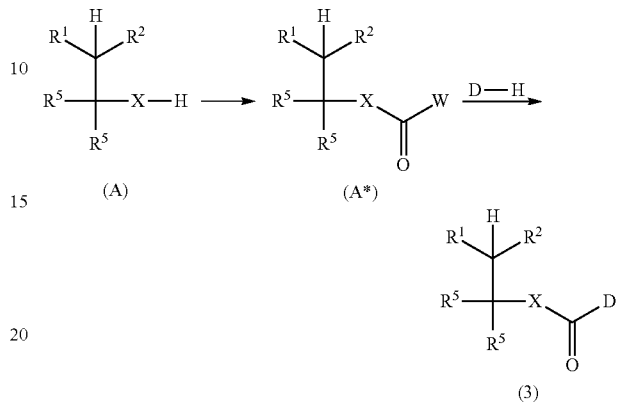

For example, reaction of a compound of formula (A) wherein x=O with triphosgene and N-hydroxysuccinimide yields a compound wherein x=O and W=O-succinimidyl:

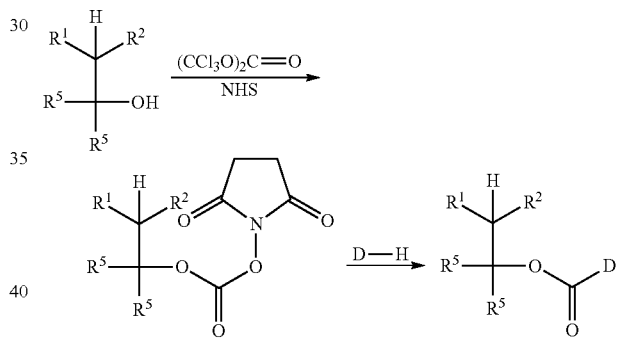

Compounds wherein x=O and W=O-succinimidyl are particularly preferred when the drug or prodrug molecule to be conjugated has an amino group. In this case, the resulting compound comprises a carbamate linkage. For cases wherein the drug or prodrug is a peptide or protein, the amino group that reacts with the intermediate may be a terminal alpha-amino group or the amino group of a side-chain, for example of a lysine, ornithine, or unnatural amino acid residue.

Alternatively, the activating reagent may be a substituted phenyl chloroformate, for example, 4-nitrophenyl chloroformate, 2,4-dinitrophenyl chloroformate, or pentafluorophenyl chloroformate, resulting in formation of an intermediate substituted phenyl carbonate.

Intermediates wherein x=O and W=F or Cl are particularly preferred when the drug or prodrug molecule to be conjugated has no amino group, but instead has a hydroxy group, for example when the drug or prodrug is a peptide or protein from a side-chain tyrosine, serine, or threonine residue, or when the drug or prodrug is nucleic acid-based such as a deoxynucleic acid or ribonucleic acid, or a small molecule.

The precursors wherein the drug is an oligonucleotide or nucleic acid may be prepared by chemical synthesis of the drug comprising a 5'-terminal modification that allows for conjugation. For example, the oligonucleotide may be chemically synthesized such that the 5'-terminal nucleotide unit, added at the last round of synthesis, comprises a phosphate group modified to contain an amino-alkyl group. The resulting amine-modified nucleic acid molecule is then conjugated to form a molecule of formula (3). See, for example, Zhao, et al., *Bioconjugate Chemistry* (2005) 16(4):758-766.

In the case of peptide-, protein-, or nucleic acid-based drugs, multiple reactive groups may be present leading to multiple reactions. The extent of this multiple reaction may be controlled using standard conditions known in the art, for example by varying the reaction temperature, concentrations, and stoichiometries in order to obtain the desired reaction product.

In one embodiment of the invention, where the drug is a peptide, the intermediate formed by reaction with an amino acid is then employed in standard peptide synthesis:

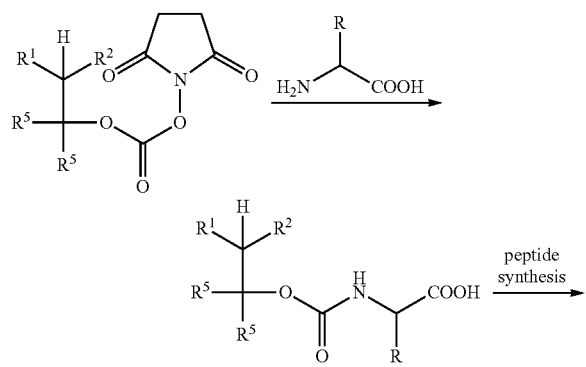

In another method, the intermediate is attached during the synthesis of the peptide. For example, the final step in the synthesis of the peptide by solid-phase peptide synthesis methods well-known in the art involves attachment of the N-terminal amino acid of the sequence of the peptide in protected form. The final step uses the N-terminal amino acid in a form using the intermediate as the protecting group, which is not removed.

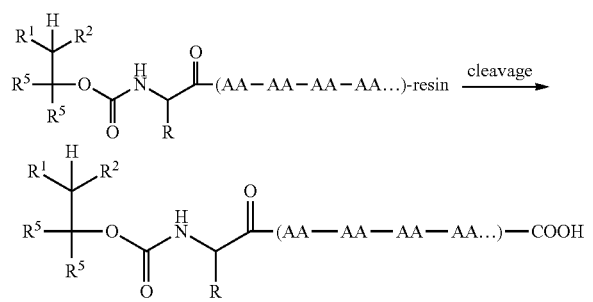

wherein R is the side chain of an amino acid.

This embodiment is advantageous in that the position and stoichiometry of derivitization is completely controlled.

Similar reactions are employed where the intermediate is a compound wherein Y is $NBCH_2$. The nucleofuge coupled to $CH_2$ is similarly displaced by the drug or prodrug. In this case, as well, the intermediate may or may not already be coupled to the dendrimeric macromolecule.

Preparation of Intermediate Compounds

Those intermediate compounds wherein m is 0 may be prepared by the addition of a carbanion $R^1R^2CH^-$ formed by reacting $R^1R^2CH_2$ with a strong base, for example butyllithium, NaH, lithium diisopropylamide, lithium bis(trimethylsilylamide), or similar, with a molecule to produce a compound of formula (A)

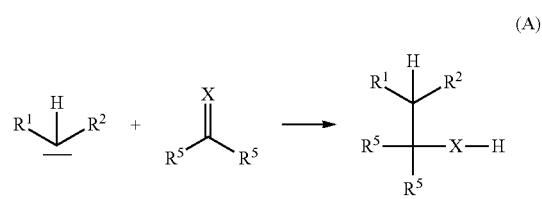

Alternatively, compounds of formula (A) wherein x=O and one $R^5$ is H may be prepared by a two-step process. In the first step, the addition of a carbanion $R^1R^2CH^-$ formed by reacting $R^1R^2CH_2$ with a strong base, with an ester $R^5$—C(=O)OR*, wherein R* is lower alkyl, produces an intermediate ketone $R^1R^2CH$—$CR^5$=O, which may in the second step be reacted with a suitable reducing agent, for example $NaBH_4$ or $NaBH_3CN$, to provide the compound of formula (A) wherein X=O, and one $R^5$ is H.

For example, when $R^1R^2CH_2$ is fluorene, this is reacted with a strong base, for example, to form a fluorenyl carbanion, which is then reacted with $R^5{}_2$—CO, the reaction is as follows:

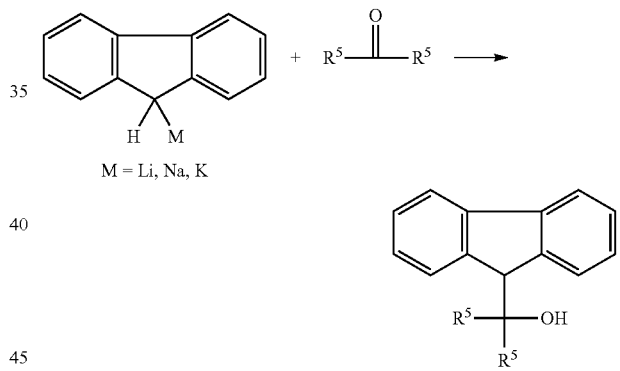

Corresponding compounds wherein x is S may be similarly prepared using the appropriate analogue $R^5{}_2$—C=S, or may alternatively be prepared by subsequent chemical transformation of formula (A) where x is O using methods known in the art, for example activation of the alcohol group in (A), for example by conversion to a bromide using $PBr_3$ or $Ph_3PBr_2$, or by conversion to the tosylate or triflate, and displacement by a suitable nucleophilic group such as thiourea or thiosulfate. In one embodiment, thiosulfate is used to form an intermediate that is hydrolyzed by acid treatment to form the thiol.

Compounds wherein m is 1 and both $R^5$ are H may be prepared by addition of the carbanion derived by lithiation of $R^1R^2CH_2$, for example using a strong base such as NaH, butyllithium, lithium bis(trimethyl-silylamide), or similar, to an unsaturated compound such as methyl 3-(dimethylamino)-acrylate to provide an intermediate ester, which may be reduced, either via one step or through multiple steps, to the corresponding unsaturated aldehyde:

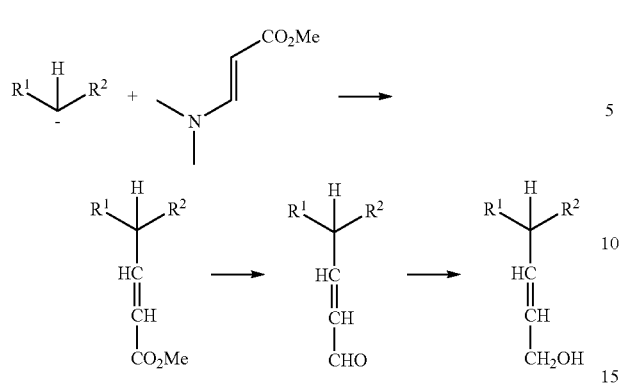

Reaction of the unsaturated aldehyde with a substituted or unsubstituted arylboronic acid, aryl-B(OH)$_2$, in the presence of a palladium catalyst, for example as described in *Org. Letts.* (2005) 7:4153-5, provides a compound wherein one $R^5$ is substituted aryl, one $R^5$ is H, and X=O.

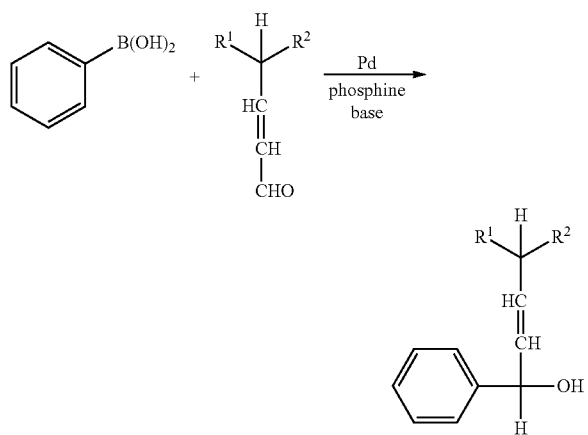

Alternatively, reaction of the unsaturated aldehyde with an alkylborane according to the method of Soderquist provides compounds wherein x=O, one $R^5$ is H and the other is CH$_2$CH=CH$_2$ or CH$_2$CCH. See Burgos, C. H., et al., *J. Am. Chem. Soc.* (2005) 127:8044.

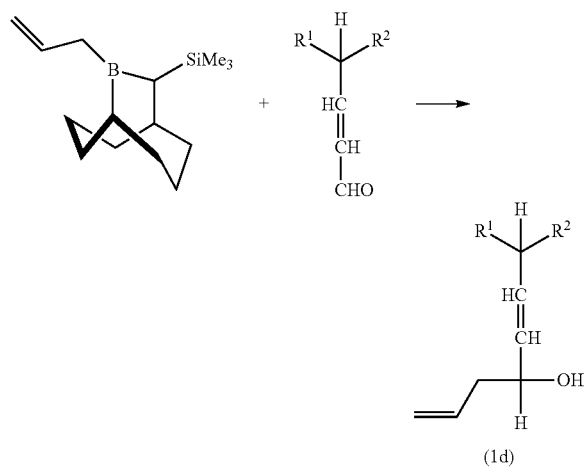

The compounds of formula (A) may then be derivatized to the drug. In these intermediates and the drug conjugate, all of the embodiments which correspond to the many illustrated forms of formulas (1) and (2), and specifically embodiments of $R^1$, $R^2$ and $R^5$ are retained.

In instances where Y is NBCH$_2$, an additional intermediate is prepared from the compound of formula (A), for example, by activating the compound of formula (A) where x is 0 to a chloroformate as described above and then further reacting this compound with hexahydrotriazine. This results in an intermediate where a leaving group coupled to the methylene is a halo group—i.e., Y—Cl, wherein Y is NBCH$_2$. This intermediate can be converted to an intermediate with a drug comprising OH, SH or a heterocyclic nitrogen group under anhydrous conditions in the presence of mild base. Suitable bases include tertiary amines such as triethyl amine. The reaction mixture may optionally include NaI or a tetraalkylammonium iodide to accelerate the reaction. Suitable solvents include any inert anhydrous solvent.

Attachment of Protective Polymers

The dendrimers may also include protective polymer (the most common example would be PEG, but other hydrophilic polymers could also be used).

In one approach, only a portion of the reactive sites on the derivatized dendrimer are provided with drug conjugate or polymer by controlling the stoichiometry of the coupling reaction and the remaining sites are then coupled to the other component.

Alternatively, pre-assembled units comprising a PEG, a releasable linker or drug conjugate or some combination of these units may be prepared. The pre-assembled units are then attached to the outer shell of the dendrimer, either in solution or while on a solid phase synthesis support. Such pre-assembled units may be constructed in a stepwise process starting from a trifunctional matrix molecule wherein each functionality may be selectively attached to a PEG, a releasable linker or drug conjugate, and to the dendrimer outer shell. Suitable functionalities include carboxylic acids, amines, maleimides, azides, thiols, and alkynes, which may be present in protected form.

For example, an amino acid comprising a carboxylic acid group and two differentially protected functional groups can be converted into such a pre-assembled unit by selective deprotection of one protected functional group, attachment of a PEG, then deprotection of the second protected functional group and attachment of the drug conjugate, then final attachment of the pre-assembled unit through the carboxylic acid to the dendrimer. In one example, azidonorleucine is reacted with an activated PEG molecule, for example a PEG N-hydroxysuccinimide carbonate, so as to produce $N_\alpha$-PEG-azidonorleucine. The $N_\alpha$-PEG-azidonorleucine is then either attached to the outer shell of the dendrimer through standard amide-forming reactions to provide a PEGylated dendrimer having an array of azide functionalities on the outer shell that can be subsequently coupled with alkynyl-linkers or alkynyl drug conjugate, or is first reacted with an alkynyl-linker or alkynyl-drug conjugate under Cu(I) catalysis to provide the complete pre-assembled unit, which is then attached to a dendrimer having amine groups on the outer shell using standard amide-forming reactions.

In another example, a protected cysteine, for example S-(monomethoxytrityl)-cysteine, is reacted with an activated PEG molecule, for example a PEG N-hydroxysuccinimide carbonate, so as to produce $N_\alpha$-PEG-S(mmt)-cysteine. This can be attached to a dendrimer having outer shell amines using standard amide forming reactions, and the resulting dendrimer can be detritylated using mild acid and the resulting thiols reacted with a maleimide-linker or maleimide-drug conjugate. Alternatively, the $N_\alpha$-PEG-S(mmt)-cysteine can be reacted with an amine-linker or amine-drug conjugate using standard amide-forming reactions, and the complete pre-assembled unit can be detritylated using mild acid and coupled to a dendrimer having maleimide groups on the outer shell.

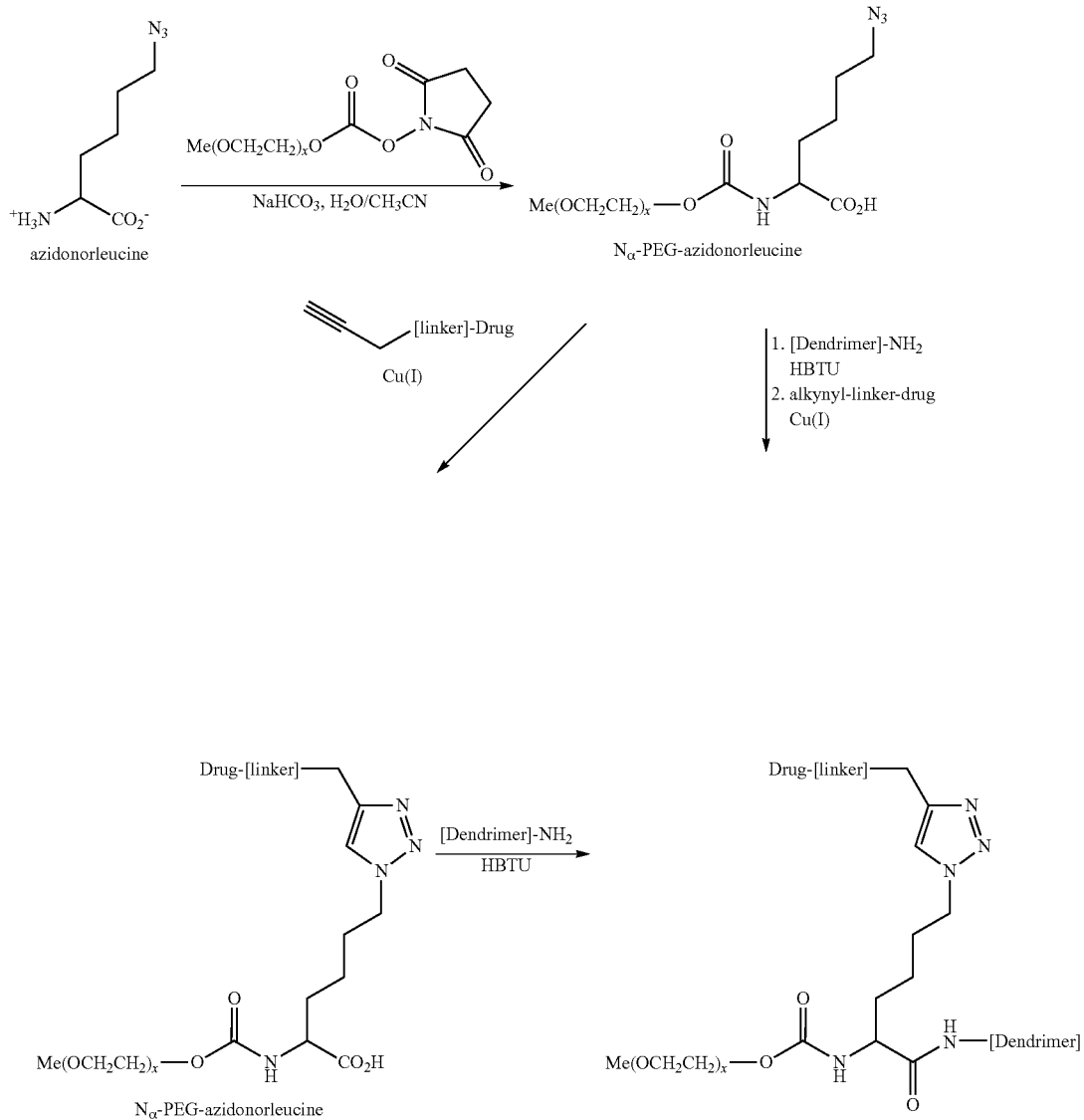

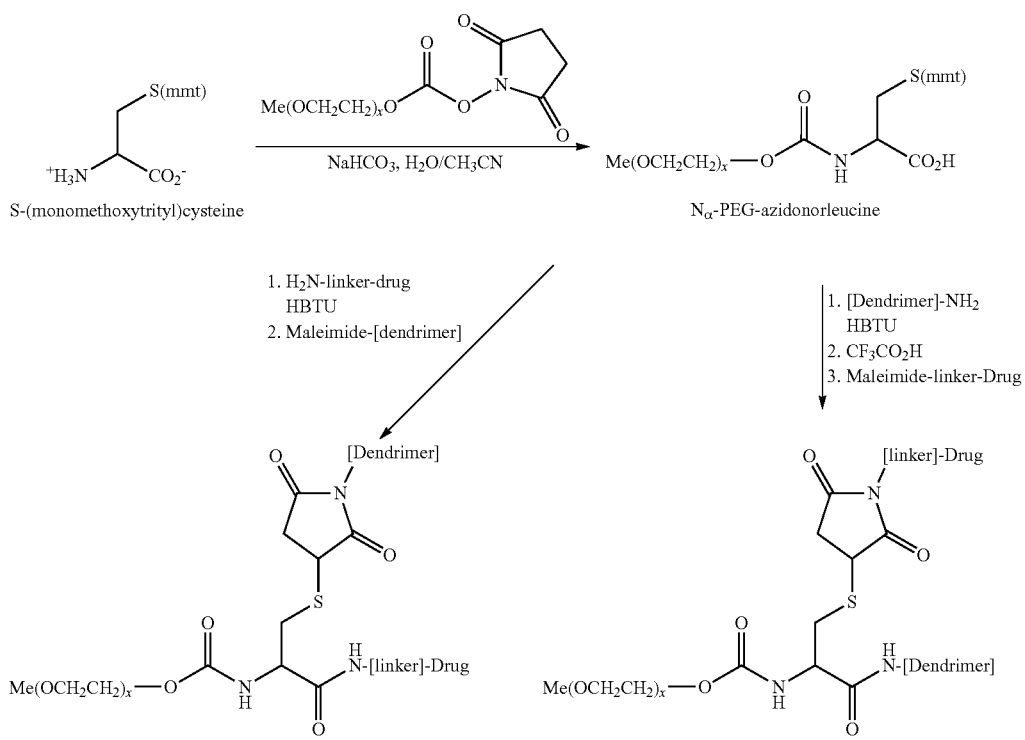

Administration and Use

The conjugates of the invention that are designed to release drugs at controllable rates are administered to subjects in a manner similar to medicaments in general. The subjects may be model systems such as mice, rats or rabbits or may be human patients or may be veterinary subjects such as companion animals, livestock, and avian subjects. The conjugates of the invention are typically administered by injection, in general by intravenous injection, but other dosage mechanisms are also within the scope of the invention such as oral administration, administration by suppository, transdermal or transmucosal administration and the like. The dosage levels will depend on the nature of the drug, the condition to be treated, the nature of the subject, and the judgment of the attending professional. The selection of appropriate release rates for a particular drug or protocol are also dependent on these factors. Thus, the use and administration of the compounds of the invention is within the skill of the practitioner. Further, as noted above, the conjugates of the invention are particularly useful and advantageous in treating diseases of the lymph system wherein subcutaneous injection is preferred.

The following examples are intended to illustrate but not to limit the invention.

Preparation 1

Release Rate Determination—Phenyl Sulfones

A series of model linker scaffolds having a range of functional groups as potential pKa modulators (substituted aromatics, ketones, nitriles, sulfones) were designed, prepared and linked via carbamate bonds to $N_\varepsilon$-2,4-dinitrophenyl-L-lysine ($N_\varepsilon$-DNP-Lys) for evaluation of release rates; DNP-Lys is water soluble and is a strong chromophore to permit HPLC-UV analysis. Rates of release at pH 7.4 and/or 8.3 were determined.

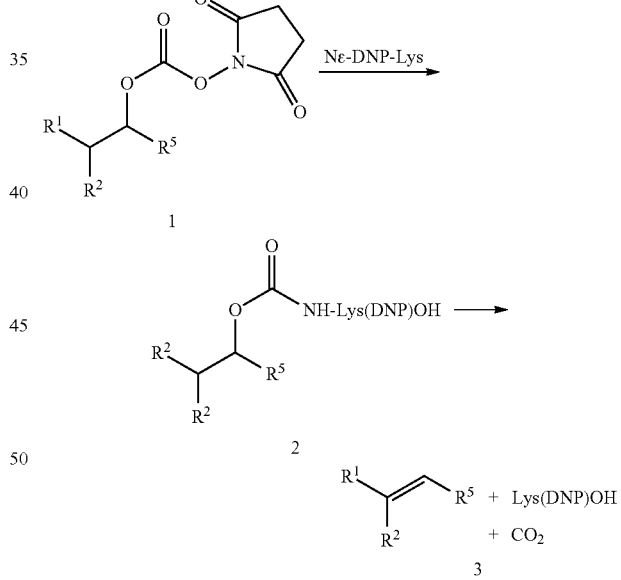

Starting alcohols, obtained commercially or prepared by standard methods, were converted into N-hydroxysuccinimide (HS) carbonates either using a one-step procedure with disuccinimidyl carbonate (Manoharan, *J. Org. Chem.* (1999) 64:6468-6472) or by a two-step procedure wherein the alcohol is first converted into the chloroformate using triphosgene/pyridine and then to the carbonate by treatment with N—HS (Tsubery, H., et al., *J. Biol. Chem.* (2004) 279:38118-38124).

The DNP carbamates were prepared as follows. A suspension of N-DNP-L-Lys HCl (35 mg, 0.1 mmol) in 600 µL of water was treated successively with 1.0 N NaOH (200 µL) and 1.0 M NaHCO$_3$. A 0.1 M solution of the N—HS carbonate in acetonitrile (1.0 mL) was added to the stirred mixture to give a clear yellow solution. After 1 hr, the mixture was diluted with 10 mL water and loaded onto a Bond-Elut™ C18 extraction column (1 gm). The column was washed successively with water, 1% CF$_3$CO$_2$H/water, water, and 50% MeOH/water. The product was eluted with MeOH, then evaporated to give the product as a yellow glass. Kinetic analyses were performed by HPLC (C18; linear MeOH/water+0.5% HOAc gradient) using a UV/vis monitor. The areas under the DNP and starting material peaks were integrated to determine extent of reaction.

The $t_{1/2}$ values of β-eliminative cleavage of DNP-Lys carbamates at pH 7.4 and/or 8.3 are shown in Table 4.

TABLE 4

| $R^1$ | $R^2$ | $R^5$ | $t_{1/2}$ pH 7.4 | $t_{1/2}$ pH 8.3 |
|---|---|---|---|---|
| 4-MePhSO$_2$ | H | H | 56 hrs | — |
| PhSO$_2$ | H | H | 30 hrs | — |
| 3-NO$_2$PhSO$_2$ | H | H | 2 hrs | — |
| PhSO$_2$ | H | Me | 72 hrs | — |
| 4-ClPhSO$_2$ | H | Me | 46 hrs | — |
| 4-ClPhSO$_2$ | H | 4-OMePh | 18 hrs | — |
| 4-ClPhSO$_2$ | H | 4-BrPh | 17 hrs | — |
| 4-ClPhSO$_2$ | H | 4-NO$_2$Ph | 2 hrs | — |
| 4-OMePhSO$_2$ | H | 3-NO$_2$Ph | 13 hrs | — |
| 4-OMePhSO$_2$ | H | 4-NO$_2$Ph | 10 hrs | — |
| CN | H | H | — | 160 hrs |
| CN | H | Me | — | 320 hrs |
| CN | H | Ph | — | 98 hrs |
| CN | H | 4-BrPh | 270 hrs | — |
| CN | H | 4-OMePh | 22 hrs | — |
| CN | 4-OMePh | Me | 125 hrs | — |
| CN | 4-NO$_2$Ph | Me | ~80 hrs | — |
| 9-fluorenyl | | H | ~1650 hrs | 200 hrs |
| 9-fluorenyl | | Me | — | ~1800 hrs |
| 9-fluorenyl | | 4-BrPh | — | 285 hrs |

The half-lives for cleavage span 2 hr to >10 days. That cleavage was generated by β-eliminative reactions was evidenced by the different half-lives, and determination that O-benzyl-N—(N$_e$-2,4-DNP-Lys) carbamate (which cannot undergo O-alkyl scission) showed less than 0.25% cleavage after 5 days at 37° C. and pH 7.4 ($t_{1/2}$>3 yrs). O-benzyl-N—(N$_e$-2,4-DNP-Lys) carbamate undergoes no detectable hydrolysis in 50% human serum after 1 week at 37° C. This demonstrates the stability of carbamates to serum hydrolases. In general, compared to C—H, a) electron withdrawing groups at $R^1$ increase the rate; b) alkyl groups at $R^3$ increase the rate; and c) aryl moieties at $R^3$ decrease the rate.

A good linear free energy relationship, shown in FIG. 5, was observed for the substituted (phenylsulfonyl)ethyl linkers, allowing estimation of release rates for other substituted linkers in this series based on SAR using Hammett sigma parameters, for the substituents on the phenyl group as shown. Thus, substituents can be selected to provide either slower (e.g., 4-OMe, $\sigma_p$=−0.27; 4-OH, $\sigma_p$=−0.37; 4-Me$_2$N, $\sigma_p$=−0.83) or intermediate release rates (e.g., 4-F, $\sigma_p$=+0.06; 4-Cl, $\sigma_p$=+0.23; 3-Br, $\sigma_m$=+0.39; 4-CF$_3$, $\sigma_p$=+0.54).

Preparation 2

Release Rate Determination—Effect of $R^5$

From the studies in Preparation 1, the phenyl sulfone moieties at $R^1$ appeared to provide rates ($t_{1/2}$~2 to 72 hr) spanning a range suitable for use in our conjugates. These were converted into bifunctional linkers containing a N—HS carbonate for attachment to amine-containing molecules and an acylated 3-aminophenyl moiety at $R^5$ for attachment to PEG, or to dendrimers. In particular, linkers having the general structure shown below were prepared.

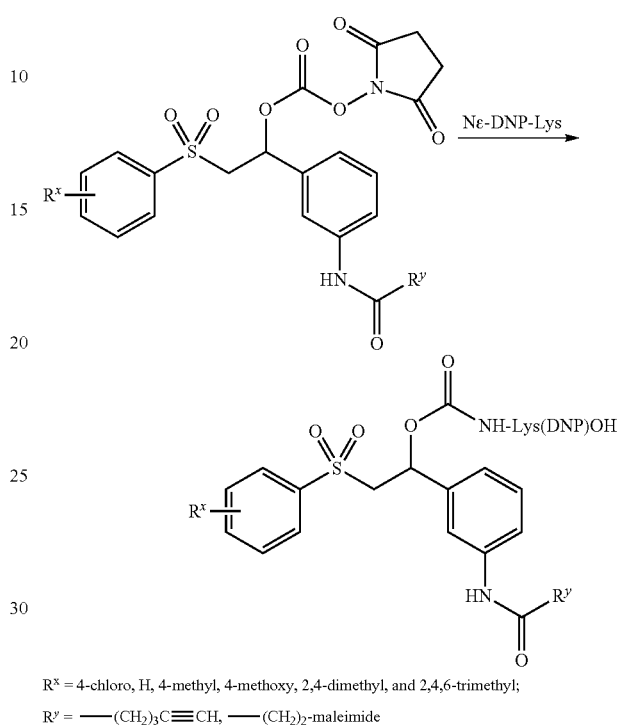

$R^x$ = 4-chloro, H, 4-methyl, 4-methoxy, 2,4-dimethyl, and 2,4,6-trimethyl;

$R^y$ = —(CH$_2$)$_3$C≡CH, —(CH$_2$)$_2$-maleimide

The N—HS carbonate linkers with $R^y$=—(CH$_2$)$_3$C≡CH were attached to N$_e$-DNP-Lys, and the rates of Lys(DNP) release were measured in 0.1 M HEPES, pH 7.40 at 25° C. or 37° C. using HPLC. All compounds gave good first-order kinetics, with $t_{1/2}$ 16 to 120 hours (Table 5) and a temperature coefficient $Q_{12}$ of 5.7±0.1.

TABLE 5

| Rates of H-Lys(DNP)-OH release from compounds ($R^y$ = —(CH$_2$)$_3$C≡CH) | | | | | |
|---|---|---|---|---|---|
| | | k, hr$^{-1}$ | | $t_{1/2}$, hr | |
| No. | $R^1$ | 25° C. | 37° C. | 25° C. | 37° C. |
| 1 | 4-Cl | 0.0074 | 0.0434 | 94 | 16 |
| 2 | H | 0.004 | 0.0236 | 170 | 30 |
| 3 | 2,4-Me$_2$ | 0.0021 | 0.012* | 330 | 57 |
| 4 | 4-Me | 0.0018 | 0.0104* | 380 | 67 |
| 5 | 4-OMe | 0.0013 | 0.0074 | 530 | 94 |
| 6 | 2,4,6-Me$_3$ | 0.001 | 0.0057 | 690 | 120 |

*extrapolated from data at 25° C.

Figure 6:
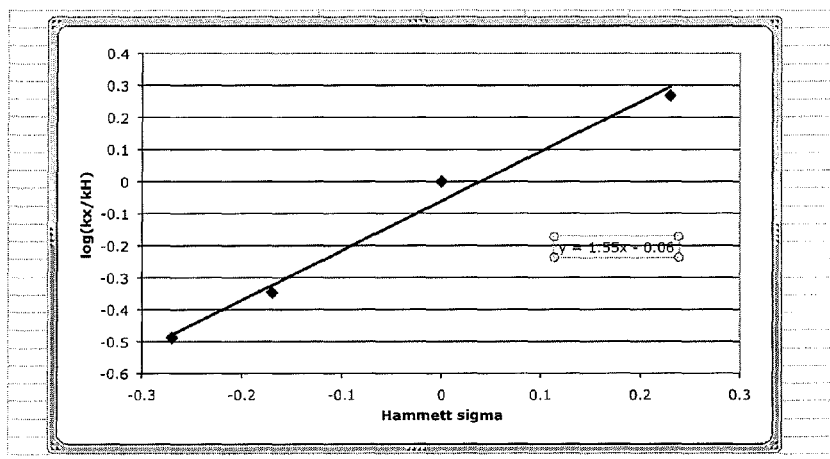
FIG. 6 is a graph showing the free energy correlation between Hammett sigma values and rate of release of label by β-elimination.

A good correlation between release rate and Hammett sigma constants was also observed for the mono-substituted compounds is shown in FIG. 6.

Preparation 3

Effect of Coupling to a Macromolecule

The linker with $R^x$=4-methoxy, $R^y$=—(CH$_2$)$_3$C≡CH coupled to N$_e$-DNP-Lys was conjugated with 40 kDa PEG-azide using copper-catalyzed Huisgen cycloaddition. Examination of the release of H-Lys(DNP)—OH indicated that the rate of release from the macromolecular conjugate (k=0.0059 h$^{-1}$, t$_{1/2}$=118 hrs) was similar to that of the unconjugated linker (t$_{1/2}$=94 hr).

Preliminary results of determination of effects of human sera on the rate of release from PEG-conjugates suggest there may be a uniform 3-fold rate enhancement of cleavage. The conjugate of 40 kDa PEG with this compound was administered to rats to determine pharmacokinetics; stably conjugated Lys(DNP) was also prepared by click chemistry between Na-hexynoyl-Lys(DNP)—OH and 40 kDa-PEG-azide and administered to rats as a control. Competitive ELISA for DNP-Lys using DNP—BSA and an anti-DNP antibody conjugated to alkaline phosphatase is employed.

Preparations 4-19 describe intermediates and compounds of formula (3), not yet linked to dendrimer, i.e., compounds wherein X is O and Y is NBCH$_2$ wherein the CH$_2$ group is coupled to a nucleofuge. In Preparation 19, the nucleofuge is replaced by a model system permitting monitoring release of cysteine coupled to 4-dinitrophenyl.

Preparation 4

General Preparation of Chloroformates and N-Hydroxysuccinimide Carbonates

Pyridine (0.33 equivalent) is added dropwise to a vigorously stirred solution of the alcohol (1 equivalent) and triphosgene (0.33 equivalent) in anhydrous tetrahydrofuran (2 mL/mmol) cooled on ice. After 1 hr, the mixture is allowed to warm to ambient temperature and kept overnight. The mix is then filtered and concentrated under vacuum on a rotary evaporator. The resulting crude chloroformate is used without further purification.

To prepare N-hydroxysuccinimide carbonates, the crude chloroformate is dissolved in anhydrous tetrahydrofuran (2 mL/mmol) and treated with pyridine (2 equivalents) and N-hydroxysuccinimide (4 equivalents) at ambient temperature for 30 minutes. The mixture is diluted with ethyl acetate, washed successively with 0.1 N HCl, water, and brine, then dried over MgSO$_4$, filtered, and evaporated. The crude carbonates are purified by silica gel chromatography (ethyl acetate/hexane).

Preparation 5

General Preparation of Carbamates

A solution of the chloroformate (1 equivalent) in acetone (2 mL/mmol) is added dropwise to a vigorously stirred mixture of the amine or aniline (1 equivalent) and NaHCO$_3$ (2 equivalents) in water (2 mL/mmol). After 30 minutes, carbamates which precipitate as solids are collected by vacuum filtration, washed with water, and dried; carbamates which separate as oils are extracted with ethyl acetate. The extract is dried over MgSO$_4$, filtered, and evaporated to provide the crude carbamate. In either case, the crude carbamate is further purified by column chromatography (SiO$_2$) or by crystallization.

Alternatively, triethylamine (1 equivalent) is added to a mixture of the amine or aniline (1 equivalent) and the chloroformate (1 equivalent) in an inert anhydrous solvent, for example dichloromethane, tetrahydrofuran, or ethyl acetate. After stirring for 1 h at ambient temperature, the mixture is evaporated to dryness, and the residue is dissolved in ethyl acetate and washed successively with 1 N HCl, water, sat. aq. NaHCO$_3$, and brine, then dried over MgSO$_4$, filtered, and evaporated to provide the crude carbamate, which is purified as described above.

Alternatively, an alcohol is converted to a carbamate without isolation of the intermediate chloroformate. Pyridine (0.33 equivalent) is added dropwise to a vigorously stirred solution of the alcohol (1 equivalent) and triphosgene (0.33 equivalent) in anhydrous tetrahydrofuran (2 mL/mmol) cooled on ice. After 1 hr, the mixture is allowed to warm to ambient temperature and kept overnight. The mixture is cooled on ice, and the amine or aniline (2 equivalents) is added. The mixture is allowed to warm to ambient temperature and kept overnight. The mixture is then evaporated to dryness, and the residue is dissolved in ethyl acetate and washed successively with 1 N HCl, water, sat. aq. NaHCO$_3$, and brine, then dried over MgSO$_4$, filtered, and evaporated to provide the crude carbamate, which is purified as described above.

Preparation 6

N-Chloromethylation of Carbamates

A mixture of the carbamate (1 equivalent) and paraformaldehyde (3 equivalents of formaldehyde) in 1:1 tetrahydrofuran/chlorotrimethylsilane (1 mL/mmol) in a sealed screw-cap vial is heated at 55° C. until a clear solution is obtained. The mixture is concentrated under vacuum on a rotary evaporator, and the residue is dissolved in ethyl acetate, filtered, and concentrated again to provide the crude N-chloromethyl carbamate.

Preparation 7

N-Methoxymethyl Carbamates

A solution of N-chloromethyl carbamate in methanol is allowed to stand at ambient temperature for 1 h, then concentrated to dryness to provide the N-methoxymethyl carbamate.

Preparation 8

N-Alkoxymethyl Carbamates, N-Phenoxymethyl Carbamates, N-Thiomethyl Carbamates, and N-Thiophenylmethyl Carbamates A solution of the alcohol, phenol, thiol, or thiophenol (1 equivalent) and the N-chloromethylcarbamate (1 equivalent) in an inert anhydrous solvent, for example tetrahydrofuran, dichloromethane, or ethyl acetate, is treated dropwise with triethylamine (1 equivalent). After 1 hour, the mixture is evaporated to dryness. The crude product is purified by silica gel chromatography.

Preparation 9

O-(9-Fluorenylmethyl)-N-Phenyl Carbamate

A solution of 9-fluorenylmethoxycarbonyl chloride (2.6 g) in 20 mL of acetone was added slowly to a stirred mixture of aniline (0.93 g) and NaHCO$_3$ (2.5 g) in 20 mL of water. After 1 hour, the solid precipitate was collected by vacuum filtration, washed with water, and air dried. Crystallization from ethyl acetate provided the product.

Preparation 10

O-(9-Fluorenylmethyl)-N-Propargyl Carbamate

A solution of 9-fluorenylmethoxycarbonyl chloride (2.6 g) in 20 mL of acetone was added slowly to a stirred mixture of propargylamine hydrochloride (0.91 g) and NaHCO$_3$ (2.5 g) in 20 mL of water. After 1 hour, the solid precipitate was collected by vacuum filtration, washed with water, and air dried. Crystallization from ethyl acetate/hexane provided the product.

Preparation 11

O-(9-Fluorenylmethyl)N-(4-Bromophenyl)Carbamate

Triethylamine (0.7 mL) was added to a stirred mixture of 4-bromoaniline (0.85 g) and 9-fluorenylmethoxycarbonyl chloride (1.3 g) in 25 mL of dichloromethane. The mixture was stirred for 1 h at ambient temperature, then washed with 1 N HCl, water, sat. aq. NaHCO$_3$, and brine. The organic solution was dried over MgSO$_4$, filtered, and evaporated.

Preparation 12

O-(9-Fluorenylmethyl)N-(4-(Ethoxycarbonyl)Phenyl)Carbamate

Triethylamine (0.7 mL) was added to a stirred mixture of ethyl 4-aminobenzoate (0.85 g) and 9-fluorenylmethoxycarbonyl chloride (1.3 g) in 25 mL of dichloromethane. The mixture was stirred for 1 h at ambient temperature, then washed with 1 N HCl, water, sat. aq. NaHCO$_3$, and brine. The organic solution was dried over MgSO$_4$, filtered, and evaporated.

Preparation 13

O-(9-Fluorenylmethyl)-N-Propyl Carbamate

A solution of 9-fluorenylmethoxycarbonyl chloride (2.6 g) in 20 mL of acetone was added slowly to a stirred mixture of propylamine hydrochloride (0.91 g) and NaHCO$_3$ (2.5 g) in 20 mL of water. After 1 hour, the solid precipitate was collected by vacuum filtration, washed with water, and air dried. Crystallization from ethyl acetate/hexane provided the product.

Preparation 14

O-Ethyl N-Phenyl Carbamate

A solution of ethyl chloroformate (1.1 g) in 20 mL of acetone was added slowly to a stirred mixture of aniline (0.93 g) and NaHCO$_3$ (2.5 g) in 20 mL of water. After 1 hour, the mixture was extracted with ethyl acetate. The extract was dried over MgSO$_4$, filtered, and evaporated to provide the crude product as an oil that slowly crystallized upon standing. Crystallization from ethyl acetate/hexane provided the product.

Preparation 15

O-(2-(Phenylsulfonyl)Ethyl)N-Phenyl Carbamate

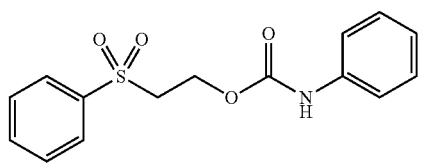 [SMILES: O=C(Nc1ccccc1)OCCS(=O)(=O)c1ccccc1]

Pyridine (0.86 mL) was added to a solution of 2-(phenylsulfonyl)ethanol (1.0 g) and triphosgene (2.2 g) in anhydrous tetrahydrofuran (10 mL). After stirring for 30 min, the mixture was filtered and evaporated to an oil under vacuum to provide 0.93 g of the crude chloroformate. The chloroformate was redissolved in 10 mL of acetone and added to a mixture of aniline (0.37 g) and NaHCO$_3$ (0.42 g) in 10 mL of water. Ethyl acetate (5 mL) was added, and after 1 hour, the organic phase was collected, dried over MgSO$_4$, filtered, and evaporated to provide the 1.1 g of the crude product as an orange oil. Crystallized from 1:1 ethyl acetate/hexane.

Preparation 16

O-(9-Fluorenylmethyl)N-Phenyl N-Chloromethyl Carbamate

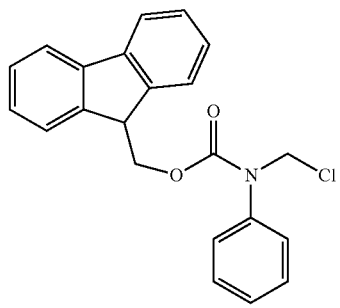 [SMILES: O=C(OCC1c2ccccc2-c2ccccc21)N(CCl)c1ccccc1]

A suspension of O-(9-fluorenylmethyl)N-phenyl carbamate (1.58 g), paraformaldehyde (0.25 g), chlorotrimethylsilane (5 mL) and tetrahydrofuran (5 mL) was heated at 55° C. in a sealed vial for 20 h. The resulting clear solution was concentrated to an oil using a rotary evaporator. The residue was dissolved in ethyl acetate and re-concentrated, resulting in crystallization. The crystals were suspended in 2:1 hexane/ethyl acetate, collected, and dried to provide 1.45 g of the N-chloromethyl carbamate.

Preparation 17

O-(9-Fluorenylmethyl)N-Phenyl N-Methoxymethyl Carbamate

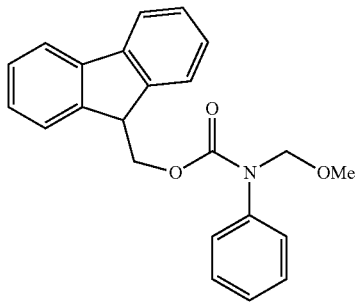 [SMILES: COCN(C(=O)OCC1c2ccccc2-c2ccccc21)c1ccccc1]

Prepared by dissolving O-(9-fluorenylmethyl)N-phenyl N-chloromethyl carbamate (Preparation 14) in methanol. ¹H-NMR (d6-DMSO) δ 7.86 (2H, d, J=7 Hz), 7.42-7.22 (m, 9H), 7.14 (m, 2H), 4.83 (2H, br s), 4.47 (2H, d, J=6 Hz), 4.18 (1H, m), 3.11 (3H, br s).

Preparation 18

N-(2,4-Dinitrophenyl)Cysteine Allyl Ester

Step 1. A solution of cystine bis(allyl ester) p-toluenesulfonate and 2,4-dinitrofluorobenzene in THF was treated with triethylamine for 24 hrs. The mixture was diluted with ethyl acetate, washed successively with 1 N HCl, water, sat. aq. NaHCO₃, and brine, then dried over MgSO₄, filtered, and evaporated to provide bis(N-DNP)-cystine bis(allyl ester).

Step 2. A solution of bis(N-DNP)-cystine bis(allyl ester) (326 mg) in THF (2 mL) was treated with a solution of dithiothreitol (115 mg) in water (1 mL), followed by addition of 1 M NaHCO₃ (50 μL). The bright yellow mixture immediately turned dark. After 15 minutes, the mixture was diluted with 10 mL of water and acidified with 1 N HCl (50 μL), then extracted with ethyl acetate. The extract was washed with water and brine. The yellow solution was over MgSO₄, filtered, and evaporated to provide crude N-DNP-cysteine allyl ester. The crude material was dissolved in dichloromethane and filtered through 5 mL of silica gel using 1:1 ethyl acetate/hexane to elute the bright yellow product (371 mg).

Preparation 19

S—(N-(9-Fluorenylmethoxycarbonyl-N-Phenylamino)Methyl)N-(2,4-Dinitrophenyl)-Cysteine

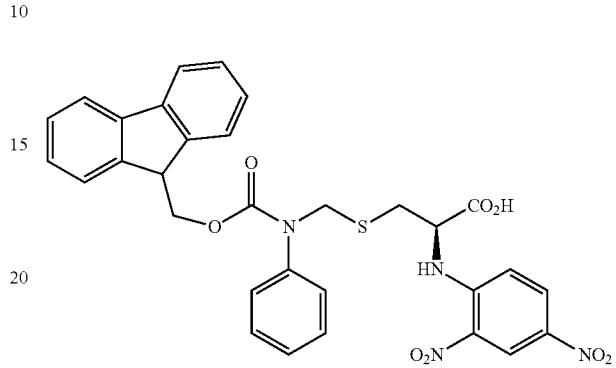

A solution of N-(DNP)-cysteine allyl ester of Preparation 18 (82 mg) and O-(9-fluorenylmethyl)N-phenyl N-chloromethyl carbamate of Preparation 16 (91 mg) in dichloromethane (1 mL) was treated with triethylamine (35 μL) for 1 hour, then filtered through silica gel using 1:1 ethyl acetate/hexane and concentrated to dryness. The product was purified by silica gel chromatography.

A solution of the allyl ester, phenylsilane (75 μL), and tetrakis(triphenylphosphine)palladium (15 mg) in THF (2.5 mL) was stirred at ambient temperature for 10 minutes, then evaporated to dryness. The residue was dissolved in dichloromethane and loaded onto a 5 mL column of silica gel, which was eluted sequentially with 1:4 ethyl acetate/hexane, ethyl acetate, and 0.5% acetic acid/ethyl acetate. Fractions containing product were combined and evaporated.

¹H-NMR (d6-DMSO): d 13.7 (1H, br s), 9.01 (1H, d, J=7 Hz), 8.85 (1H, d, J=3 Hz), 8.25 (1H, dd, J=3, 9 Hz), 7.82 (1H, d, J=7), 7.40-7.25 (m, 7H), 7.25-7.15 (m, 3H), 7.11 (m, 2H), 4.96 (m, 1H), 4.81 (s, 2H), 4.30 (m, 2H), 4.08 (m, 1H), 3.18 (m, 2H).

Preparations 20-22 describe intermediates and compounds of formula (3) not yet linked to dendrimer, i.e., compounds wherein X is O and Y is NBCH₂, wherein the methylene group is coupled to the OH group of a serine residue.

Preparation 20

N-(6-(2,4-Dinitrophenylamino)Hexanoyl-L-Serine Allyl Ester

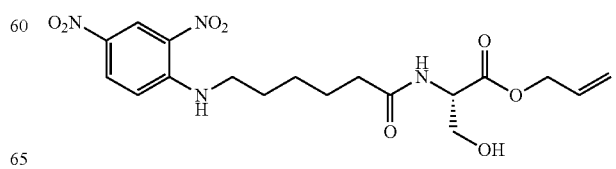

Step 1. N-(tert-butoxycarbonyl)-L-serine allyl ester: To a stirred solution of allyl bromide (2.3 mL, 26.6 mmol) and tricaprymethylammonium chloride (4.00 g, 9.90 mmol) in $CH_2Cl_2$ (35 mL) was added a solution of N-(tert-butoxycarbonyl)-L-serine (1.03 g, 5.02 mmol) and $NaHCO_3$ (0.43 g, 5.12 mmol) in water (16 mL). The biphasic reaction mixture was vigorously stirred at room temperature for 48 hours. It was diluted with water (50 mL) and extracted with $CH_2Cl_2$ (3×50 mL). The combined organic extracts were dried over $MgSO_4$, filtered, and concentrated under reduced pressure to yield a colorless oil (5.95 g). Purification using a Thomson Instruments Single Step 80 g silica gel cartridge eluting with 60% hexanes/40% ethyl acetate produced LR2-1 (1.01 g, 82%) as a colorless oil. $^1$H NMR (DMSO-d6) δ 1.37 (9H, s), 3.63 (2H, m), 4.00 (2H, m), 4.53 (2H, m), 4.89 (1H, t, J=6.2 Hz), 5.18 (1H, dd, J=1.4 Hz, J=10.6 Hz), 5.30 (1H, dd, J=1.6 Hz, J=17.1 Hz), 5.84 (1H, m), 6.98 (1H, d, J=8.2 Hz).

Step 2. A solution of N-(tert-butoxycarbonyl)-L-serine allyl ester (0.175 g, 0.731 mmol) in 4 M hydrogen chloride/dioxane (2 mL) was stirred at ambient temperature for 40 minutes. The reaction mixture was concentrated on a rotary evaporator and the crude HCl salt was taken up in anhydrous tetrahydrofuran (3 mL). To this solution was added N-succinimidyl 6-(2,4-dinitroanilino)hexanoate (0.288 g, 0.791 mmol) and triethylamine (102 mL, 0.731 mmol). The reaction mixture was stirred at room temperature for 30 minutes and the solvent was evaporated. The residue was partitioned between ethyl acetate and water and the phases were separated. The organic phase was washed with saturated $NaHCO_3$ and saturated NaCl. It was dried over $MgSO_4$, filtered, and concentrated under reduced pressure to yield the crude product (0.293 g) as a yellow oil. Purification using a Thomson Instruments Single Step 12 g silica gel cartridge eluting with 50% hexanes/50% ethyl acetate followed by ethyl acetate gave the product (0.222 g, 72%) as a yellow oil. $^1$H NMR (DMSO-d6) δ 1.32 (2H, m), 1.52-1.64 (4H, m), 2.15 (2H, t, J=7.0 Hz), 3.44 (2H, m), 3.59 (1H, m), 3.66 (1H, m), 4.33 (1H, m), 4.55 (2H, m), 5.02 (1H, t, J=5.5 Hz), 5.17 (1H, m), 5.28 (1H, m), 5.83 (1H, m), 7.21 (1H, d, J=9.5 Hz), 8.12 (1H, d, J=7.9 Hz), 8.23 (1H, dd, J=2.5 Hz, J=9.4 Hz), 8.85 (2H, m).

Preparation 21

O—(N-((9-Fluorenylmethoxy)Carbonyl)-N-Phenyl)Aminomethyl)N-(6-(2,4-Dinitrophenylamino)Hexanoyl)-Serine Step 1. A solution of N-(6-(2,4-dinitrophenylamino)hexanoyl-L-serine allyl ester (0.050 g, 0.118 mmol), O-(9-fluorenylmethyl)N-phenyl N-chloromethyl carbamate (0.043 g, 0.118 mmol) and triethylamine (16.1 mL, 0.116 mmol) in anhydrous $CH_2Cl_2$ (2 mL) was heated at reflux for 1 hour. Further aliquots of O-(9-fluorenylmethyl)N-phenyl N-chloromethyl carbamate (0.043 g, 0.118 mmol) and triethylamine (16.1 mL, 0.116 mmol) were added and reflux maintained for 1 hour. The solution was cooled to room temperature, diluted with $CH_2Cl_2$, washed with saturated NaCl solution, dried over $MgSO_4$, filtered, and concentrated under reduced pressure. The crude material (0.145 g) was purified using a Thomson Instruments Single Step 12 g silica gel cartridge eluting with 50% hexanes/50% ethyl acetate followed by 30% hexanes/70% ethyl acetate to furnish the intermediate allyl ester (0.030 g, 33%) as a yellow oil. $^1$H NMR (DMSO-d6) δ 1.31 (2H, m), 1.52-1.63 (4H, m), 2.15 (2H, t, J=7.3 Hz), 3.41 (2H, m), 3.43-3.70 (211, br. m), 4.15 (1H, br, m), 4.43-4.54 (5H, br. m), 4.87 (2H, br. m), 5.14 (1H, m), 5.25 (1H, m), 5.79 (1H, m), 7.12-7.38 (12, m), 7.82 (2H, d, J=7.4 Hz), 8.21 (1H, dd, J=2.5 Hz), J=9.5 Hz), 8.25 (1H, d, J=8.0 Hz), 8.84 (2H, m).

Step 2. Tetrakis(triphenylphoshine)palladium(0) (0.002 g, 1.7 μmol) was added to a stirred solution of the allyl ester from Step 1 (0.030 g, 40 μmol) and phenylsilane (9.8 mL, 80 mop in anhydrous tetrahydrofuran (0.5 mL). The reaction mixture was stirred at ambient temperature for 30 minutes and was then concentrated. Silica gel and $CH_2Cl_2$ were added and the mixture again concentrated and loaded onto a short silica gel column. The column was eluted with 30% hexanes/70% ethyl acetate followed by ethyl acetate and finally ethyl acetate containing 0.5% acetic acid to generate the carboxylic acid (0.024 g, 86%) as a yellow oil. $^1$H NMR (DMSO-d6) δ 1.31 (2H, m), 1.51-1.62 (4H, m), 2.14 (2H, t, J=7.3 Hz), 3.40 (2H, m), 3.45-3.80 (2H, br. m), 4.14 (1H, br. m), 4.41 (3H, br. m), 4.87 (2H, br. m), 7.16-7.30 (12H, m), 7.82 (2H, d, J=7.6 Hz), 8.08 (1H, d, J=8.1 Hz), 8.20 (1H, dd, J=2.7 Hz, J=9.6 Hz), 8.83 (2H, m).

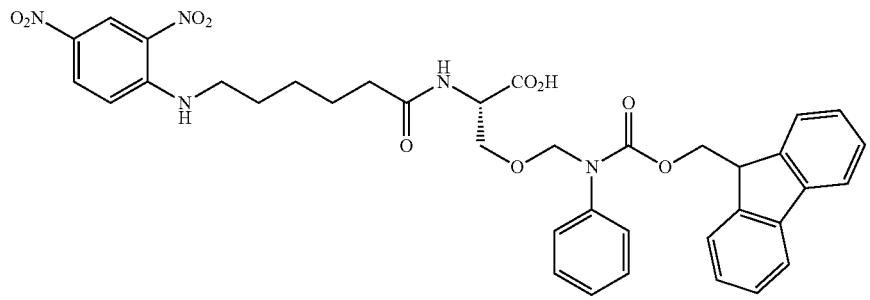 [SMILES: O=C(CCCCCNc1ccc([N+](=O)[O-])cc1[N+](=O)[O-])N[C@@H](COCN(C(=O)OCC1c2ccccc2-c2ccccc21)c1ccccc1)C(=O)O]

Preparation 22

O—(N-Ethoxycarbonyl-N-Phenyl)Aminomethyl)N-(6-(2,4-Dinitrophenylamino)Hexanoyl)-Serine

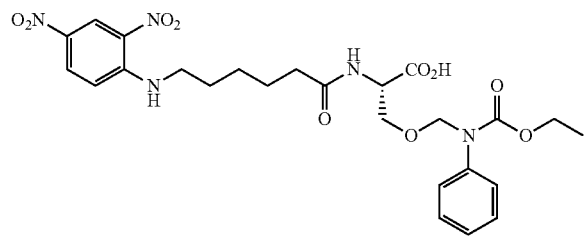 [SMILES: CCOC(=O)N(COC[C@H](NC(=O)CCCCCNc1ccc([N+](=O)[O-])cc1[N+](=O)[O-])C(=O)O)c1ccccc1]

Prepared in two steps as described in Preparation 21 above but utilizing O-ethyl N-phenyl N-chloromethyl carbamate as the alkylating agent in step 1. $^1$H NMR (DMSO-$d_6$) δ 1.13 (3H, t, J=7.0 Hz), 1.31 (2H, m), 1.51-1.63 (4H, m), 2.14 (2H, t, J=7.3 Hz), 3.42 (2H, q, J=6.7 Hz), 3.68 (1H, dd, J=4.2 Hz, J=9.7 Hz), 3.79 (1H, dd, J=5.7 Hz, J=9.7 Hz), 4.07 (2H, q, J=7.1 Hz), 4.42 (1H, m), 4.94 (1H, d, J=11.0 Hz), 5.01 (1H, d, J=11.0 Hz), 7.19-7.37 (6H, m), 8.10 (1H, d, J=8.2 Hz), 8.23 (1H, dd, J=2.7 Hz, J=9.7 Hz), 8.84 (2H, m), 12.75 (1H, br. s).

Preparations 23 and 24 together describe constructs of the invention wherein Y is NBCH$_2$ and the linker for binding to dendrimer is coupled to R$^1$. The construct includes the drug SN38 which provides a hydroxyl group for binding to the CH$_2$ of the adaptor.

Preparation 23

O-((9-(2-(N-(6-Azidohexanoyl)N-Methyl)Aminomethyl)Fluorenyl)Methyl)N-Phenyl N-Chloromethyl Carbamate

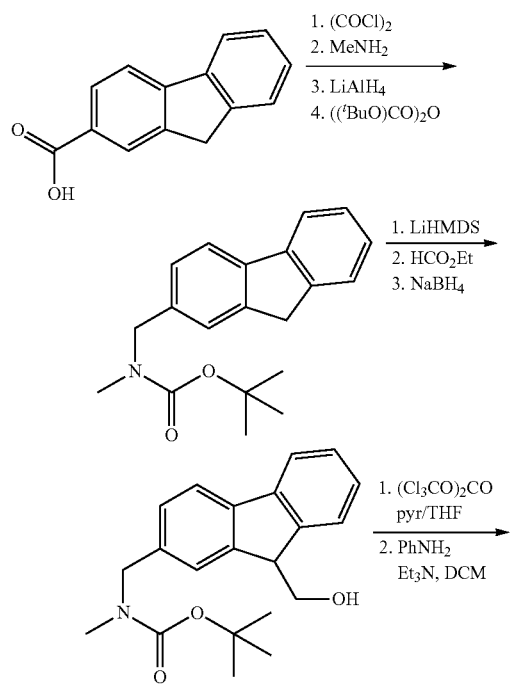

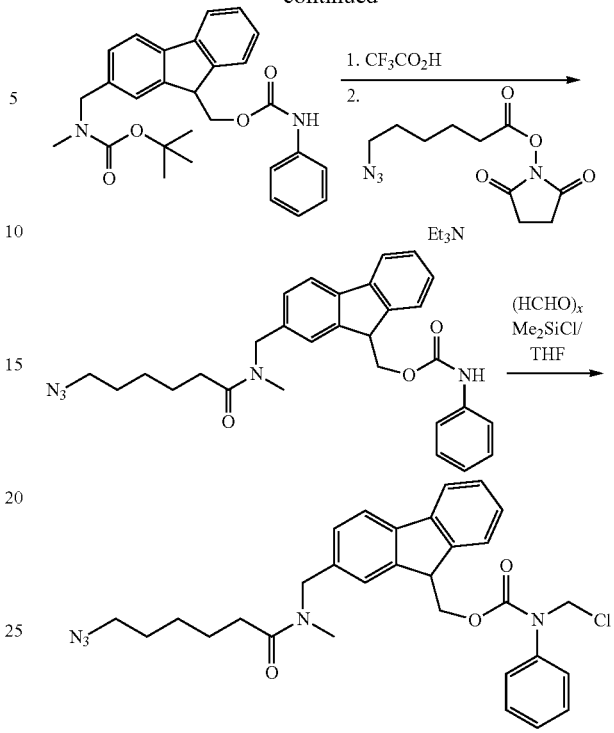

A solution of fluorene-2-carbonyl chloride (prepared from fluorene-2-carboxylic acid and oxalyl chloride) in THF is added to aqueous methylamine (2 molar equivalents) to prepare N-methyl fluorene-2-carboxamide. Reduction of the amide using LiAlH$_4$ in ether provides 2-((methylamino)methyl)fluorene. The amine is protected by reaction with di-tert-butyl dicarbonate to provide 24N-$^t$BOC—N-methylamino) methyl)fluorene.

A solution of the 2-((N-$^t$BOC—N-methylamino)methyl) fluorene in anhydrous tetrahydrofuran (THF) is cooled to −78° C., then treated with a solution of lithium bis(trimethylsilyl)amide in THF (1.2 molar equivalents). After 1 hr, ethyl formate is added and the mixture is allowed to warm to ambient temperature. The mixture is diluted with ethyl acetate and washed successively with 0.1 N HCl, water, saturated aqueous NaHCO$_3$, and brine, then dried over MgSO$_4$, filtered, and evaporated to provide the 2-((N-$^t$BOC—N-methylamino)methyl)-fluorene-9-carboxaldehyde. This compound is dissolved in methanol and treated with NaBH$_4$ to provide 9-(2-((N-$^t$BOC—N-methylamino)methyl)fluorenylmethanol.

The 9-(2-((N-$^t$BOC—N-methylamino)methyl)fluorenylmethanol is dissolved in THF and treated with triphosgene and pyridine according to the general procedure of Preparation 4 to provide the chloroformate. The chloroformate is reacted with aniline according to the method of Preparation 5 to provide O-(9-(2-((N-$^t$BOC—N-methylamino)methyl)fluorenylmethyl)N-phenylcarbamate The carbamate is dissolved in trifluoroacetic acid to remove the $^t$BOC protecting group. After evaporation to dryness, the resulting amine is dissolved in THF and treated with N-(6-azidohexanoyl)succinimide and triethylamine (2 equivalents) to provide O-(9-(2-((N-(6-azidohexanoyl)-N-methylamino)methyl)fluorenylmethyl)N-phenylcarbamate.

Reaction of O-(9-(2-((N-(6-azidohexanoyl)-N-methylamino)methyl)fluorenylmethyl) N-phenylcarbamate. with paraformaldehyde in 1:1 THF/chlorotrimethylsilane provides the product N-chloromethyl carbamate.

Preparation 24

Linker-Drug Compound with SN-38

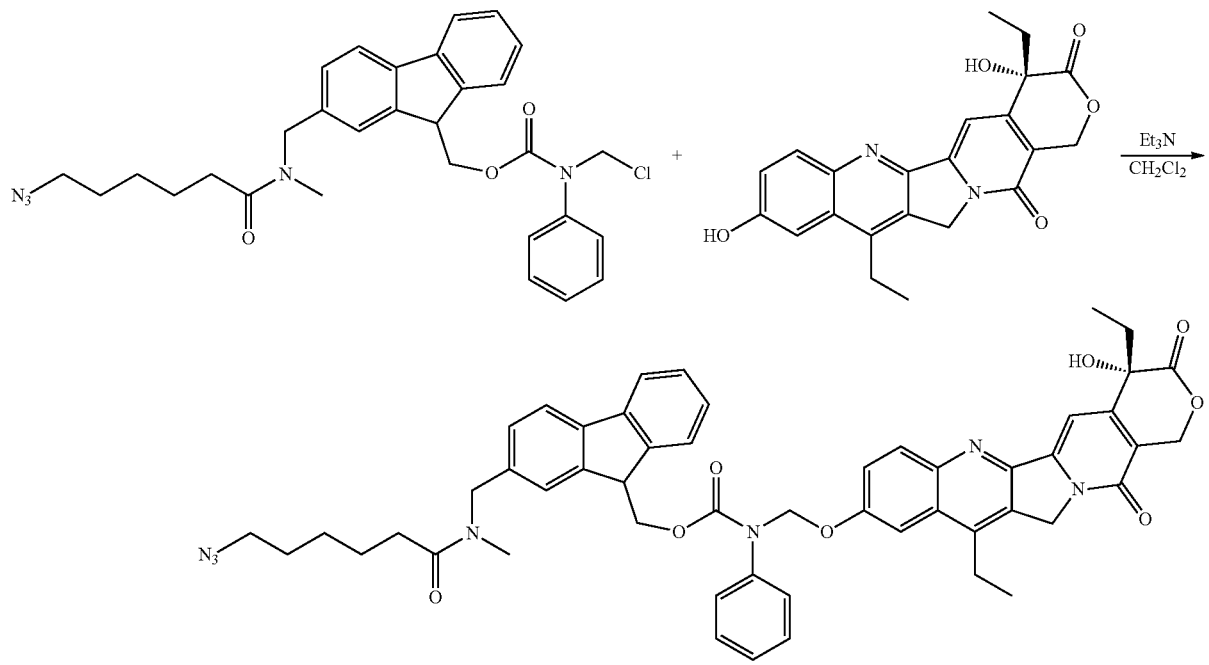

A solution of the N-chloromethylcarbamate of Preparation 23 (1 equivalent), SN-38 (1 equivalent), and sodium iodide (10 equivalents) in anhydrous acetone is treated with triethylamine (1 equivalent). The product is purified by silica gel chromatography.

Preparations 25-30 are prophetic examples showing the preparation of embodiments wherein Y is $NBCH_2$ and the linker is coupled through $R^5$.

Preparation 25

General Scheme for Preparation of Azidoalkyl-Linkers

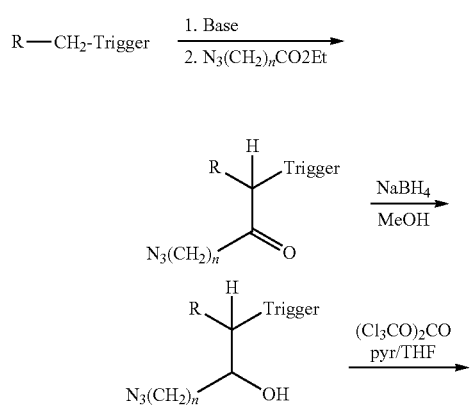

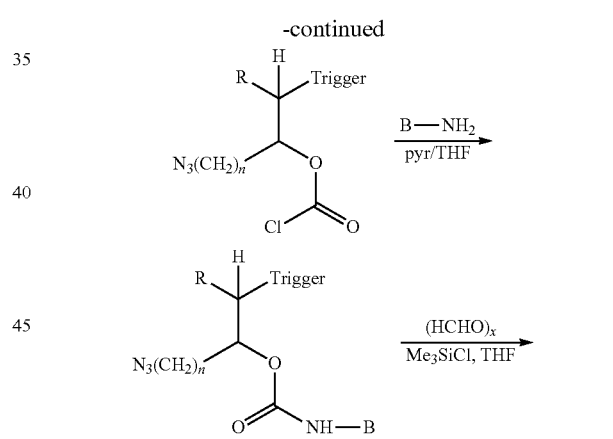

Claisen condensation of R—$CH_2$-Trigger with an ω-azidoalkanoate ester $N_3(CH_2)_nCO_2R'$ (n=3-6) in the presence of a strong base, for example NaH, lithium bis(trimethylsilyl)amide (LiHMDS), or lithium diisopropylamide (LDA), provides a ketone which is reduced to the alcohol by reaction with a mild reductant, for example sodium borohydride in methanol. The resulting alcohol is then converted into the carbamate via the chloroformate, and then into the N-chloromethylcarbamate as described above.

Preparation 26

General Scheme for Preparation of BOC-Protected Amine Linkers

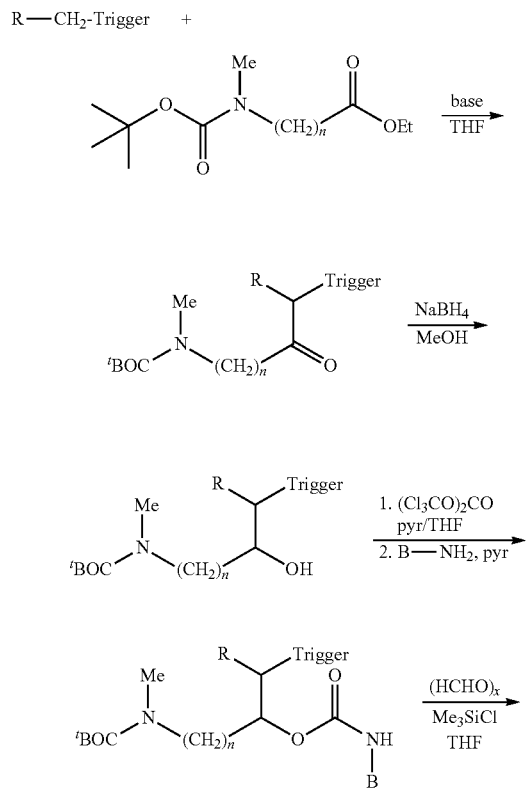

Claisen condensation of R—CH$_2$-Trigger with an ω-((N-tert-butoxycarbonyl N-alkyl)amino)alkanoate ester (n=3-6) in the presence of a strong base, for example NaH, lithium bis(trimethylsilyl)amide (LiHMDS), or lithium diisopropylamide (LDA), provides a ketone which is reduced to the alcohol by reaction with a mild reductant, for example sodium borohydride in methanol. The resulting alcohol is then converted into the carbamate using amine B—NH$_2$ as described in Preparation 5. The carbamate is converted into the N-chloromethylcarbamate as described in Preparation 6.

After coupling with a molecule comprising an alcohol, thiol, phenol, or thiophenol group, the BOC group is removed from the carbamate by treatment with trifluoroacetic acid. The resulting amine is coupled with a macromolecule comprising a carboxylic acid using a condensing agent, for example a carbodiimide such as EDCI.

Preparation 27

Alternate Scheme for Preparation of Azidoalkyl-Linkers

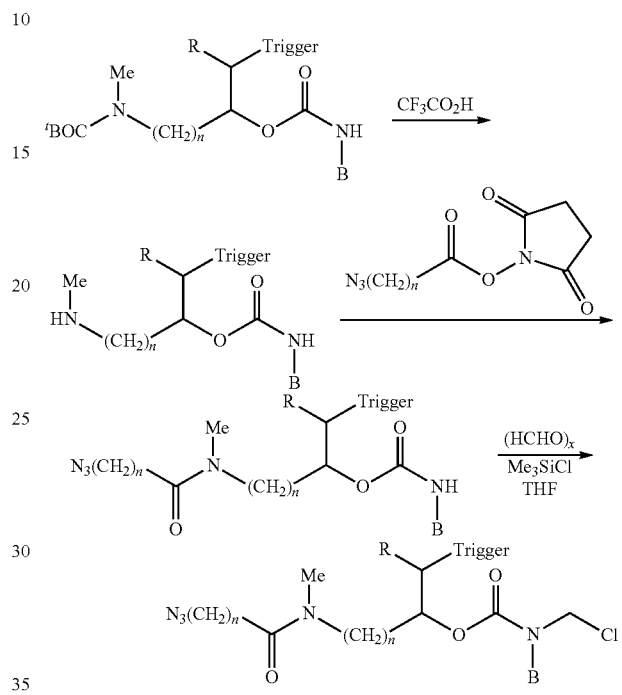

The BOC group is removed from the intermediate BOC-protected carbamate of Preparation 25 by treatment with trifluoroacetic acid, and reaction of the resulting amine with an ω-azidoalkanoate N-hydroxysuccinimide ester (n=3-6) provides the azidoamide. This is converted into the N-chloromethylcarbamate as described in Preparation 26.

Preparation 28

Preparation of a Sulfonyl-Triggered Amine Linker

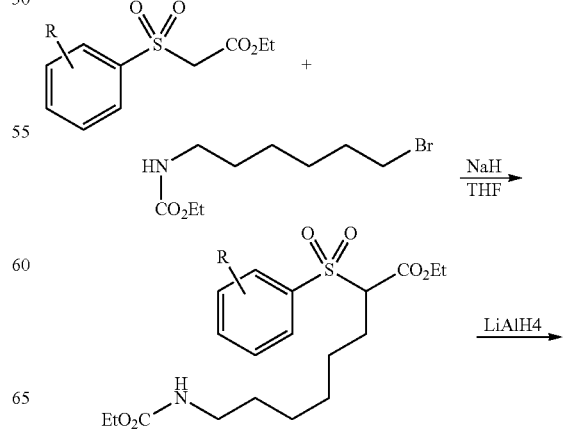

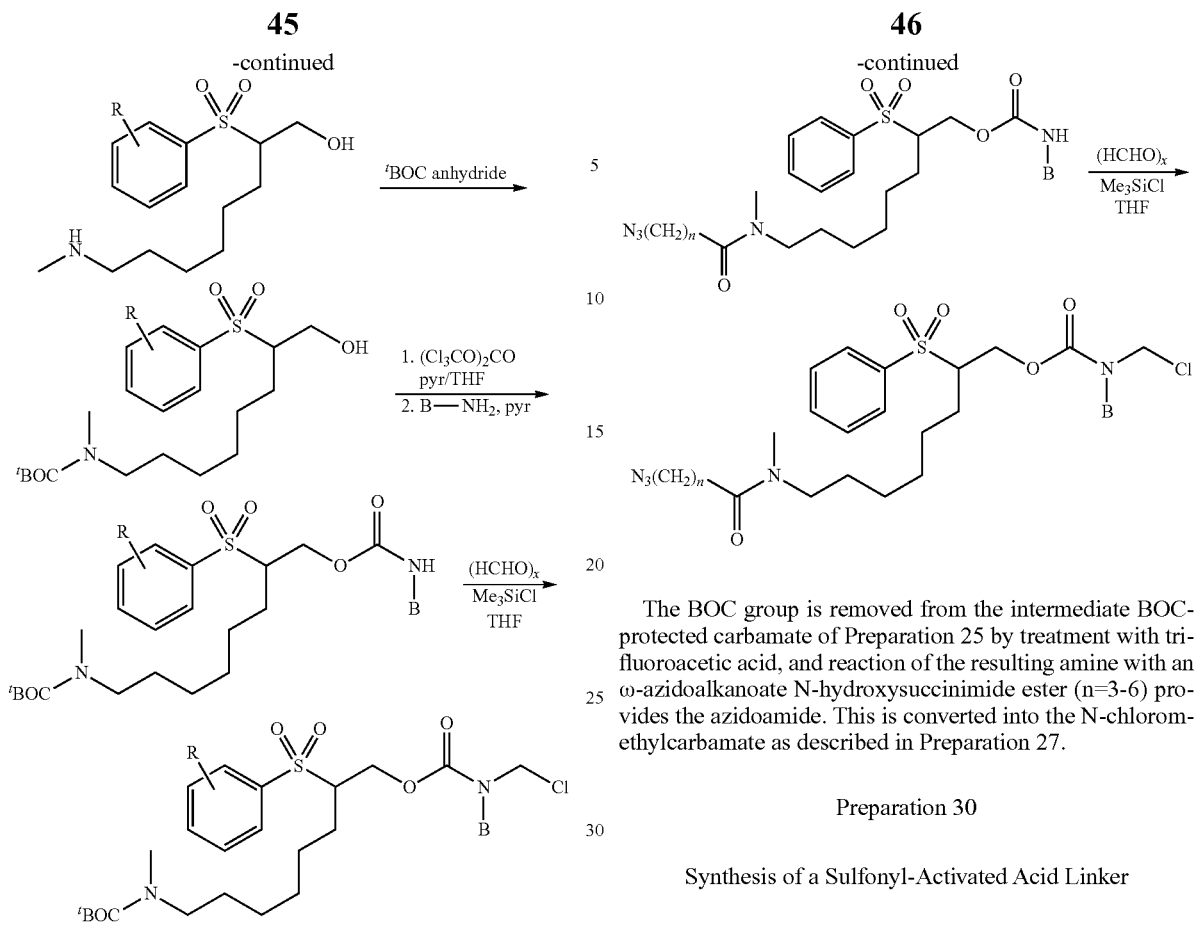

An ethyl (2-phenylsulfonyl)acetate is deprotonated using excess NaH in THF and alkylated with N-(6-bromohexyl) ethyl carbamate. The product is reduced using lithium aluminum hydride in ether to provide the methylamino alcohol, which is N-protected as the BOC carbamate. The alcohol is converted to the chloroformate and thence into the carbamate and into the N-chloromethyl carbamate according to the previous procedures.

Preparation 29

Preparation of a Sulfonyl-Triggered Azide Linker

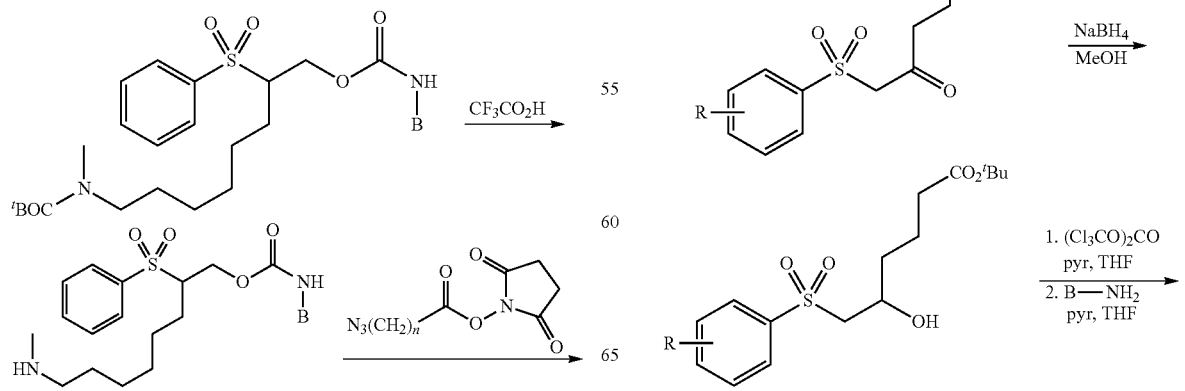

The BOC group is removed from the intermediate BOC-protected carbamate of Preparation 25 by treatment with trifluoroacetic acid, and reaction of the resulting amine with an ω-azidoalkanoate N-hydroxysuccinimide ester (n=3-6) provides the azidoamide. This is converted into the N-chloromethylcarbamate as described in Preparation 27.

Preparation 30

Synthesis of a Sulfonyl-Activated Acid Linker

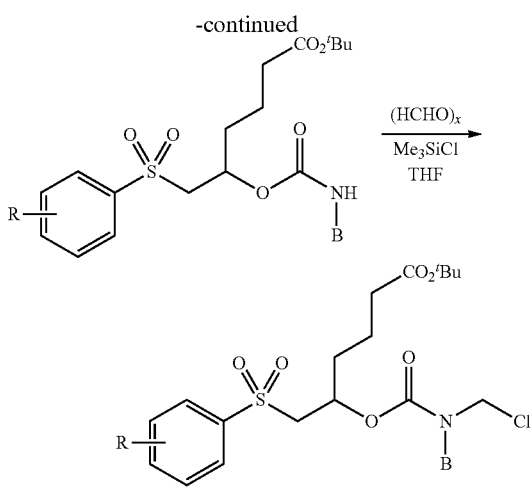

A phenyl methylsulfone is deprotonated with NaH in tetrahydrofuran, then acylated with glutaric anhydride to provide a keto-acid. The resulting acid is protected as the tert-butyl ester, and the ketone is reduced using NaBH$_4$. The resulting alcohol is converted into the carbamate via the chloroformate, and thence to the N-chloromethyl carbamate as described above.

Preparation 31

Synthesis of Linked Peptides

Peptide synthesis is performed using standard methods for solid-phase peptide synthesis, using a serine, tyrosine, or cysteine in a suitably protected form such that the side chains of these residues may be selectively deblocked without deprotection of other residues. The partially deprotected peptide is reacted with an excess of intermediate of formula (3) which is not yet linked to dendrimer in the presence of a mild base. After washing the resin, the product peptide is deblocked and cleaved from the resin to provide the corresponding intermediate prior to dendrimer linkage wherein D is a peptide.

As one example, CCK8 (Asp-Tyr-Met-Gly-Trp-Met-Asp-Phe-NH$_2$) is synthesized on solid support using Rink resin using methods known in the art, for example as described in U.S. Pat. No. 4,769,445 (incorporated herein by reference). Commercial Fmoc-Phe-Rink amide-MBHA resin is pre-swollen in DMF for 30 min, then suspended and shaken in piperidine/DMF (1:4 by volume, 50 ml) for 30 min at room temperature to remove the Fmoc group. The product is isolated by filtration and washed (3×50 ml each) with DCM, 5% N,N-diisopropylethylamine (DIEA) in DCM, and DCM to give the free base of Phe-Rink amide-MBHA-Resin. Fmoc-Asp(O$^t$Bu)-OH (1.23 g, 3 mmol), DCC (0.62 g, 3 mmol), and HOBt (0.69 g, 4.5 mmol) are dissolved in 50 ml of 4:1 by volume DCM/DMF with stirring at 0° for 1 hour. Phe-Rink amide-MBHA resin (1 meq) is suspended in the filtered reaction mixture (precipitated DCU removed) and shaken for 2 to 15 hours at room temperature. The Fmoc-Asp-(O$^t$Bu)-Phe-Rink amide-MBHA resin product is collected by filtration and washed with DCM. The Fmoc-Asp-(O'Bu)-Phe-Rink amide-MBHA resin is suspended and shaken in piperidine/DMF (1:4 by volume, 50 ml) for 3 min at room temperature and a second time for 7 min to remove the Fmoc group. The product is isolated by filtration and washed (3×50 ml each) with DMF and DCM to give the free base of Asp-(O$^t$Bu)-Phe-Rink amide-MBHA resin. Fmoc-Met-OH (1.12 g, 3 mmol), DCC (0.62 g, 3 mmol), and HOBt (0.69 g, 4.5 mmol) are dissolved in 50 ml of 4:1 by volume DCM/DMF with stirring at 0° for 1 hour. Asp-(O$^t$Bu)-Phe-Rink amide-MBHA resin (1 meq) is suspended in the filtered reaction mixture (precipitated DCU removed) and shaken for 2 to 15 hours at room temperature. The Fmoc-Met-Asp-(O$^t$Bu)-Phe-Rink amide-MBHA resin product is collected by filtration and washed with DCM and DMF. The Fmoc-Met-Asp-(O'Bu)-Phe-Rink amide-MBHA resin is deprotected and coupled sequentially with Fmoc-Trp-OH (1.28 g, 3 mmol), Fmoc-Gly-OH (0.89 g, 3 mmol), Fmoc-Met-OH (1.12 g, 3 mmol), Fmoc-Tyr-OH (1.37 g, 3 mmol), and Boc-Asp(O$^t$Bu)-OH (1.23 g, 3 mmol) to provide Boc-Asp(O$^t$Bu)-Tyr-Met-Gly-Trp-Met-Asp(O$^t$Bu)-Phe-Rink amide-MBHA resin. The Boc-Asp(O$^t$Bu)-Tyr-Met-Gly-Trp-Met-Asp(O$^t$Bu)-Phe-Rink amide-MBHA resin is washed with DCM (3×50 ml), suspended and shaken in a mixture of O-(9-fluorenylmethyl)N-phenyl N-chloromethylcarbamate (10 equivalents) and triethylamine (1 equivalent) in DCM. The resin is isolated by filtration and washed (3×50 ml each) with DCM. The resulting Boc-Asp(O$^t$Bu)-Tyr(OX)-Met-Gly-Trp-Met-Asp(OtBu)-Phe-Rink amide-MBHA resin is cleaved from the resin and deblocked by shaking with a mixture of 8% phenol, 5% thioanisole, 5% water, and 3% 3,6-dioxa-1,8-octanedithiol in trifluoroacetic acid (10 mL/g resin) for 4 hours. The resin is removed by filtration, and the peptide is precipitated by addition of 10 volumes of ether. The crude peptide is purified by reversed-phase HPLC.

In another example, a cysteine-containing peptide is prepared by solid phase synthesis using the methods described above, incorporating an S-(allyloxycarbonylaminomethyl)-cysteine [Cys(allocam)] or S—(N-[2,3,5,6-tetrafluoro-4-(N'-piperidino)phenyl]-N-allyloxycarbonyl-amino)cysteine [Cys(fnam)] residue. Prior to cleavage from the resin, the cysteine residue is selectively deblocked using (Ph$_3$P)$_4$Pd and phenylsilane in DCM, then reacted with a compound of formula (II) as described above. The peptide is finally deblocked, removed from the resin, and purified as described above.

Preparation 32

Linker-Drug Compounds of 5-Fluorouracil

As an example of preparing compounds of the invention where D is the residue of a drug coupled through a heterocyclic N, linker-drug compounds of formula (III) may be prepared from 5-fluorouracil and a compound of formula (II) analogously to the procedures used by Taylor and Sloane, "1-Alkylcarbonyloxymethyl Prodrugs of 5-Fluorouracil (5-FU): Synthesis, Physicochemical Properties, and Topical Delivery of 5-FU", *J. Pharmaceutical Sci.* 87(1): 15-20 (1998), and by Roberts and Sloane, "Synthesis of 3-Alkylcarbonyl-oxymethyl Derivatives of 5-Fluorouracil", *J. Heterocyclic Chem.* 39: 905-910 (each incorporated herein by reference). Thus, a suspension of a compound of formula (II) wherein L is Cl (1 mmol) and NaI (1.3 mmol) in dry acetonitrile (1 mL) is stirred in the dark for 24 h, then filtered to afford a solution of the compound of formula (II) wherein L is I. The filtrate is allowed to react with a mixture of 1-(allyloxycarbonyl-oxymethyl)-5-fluorouracil [Liu, Fullwood, and Rimmer, "Synthesis of Allyloxycarbonylmethyl-5-fluorouracil and copolymerizations with N-vinylpyrrolidinone", *J. Materials Chem.* 10: 1771-7, 2000] (0.8 mmol) and 1,8-bis(dimethylamino)naphthalene at ambient temperature. After 6 h, the mixture is diluted with ether, stirred for 1 h, and filtered.

The filtrate is concentrated to provide the crude protected product, which is treated with a mixture of tetrakis(triphenylphosphine)-palladium(0) and phenylsilane in anhydrous THF for 1 h to remove the allyloxycarbonylmethyl protecting group. The mixture is evaporated, and the residue is purified by silica gel chromatography to provide the linker-drug compound of formula (III).

Examples 1-5 are prophetic examples describing how dendrimers are coupled to intermediates to obtain the constructs of the invention.

Example 1

Coupling to Dendrimers

Coupling reactions to dendrimers are monitored to insure completeness of reactions, typically using chromogenic or fluorogenic reactions. Acylation reactions use chromogenic leaving groups (e.g., p-nitro-phenyl (pNP) esters and carbonates) that can be continuously monitored. Free amines of the dendrimer are determined by the chromogenic reaction with TNPS. Alkynes and azides are determined by click reactions with fluorogenic azide and alkyne reagents, respectively. Thiols are determined by chromogenic reaction with DTNB. Modified dendrimers are analyzed by MS.

Sets of "releasable" bi-functional linkers with an activated group (e.g., chloroformate, HSE) for attachment to alcohol (carbonate) and amine (carbamate) groups of drugs on one end, and functional groups for attachment to dendrimers on the other: maleimido for attachment to thiols, carboxyl for amino groups, alkyne for azides, and azides for alkynes are prepared.

The linkers used in this example are acid-stable and base-labile, so basic conditions (e.g., for blocking group removal) cannot be used subsequent to attachment of the linker-drug moiety. If acylation reactions are used for PEGylation of dendrimers, they are performed before attachment of drugs containing nucleophiles (e.g., peptides) to avoid modifying the drug.

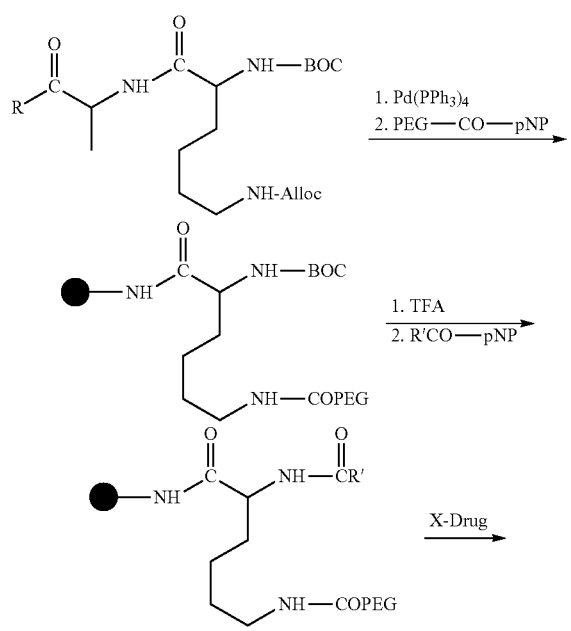

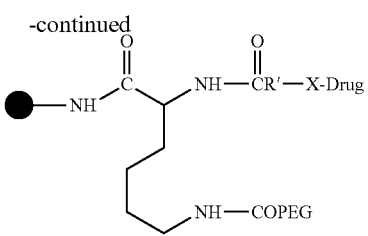

PLL dendrimer (Z=8) is coupled with commercially available α-BOC-ε-Alloc-Lys or α-BOC-ε-trifluoroacetyl-Lys (Sigma-Aldrich) or with a-BOC-e-(trifluoroacetyl)-Lys, providing surface-variegated dendrimers with Z=16 using a minor modification of a method to prepare 50% PEGylated PLL dendrimers (Kaminskas, L. M., et al., *J. Pharm Sci* (2009) 98:3871-3875). After removal of the ε-Alloc group (Pd(PPh$_3$)$_4$) or the trifluoroacetyl group (methoxide), free amines are coupled to activated mPEG, for example, PEG (5000)-pNP carbonate or mPEG-succinimidyl succinate. The tBOC groups are removed (25% TFA/DCM) to provide PLL dendrimers in which half of the surface amines are free, and the other half attached to PEG [PLL$_{16}$(ε-PEG5000)$_8$(α-NH$_2$)$_8$]. Free surface amines of the PEGylated dendrimers are reacted with an activated carboxylic acid containing a functional group (e.g., R'CO-pNP, where R'=alkyne, azide, thiol, etc.) for subsequent coupling to an appropriate functionalized linker-drug (X-Drug) to give PLL$_{16}$(ε-PEG5000)$_8$(α-Drug)$_8$.

Example 2

β-Eliminative Release of Molecules from PEGylated Dendrimers

Several releasable linker-carbamate-DNP analogs shown in Tables 4 and 5 are attached to PLL$_{16}$(α-PEG5000)$_6$(azide)$_8$ (PEG5000)$_8$ by CuAAC. Rates of DNP release at pH 7.4± serum are determined by HPLC for comparison to those determined for the linkers themselves.

Example 3

Protection of Peptides Against Proteases

The fluorogenic 7-amino-4-carbamoylmethylcoumarin (ACC) amide of a consensus trypsin-type sequence, N-Ac-Cys-PheSerArg-ACC (~16 Å fully extended) is prepared (Harris, J. L., et al., *Proc. Natl. Acad. Sci. USA* (2000) 97:7754-7759), and reacted at the thiol with bi-functional reagents that crosslink thiol and amino groups, and that differ in lengths separating the reactant groups. (Pierce offers a series of such reagents with spacer arm lengths ranging incrementally from 4.4 Å to >50 Å.) The derivatized peptides are attached to the 8 free amino groups of the intermediate PEGylated dendrimers described in Example 1 via the NHS group. Two linkers such that the cleavage site of the fully extended tetra-peptide is ~20 and 40 Å from the dendrimer into the 50 Å PEG 5000 layer are used. Kinetics of hydrolysis catalyzed by trypsin (MW 24 kDa; d~40 Å) and the larger tissue plasminogen activator (MW ~70 kDa; d~60 Å) of the conjugates and free peptide controls is monitored by fluorogenic release of ACC. Analogous experiments using a PEG 10,000 dendrimer—presumably having a deeper PEG-layer—are than tested to determine if protection against proteases can be increased with increased PEG size.

Example 4

Protection of Alkyl Carbonate Moieties in Linkers Attached to PEGylated Dendrimers Within the 7517 small molecule pharmaceuticals in the CMC database, 23% have aliphatic hydroxyl moieties, and a suitable linker is provided for incorporating these into the invention conjugates. It has been reported that esters of the 20-OH of camptothecin (CPT) attached to the core of a PEGylated PLL dendrimer completely are stable towards serum for up to 60 hrs, whereas corresponding PEG-conjugates hydrolyze in a few hours. If carbonates within a PEGylated dendrimers are likewise protected from esterases, our releasable linkers would allow predictable, controlled release of hydroxyl-containing small molecules from PEGylated dendrimers.

Using CPT as a model hydroxyl-containing drug, a carbonate is formed at the 20-OH by reaction with 5-octynol chloroformate (from 5-octynol and triphosgene/pyridine). The alkyne of the linker is attached to $PLL_{16}(PEG5000)_8(azide)_8$ containing 8 azide end-groups by CuAAC, providing a stable conjugate except for the carbonate moiety. The conjugate (i.e., carbonate) is studied (by HPLC) at pH 7.4± serum over a long period, to demonstrate that the carbonate is stable to serum PEGylated dendrimers linked to CPT by a carbonate using one or more of our releasable linkers (e.g., phenyl-sulfone analogs, see Table 4). Kinetic studies are performed at pH 7.4± serum (by HPLC) to determine the β-eliminative/ release rate. The aforementioned conjugate provides a soluble particle that is ~6% weight CPT, almost 10-fold higher density than could be achieved with linear monomethoxy PEG.

Example 5

PEGylated Dendrimer-Peptide Conjugates

Exendin-4, a 39-amino acid peptide from the Gila monster, is an agonist of the GLP-1 receptor, and thus an insulin secretagogue with glucoregulatory effects.

Exendin sequence: $H_2N$-HGEGTFTSDL$\underline{SK_{12}}$QMEEEAVRLFIEWL$\underline{K_{27}}$NGGPSSG APPPS—$NH_2$ (trypsin sites and amino terminus in red, α-helix underlined): Exendin-4 has a longer plasma lifetime than GLP-1 (~5 min), but a half-life of only 2.5 hrs. It is marketed for type 2 diabetes as Byetta®.

Exendin 4 consists of a 5-turn α-helix ($Leu_{10}$ to $Asn_{28}$; ~27 Å) with mobile N- and C-termini. It is relatively stable against plasma proteases in vitro ($t_{1/2}$~10 hr), and attachment to a PEG-dendrimer should increase stability even more. It has three potential trypsin cleavage sites: $Lys_{12}$ and/or $Lys_{27}$ are most susceptible, and $Arg_{20}$ is ~14-fold more resistant. PEGylation of the exendin N-terminus yields an inactive conjugate, whereas PEG-$Lys_{12}$ or PEG-$Lys_{27}$ are about as active agonists as the native peptide.

A releasable linker is coupled to the α- or $Lys_{12}$ amino groups of exendin, and each linker-exendin is coupled to a PEG5000 PLL dendrimer to give $PLL_{16}(\alpha\text{-PEG5000})_6(\epsilon\text{-exendin})_8$. Linear PEG-exendin controls are also prepared.

Exendin is prepared by SPPS by Fmoc/tBu chemistry, using an orthogonal blocking group at the side chain of the $Lys_{12}$ (e.g., monomethoxytrityl, MMT). The blocking group at the intended site of reaction (α-amino Fmoc or $Lys_{12}$ side chain MMT) is removed, and an HSE ester of an alkyne-containing or azide-containing releasable linker coupled to the free-amino group on-resin. Blocking groups and resin are removed (TFA), and the modified carbamoylated peptides purified by HPLC. The linker is attached to a) the dendrimer shell of PLL-PEG 5000 containing 8 PEGs and 8 azide or alkyne end groups, and b) a control azide- or alkyne-modified linear PEG 5000 by CuAAC.

The in vitro rate of β-eliminative release and escape of the peptide from the dendrimer is determined at pH 7.4± serum and 8.4 using SEC HPLC; the observed rate is a composite of the β-elimination and diffusion of the free peptide through PEG, but the latter should not contribute significantly.

The PEG and PEG-dendrimer conjugates are tested as agonists of the GLP1 receptor in membrane or cell-based assays (e.g., RIN-m5f cells, ATCC as described (Young, A., et al., (2000) WO00/66629) pages 74-75) before and after β-eliminative release of native exendin.

Conjugates are then treated with mild base to release native exendin that shows full activity as GLP1 agonists.

The conjugates are treated with trypsin and sera to determine accessibility to proteases; at various times, excess PMSF is added to quench serine proteases, peptides are released by mild base-catalyzed β-elimination and the remaining native peptide determined by HPLC.

Examples 6-9 are working examples describing construction of a dendrimer which has as its core two lysine residues linked through diaminohexane and provided with azido groups for linkage to drug. Examples 10 and 11 are prophetic examples showing linkage of this intermediate both to PEG and to an alkynyl linker coupled to drug.

Example 6

DAH[Lys]₂[α-Boc]₂[ε-Boc]₂

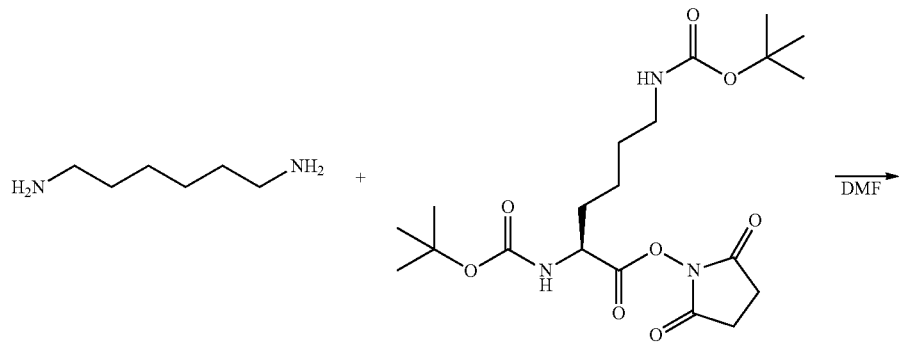

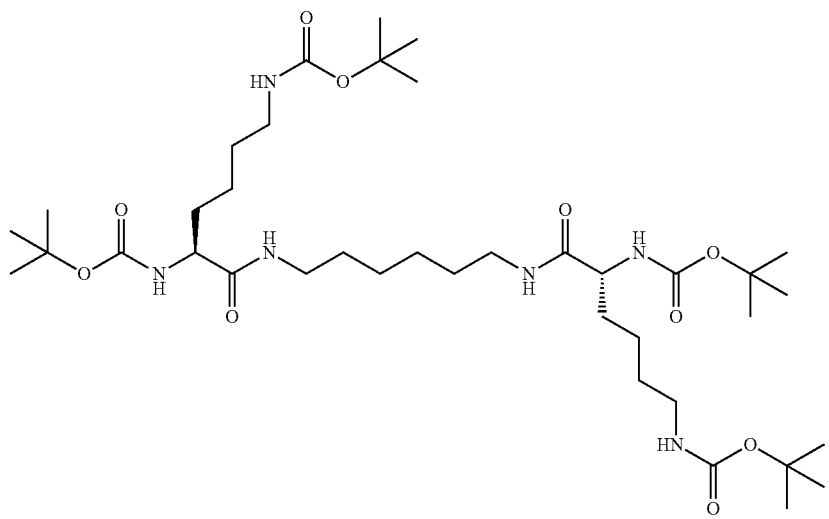

DAH[Lys]₂[α-Boc]₂[ε-Boc]₂

To a stirred solution of N$_\alpha$,N$_\epsilon$-bis(tert-butoxycarbonyl)-L-lysine succinimidyl ester (1.91 g; 4.31 mmol) in N,N-dimethylformamide (5 mL) was added a solution of 1,6-diaminohexane (0.200 g; 1.72 mmol) in N,N-dimethylformamide (5 mL) over 5 minutes. The reaction mixture was stirred at ambient temperature for 20 hours and was then diluted with water (100 mL). The aqueous phase was extracted 3× with ethyl acetate and the combined organic extracts were washed with water, saturated sodium hydrogen carbonate solution and brine. The organic phase was dried over magnesium sulfate and concentrated to give a colorless oil (1.93 g). Purification using a Thomson Instruments Single Step 40 g silica gel cartridge eluting with 1:1 ethyl acetate/hexanes followed by 70:30 ethyl acetate/hexanes furnished DAH[Lys]₂[α-Boc]₂ [ε-Boc]₂ (1.15 g; 86%) as a white solid. ¹H NMR (DMSO-d6) 1.17-1.52 (50H, br. m), 2.85 (4H, br. m), 2.96 (4H, m), 3.77 (2H, m), 6.70 (4H, m), 7.69 (2H, m).

Example 7

DAH[Lys]$_4$[α-Boc]$_4$[ε-Boc]$_4$

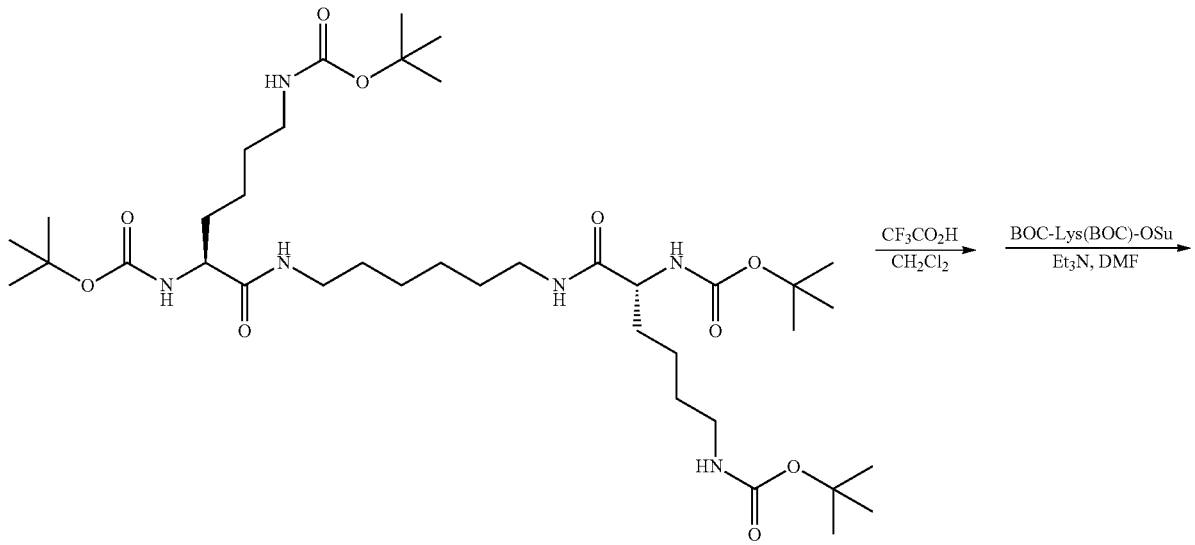

DAH[Lys]$_2$[α-Boc]$_2$[ε-Boc]$_2$

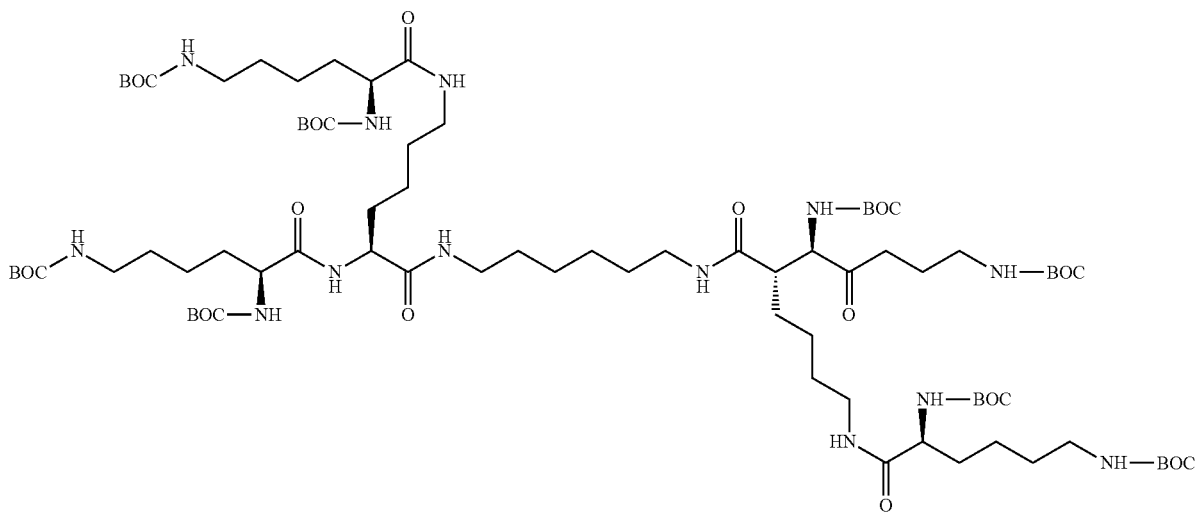

DAH[Lys]$_4$[α-Boc]$_4$[ε-Boc]$_4$

Trifluoroacetic acid (5 mL) was added to a stirred solution of DAH[Lys]$_2$[α-Boc]$_2$[ε-Boc]$_2$ (0.200 g; 0.259 mmol) in dichloromethane (5 mL). The solution was stirred at room temperature for 1 hour and was then concentrated on the roto-vap. The crude salt was dissolved in N,N-dimethylformamide (8 mL) and triethylamine (0.58 mL; 4.16 mmol) added. To this solution was added Boc-Lys(Boc)-OSu (0.505 g; 1.14 mmol) and the reaction mixture stirred for 20 hours. The solution was added to ice-water with stirring (500 mL) by pipette and the resulting fine suspension stirred for 35 minutes. The solid was collected by filtration, washed with water and dried. It was then re-suspended in acetonitrile (2 mL) and stirred for 1 hour. The solid was collected, washed with acetonitrile and dried to give DAH[Lys]$_4$[α-Boc]$_4$[ε-Boc]$_4$ (0.337 g; 77%) as a white solid. $^1$H NMR (DMSO-d6) 1.21 (116H, Br. m), 2.82-3.06 (8H, br. m), 3.79 (4H, br. m), 4.17 (2H, br. m), 6.67-6.91 (8H, m), 7.66-7.81 (6H, m).

Example 8

Boc-L-Azidonorleucine succinimidyl ester (BOC-ANL-OSu)

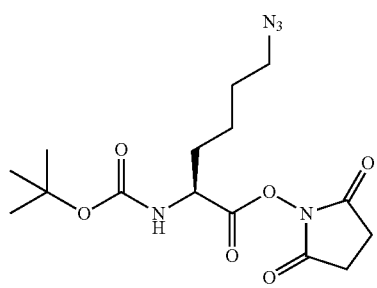 [SMILES: CC(C)(C)OC(=O)N[C@@H](CCCCN=[N+]=[N-])C(=O)ON1C(=O)CCC1=O]

To a stirred solution of N-(tert-butoxycarbonyl)-L-azidonorleucine (0.505 g; 1.85 mmol) and triethylamine (284 µL; 2.04 mmol) in tetrahydrofuran (10 mL) was added N,N'-disuccinimidyl carbonate (0.523 g; 2.04 mmol). The reaction mixture was stirred at ambient temperature for 1.5 hours and was then concentrated on the roto-vap. The residue was taken up in ethyl acetate and washed with water, saturated sodium hydrogen carbonate solution and saturated sodium chloride solution. The organic phase was dried over magnesium sulfate and concentrated to give a colorless oil (0.744 g). Purification by column chromatography using a Thomson Instruments Single Step 40 g silica gel cartridge eluting with hexanes followed by 1:1 ethyl acetate/hexanes produced the product (0.536 g; 79%) as a colorless oil. $^1$H NMR (DMSO-d6) 1.39 (9H, s), 1.46 (4H, m), 1.74 (2H, m), 2.80 (4H, br s), 3.30 (2H, m overlaps solvent), 4.31 (1H, m), 7.61 (1H, d, J=7.8 Hz). Fmoc-L-azidonorleucine succinimidyl ester is prepared similarly starting from Fmoc-L-azidonorleucine.

Example 9

DAH[Lys]$_4$[BOC-ANL]$_8$

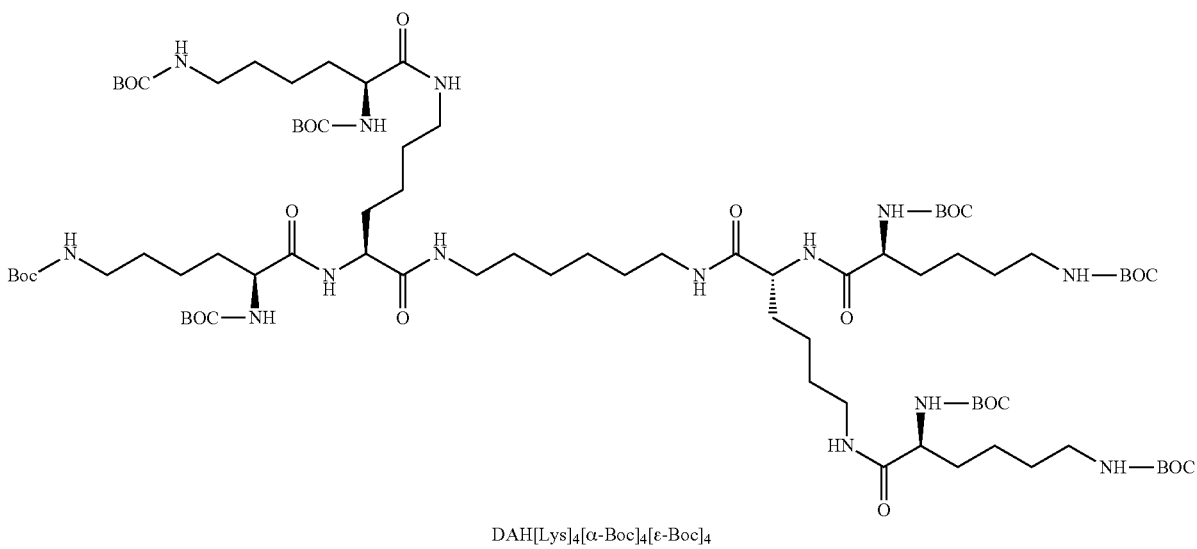

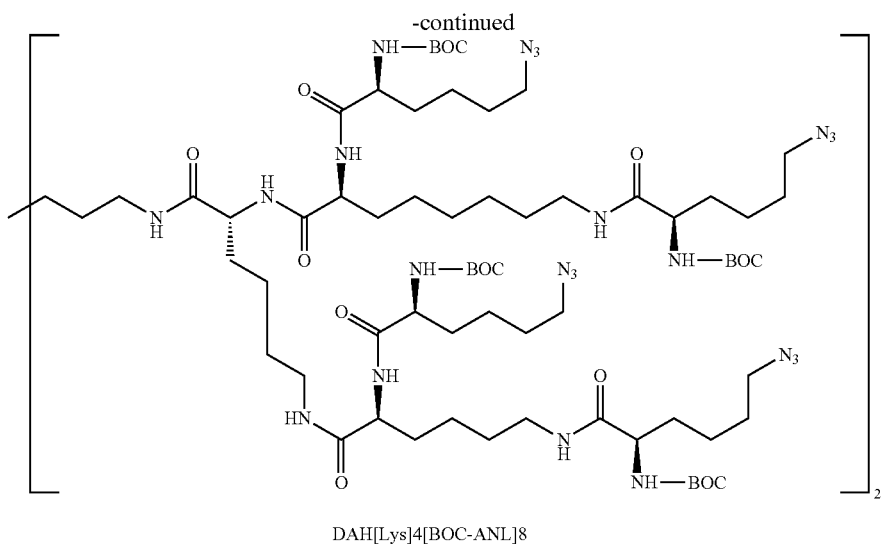

DAH[Lys]4[BOC-ANL]8

Trifluoroacetic acid (4 mL) was added to a stirred suspension of DAH[Lys]$_4$[α-Boc]$_4$[ε-Boc]$_4$ (0.139 g; 82.4 μmol) in dichloromethane (4 mL) and the resulting solution stirred at ambient temperature for 1.5 hours. The solution was concentrated and the crude salt was taken up in N,N-dimethylformamide (4 mL) and triethylamine (368 μL; 2.7 mmol) added. To this solution was added a solution of Boc-L-azidonorleucine succinimidyl ester (0.268 g; 726 μmol) in N,N-dimethylformamide. The reaction mixture was stirred at room temperature for 22 hours and was then added by pipette to a stirred ice-water (200 mL) solution. The resulting suspension was stirred for 30 minutes and was then collected by filtration. The solid was washed with water and dried. It was re-suspended in acetonitrile (2 mL) and stirred for 30 minutes. The solid was collected, washed with acetonitrile and dried to give DAH[Lys]$_4$[BOC-ANL]$_8$ (0.181 g; 75%) as a white solid.

Example 10

DAH[Lys]$_4$[NL]$_8$[mPEG$_{5000}$]$_8$[N$_3$]$_8$

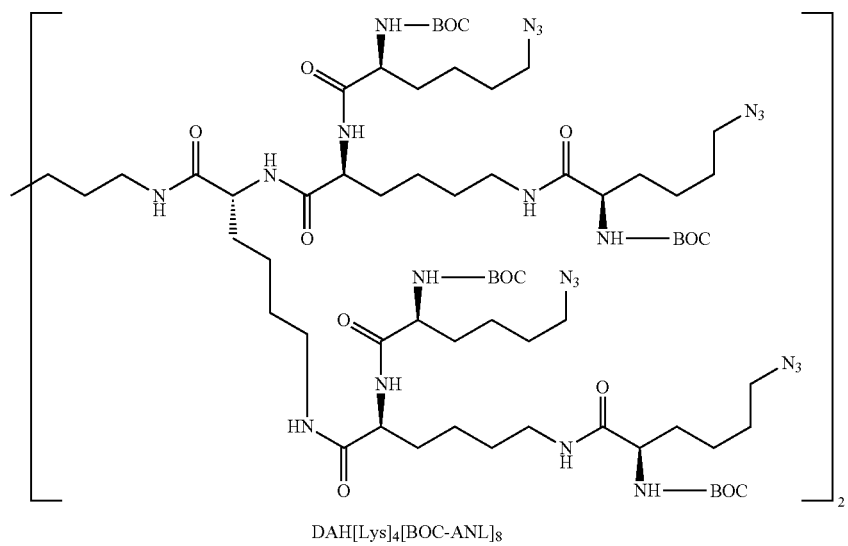

DAH[Lys]4[BOC-ANL]8

1. CF$_3$CO$_2$H, CH$_2$Cl$_2$
2. mPEG(5000)-NHS, Et$_3$N DMF

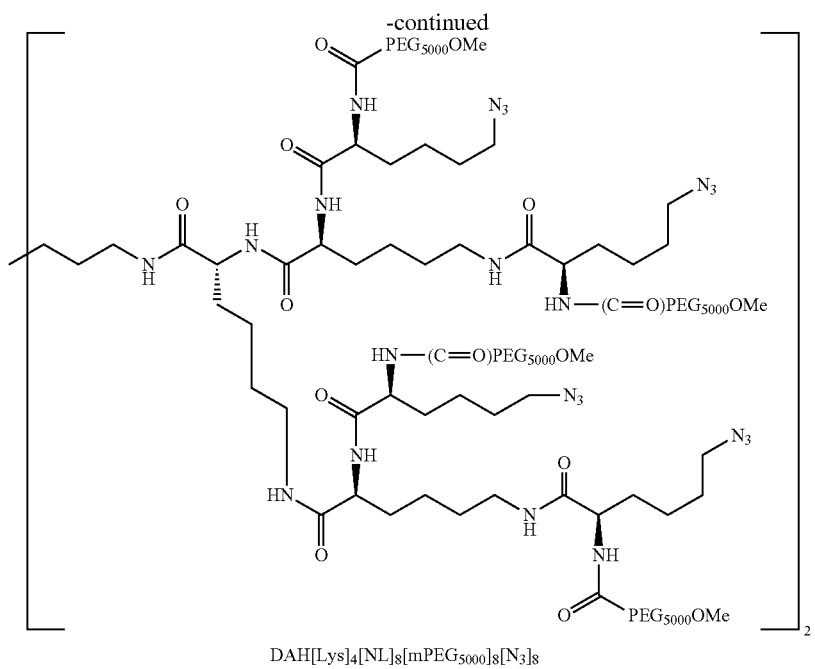

DAH[Lys]₄[NL]₈[mPEG₅₀₀₀]₈[N₃]₈

Trifluoroacetic acid is added to a stirred suspension of DAH[Lys]₄[BOC-ANL]₈ in dichloromethane as described for other examples above and the resulting solution is stirred at ambient temperature for 1.5 hours. The solution is concentrated and the crude salt is taken up in N,N-dimethylformamide and triethylamine sufficient to neutralize the salts and allow subsequent coupling is added. To this solution is added a molar excess of monomethoxy-polyethylene glycol succinimidyl ester (mw 5000) as a solution in N,N-dimethylformamide. The reaction mixture is stirred at room temperature for 22 hours and is then dialyzed against methanol using a 10,000-mw cutoff dialysis membrane to remove small molecule reagents and byproducts. The dialysate is evaporated to dryness to provide the product.

Example 11

Conjugation of Alkynyl-Linker-Drug with DAH [Lys]₄[NL]₈[mPEG₅₀₀₀]₈[N₃]₈

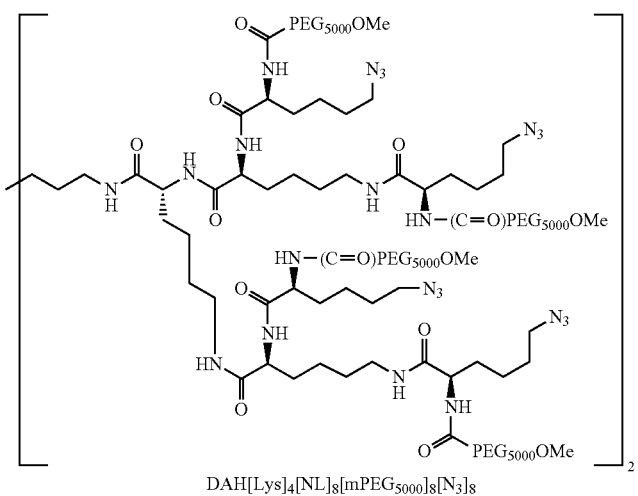

DAH[Lys]₄[NL]₈[mPEG₅₀₀₀]₈[N₃]₈

-continued

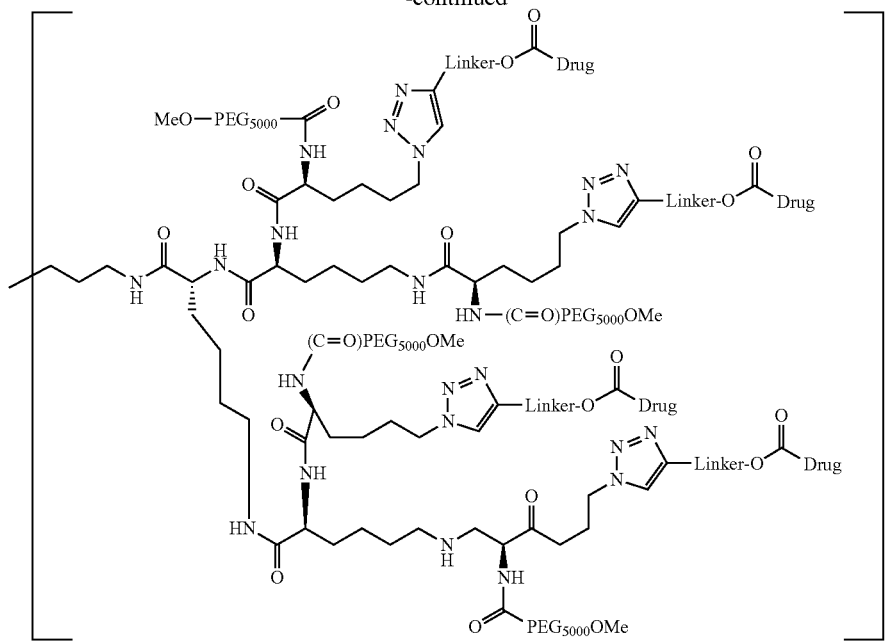

A solution of sodium ascorbate (1.5 M in water) is added to a blue mixture of 0.1 M $CuSO_4$ in water and 50 mM TBTA in dimethylsulfoxide (DMSO), and the resulting colorless solution is immediately added to a solution of 1 equivalent of the PEGylated alkyne dendrimer $DAH[Lys]_4[NL]_8[MPEG_{5000}]_8[N_3]_8$ and 10 equivalents of alkyne-linker-drug in 1:2 water/DMSO. The mixture is allowed to react overnight, and is then dialyzed against water until HPLC analysis reveals complete removal of the uncoupled alkynyl-linker-drug. The dialysate is lyophilized to provide the product.

Examples 12-16 result in compounds of the invention wherein 4 copies of the peptide drug exendin are coupled through linkers to the polylysine dendrimer that has been PEGylated. In these embodiments, X is O and Y is absent.

Example 12

Alkynyl-Linker—Exendin (N-Terminally Linked)

Rink-amide TentaGel resin containing the exendin-4 sequence (HGEGTFTSDLSKQ MEEEAV-RLFIEWLKNG-GPSSGAPPPS—$NH_2$) in protected form is prepared by solid-phase synthesis using standard FMOC/t-Bu solid-phase synthesis techniques. After removal of the last FMOC group and washing the resin three times with dichloromethane to remove excess piperidine, the resin is treated with a solution of 3 equivalents of the alkynyl-Linker succinimidyl carbonate in dichloromethane/DMF and 1.5 equivalent of N-methylmorpholine. After coupling is completed, the resin is washed to remove excess reagents. The linker-exendin is removed from the resin and deblocked by treatment with a cocktail of trifluoroacetic acid, phenol, thioanisole, and 3,6-dioxa-1,8-octanedithiol. The linker-exendin is then purified by reversed-phase HPLC using a gradient of acetonitrile and water containing 0.1% trifluoroacetic acid, and lyophilized.

Example 13

Alkynyl-Linker Exendin ($Lys^{12}$-Linked)

Rink-amide TentaGel resin containing the exendin-4 sequence (HGEGTFTSDLSKQ MEEEAV-RLFIEWLKNG-GPSSGAPPPS—$NH_2$) in protected form is prepared by solid-phase synthesis using standard FMOC/t-Bu solid-phase synthesis techniques, with the exception that $Lys^{12}$ is introduced as Fmoc-Lys(mmt) (mmt=monomethoxytrityl) and the final coupling is performed using BOC-His in place of Fmoc-His. The mmt group is removed by treatment with dilute $CF_3CO_2H$ in dichloromethane, and the resin is treated with a solution of 3 equivalents of the alkynyl-Linker succinimidyl carbonate in dichloromethane/DMF and 1.5 equivalent of N-methylmorpholine. After coupling is completed, the resin is washed to remove excess reagents. The linker-exendin is removed from the resin and deblocked by treatment with a cocktail of trifluoroacetic acid, phenol, thioanisole, and 3,6-dioxa-1,8-octanedithiol. The linker-exendin is then purified by reversed-phase HPLC using a gradient of acetonitrile and water containing 0.1% trifluoroacetic acid, and lyophilized.

Example 14

Synthesis of an Example Alkynyl Linker Succinimidyl Carbonate

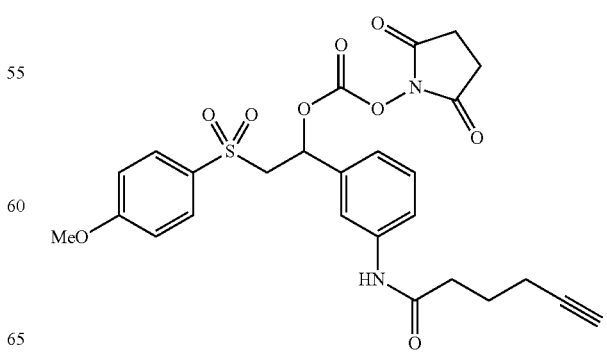

While the following procedure is given in detail for the 4-methoxyphenylsulfonyl trigger, other alkynyl-linker succinimidyl carbonates comprising arylsulfonyl triggers may be prepared by substitution of 4-methoxythiophenol in Step 1 below with other substituted thiophenols.

Step 1. 2-Bromo-3'-nitroacetophenone (2.98 g, 12.2 mmol) was dissolved in acetonitrile (12 mL). Water (12 mL) then sodium hydrogen carbonate (2.04 g, 24.3 mmol) were added. The resulting biphasic mixture was vigorously stirred and 4-methoxythiophenol (1.5 mL, 12.2 mmol) was added dropwise over 5 minutes. The reaction mixture was stirred at room temperature for 1.5 hours. It was then diluted with water and extracted with ethyl acetate (×3). The combined organic extracts were washed with 1M sodium carbonate and saturated sodium chloride, they were then dried over magnesium sulfate and concentrated under reduced pressure to give an orange oil (3.85 g) which solidified on standing. To the crude material was added ethyl acetate/hexanes (1:4, 20 mL) and the mixture stirred overnight. The solid was collected, washed with ethyl acetate/hexanes (1:4) and dried to yield the sulfide (2.75 g, 74%) as a pale orange solid. $^1$H NMR (DMSO-d6) δ3 733□, 4.53 (2H, s), 6.86 (2H, d, J=8.4 Hz), 7.28 (2H, d, J=8.4 Hz), 7.80 (1H, t, J=8.0 Hz), 8.36 (1H, d, J=7.8 Hz), 8.45 (1H, m), 8.62 (1H, t, J=1.8 Hz).

Step 2. To an ice-cooled stirred solution of the sulfide of Step 1 (2.75 g, 9.07 mmol) in ethyl acetate (75 mL) was added peracetic acid (5.8 mL of a 32 wt % solution in dilute acetic acid, 27.6 mmol) slowly over 10 minutes. The solution was stirred at ice-bath temperature for 10 minutes and then at ambient temperature for 2 hours. The suspension was dissolved by the addition of ethyl acetate (75 mL) and this solution was washed with 1 M sodium carbonate (×2), water, 0.1 M sodium hydrosulfite (×2), water, 1 M sodium carbonate and saturated sodium chloride. It was then dried over magnesium sulfate and concentrated under reduced pressure to furnish the sulfone as a white solid (3.04 g, 100%). $^1$H NMR (DMSO-d6) δ3.843□s, 5.41 (2H, s), 7.09 (2H, d, J=8.8 Hz), 7.72 (2H, d, J=8.7 Hz), 7.80 (1H, t, J=7.9 Hz), 8.35 (1H, m), 8.47 (1H, ddd, J=0.9 Hz, J=2.3 Hz, J=8.2 Hz), 8.62 (1H, t, J=1.9 Hz).

Step 3. Tin (II) chloride dihydrate (2.69 g, 11.9 mmol) was added to a stirred suspension of the sulfone of Step 2 (1.00 g, 2.98 mmol) in ethanol (30 mL). The reaction mixture was heated at gentle reflux for 30 minutes and the resulting yellow solution allowed to cool to room temperature. The solution was poured onto crushed ice and the pH adjusted to pH 8 with 1 M sodium carbonate. The suspension was equilibrated to room temperature and diluted to ~200 mL volume with water. It was then extracted with ethyl acetate (×3) and the combined organic layers were washed with saturated sodium chloride, dried over magnesium sulfate and concentrated under reduced pressure to produce the aniline (0.813 g, 89%) as a yellow solid. $^1$H NMR (DMSO-d6) δ3.823□s, 5.08 (2H, s), 5.36 (2H, br. s), 6.81 (1H, dt, J=1.9 Hz, J=7.2 Hz), 7.04-7.15 (5H, m), 7.79 (2H, d, J=8.8 Hz).

Step 4. To a stirred solution of 5-hexynoic acid (392 μL, 3.46 mmol) and oxalyl chloride (351 μL, 4.15 mmol) in anhydrous dichloromethane (5 mL) was added 2 drops of anhydrous N,N-dimethylformamide resulting in gas evolution. The solution was stirred for 15 minutes after which time gas evolution had ceased and a further 2 drops of anhydrous N,N-dimethylformamide were added (no gas evolution). The solution was stirred for 10 minutes and was then concentrated on the rotary evaporator. The crude acid chloride was dissolved in anhydrous dichloromethane (5 mL) and slowly added to a stirred suspension of the aniline of Step 3 (0.813 g, 2.66 mmol) and triethylamine (1.1 mL, 8.07 mmol) in anhydrous dichloromethane (20 mL). The resulting solution was stirred at room temperature for 2 hours and was then diluted with ethyl acetate. The solution was washed with water, 1 M sodium carbonate, water and saturated sodium chloride. It was dried over magnesium sulfate and concentrated under reduced pressure to give the crude amide as a brown oil (1.28 g). Purification utilizing a Thomson Instruments Single Step 40 g silica gel cartridge and eluting with 100% hexanes followed by 50% ethyl acetate/50% hexanes gave the amide (0.484 g, 46%) as a white solid. $^1$H NMR (DMSO-d6) δ$_1$□□□□, 2.21 (2H, td, J=2.7 Hz, J=7.1 Hz), 2.41 (2H, t, J=7.5 Hz), 2.82 (1H, t, J=2.7 Hz), 3.84 (3H, s), 5.18 (2H, s), 7.11 (2H, d, J=9.2 Hz), 7.41 (1H, t, J=8.1 Hz), 7.65 (1H, d, J=8.3 Hz), 7.79 (2H, d, J=9.2 Hz), 7.84 (1H, d, J=7.8 Hz), 8.09 (1H, t, J=1.8 Hz), 10.15 (1H, s).

Step 5. To a stirred suspension of the amide of Step 4 (0.484 g, 1.21 mmol) in methanol (12 mL) was added in portions over 5 minutes sodium borohydride (0.102 g, 2.70 mmol). The resulting solution was stirred for 35 minutes and then quenched by the addition of saturated ammonium chloride. It was then concentrated on the rotary evaporator, diluted with water and extracted with ethyl acetate (×3). The organic extracts were combined, washed with saturated sodium chloride and dried over magnesium sulfate. The solution was concentrated to afford the alcohol (0.438 g, 90%) as white foam. $^1$H NMR (DMSO-d6) δ1.71 (2H, m), 2.19 (2H, td, J=2.7 Hz, J=7.0 Hz), 2.37 (2H, t, J=7.4 Hz), 2.80 (1H, t, J=2.7 Hz), 3.37 (1H, dd, J=3.0 Hz, J=14.6 Hz), 3.56 (1H, dd, J=8.8 Hz, J=14.5 Hz), 4.88 (1H, m), 5.59 (1H, d, J=4.3 Hz), 6.93 (1H, d, J=7.7 Hz), 7.09 (2H, d, J=8.7 Hz), 7.17 (1H, t, J=7.8 Hz), 7.45 (1H, d, J=8.1 Hz), 7.49 (1H, s), 7.78 (2H, d, J=8.8 Hz).

Step 6. Pyridine (156 μL, 1.93 mmol) was added to a stirred solution of the alcohol of Step 5 (0.387 g, 0.964 mmol) and triphosgene (0.411 g, 1.39 mmol) in anhydrous tetrahydrofuran (10 mL). The resulting suspension was stirred for 30 minutes and was then filtered and the filtrate concentrated under reduced pressure. The crude chloroformate was taken up in anhydrous tetrahydrofuran (10 mL) and N-hydroxysuccinimide (0.598 g, 5.20 mmol) followed by pyridine (249 μL, 3.09 mmol) added. The reaction mixture was stirred at ambient temperature for 35 minutes and was then filtered and concentrated. The residue was dissolved in ethyl acetate and washed with water, 0.1 M hydrochloric acid, saturated sodium hydrogen carbonate, water and saturated sodium chloride. The organic solution was dried over magnesium sulfate and concentrated under reduced pressure to yield the crude product (0.469 g) as a pale yellow oil. Purification by silica gel column chromatography eluting with 100% hexanes followed by 50% ethyl acetate/50% hexanes produced the succinimidyl carbonate (0.296 g, 52%) as a pale yellow oil. $^1$H NMR (DMSO-d6) 1.73 (2H, m), 2.19 (2H, td), J=2.8 Hz, J=7.1 Hz), 2.39 (2H, t, J=7.4 Hz), 2.77 (4H, s), 2.80 (1H, t, J=2.6 Hz), 3.86 (3H, s), 3.89 (1H, dd, J=3.2 Hz, J=15.1 Hz), 4.30 (1H, dd, J=9.7 Hz, J=15.1 Hz), 5.87 (1H, dd, J=3.2 Hz, J=9.7 Hz), 7.07 (1H, d, J=8.4 Hz), 7.11 (2H, d, J=8.9 Hz), 7.28 (1H, t, J=8.0 Hz), 7.55 (1H, d, J=8.2 Hz), 7.61 (1H, s), 7.82 (2H, d, J=8.9 Hz.

Example 15

Preparation of an Example Alkynyl-Linker-Exendin-4 Compound

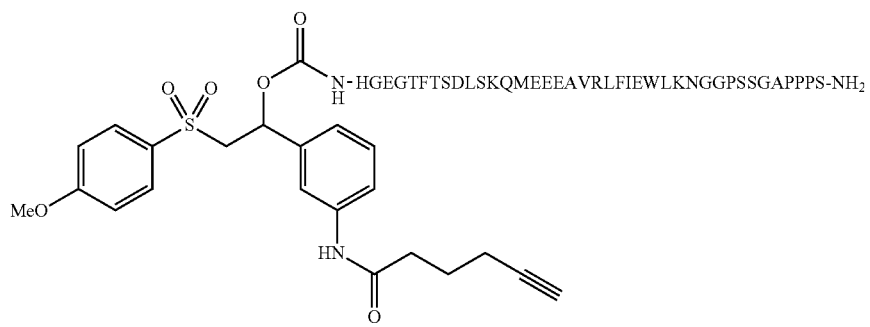

Rink-amide TentaGel resin containing the exendin-4 sequence (HGEGTFTSDLSKQ MEEEAV-RLFIEWLKNG-GPSSGAPPPS—NH$_2$) in protected form is prepared by solid-phase synthesis using standard FMOC/t-Bu solid-phase synthesis techniques. After removal of the last FMOC group and washing the resin three times with dichloromethane to remove excess piperidine, the resin is treated with a solution of 3 equivalents of the alkynyl-Linker succinimidyl carbonate of Example 14 in dichloromethane/DMF and 1.5 equivalents of N-methylmorpholine. After coupling is completed, the resin is washed to remove excess reagents. The linker-exendin is removed from the resin and deblocked by treatment with a cocktail of trifluoroacetic acid, phenol, thioanisole, and 3,6-dioxa-1,8-octanedithiol. The linker-exendin is then purified by reversed-phase HPLC using a gradient of acetonitrile and water containing 0.1% trifluoroacetic acid, and lyophilized.

Example 16

Coupling of Alkynyl-Linker-Exendins to DAH[Lys]$_4$[NL]$_8$[mPEG$_{5000}$][N$_3$]$_8$

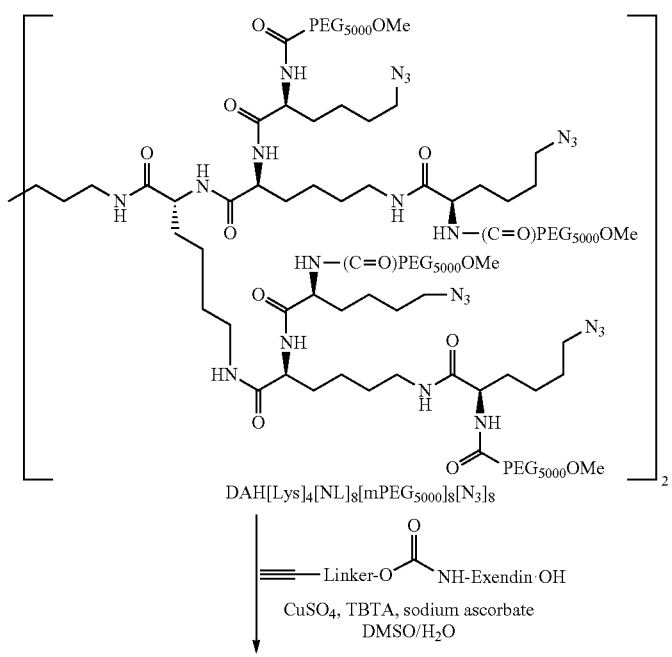

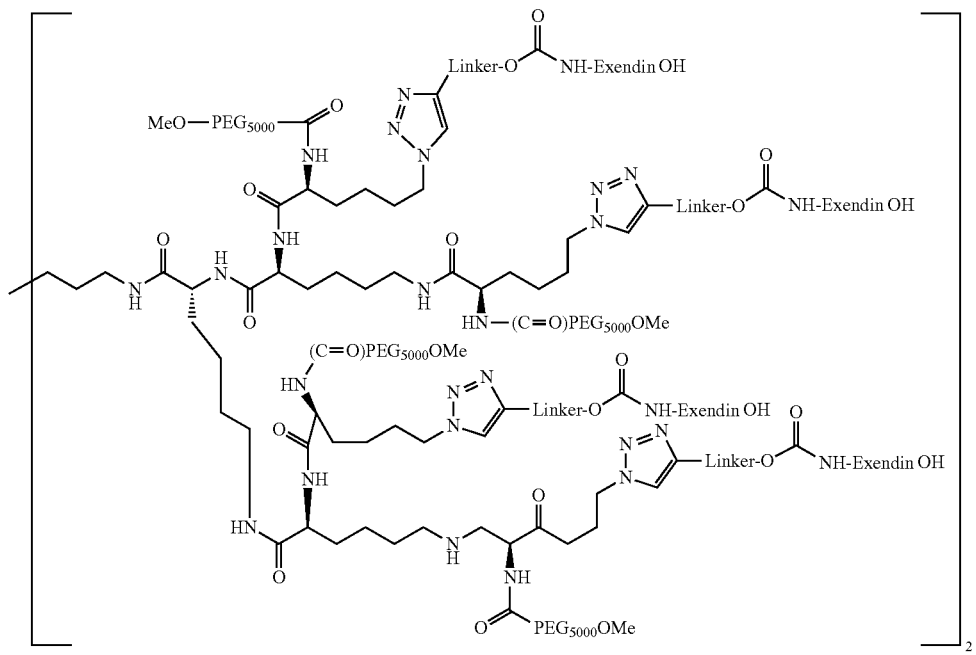

A solution of sodium ascorbate (1.5 M in water) is added to a blue mixture of 0.1 M CuSO$_4$ in water and 50 mM TBTA in dimethylsulfoxide (DMSO), and the resulting colorless solution is immediately added to a solution of 1 equivalent of the PEGylated azido dendrimer DAH[Lys]$_4$[NL]$_8$[mPEG$_{5000}$]$_8$ [N$_3$]$_8$ and 10 equivalents of alkynyl-linker-exendin in 1:2 water/DMSO. The mixture is allowed to react overnight, and is then dialyzed against water using a 10,000-mw cutoff dialysis membrane until HPLC analysis reveals complete removal of the uncoupled alkynyl-linker-exendin. The dialysate is lyophilized to provide the product.

Examples 17-20 describe synthesis of compounds of the invention wherein a drug is coupled to a polylysine dendrimer through a different linker, and wherein X is O and Y is absent.

Example 17

Boc-L-Propargylglycine Succinimidyl Ester (BOC-PG-OSu)

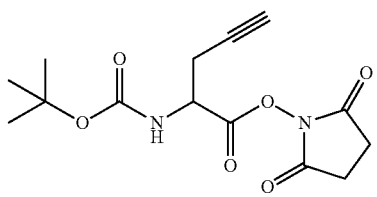 [SMILES: C#CCC(NC(=O)OC(C)(C)C)C(=O)ON1C(=O)CCC1=O]

To a stirred solution of N-(tert-butoxycarbonyl)-L-propargylglycine (1.8 mmol) and triethylamine (2.0 mmol) in tetrahydrofuran (10 mL) is added N,N'-disuccinimidyl carbonate (2.0 mmol). The reaction mixture is stirred at ambient temperature for 1.5 hours and is then concentrated on the roto-vap. The residue is taken up in ethyl acetate and washed with water, saturated sodium hydrogen carbonate solution and saturated sodium chloride solution. The organic phase is dried over magnesium sulfate and concentrated. Purification by silica gel chromatography provides the product. Fmoc-L-propargylglycine succinimidyl ester is prepared similarly, starting from Fmoc-L-propargylglycine.

Example 18

DAH[Lys]$_4$[BOC-PG]$_8$

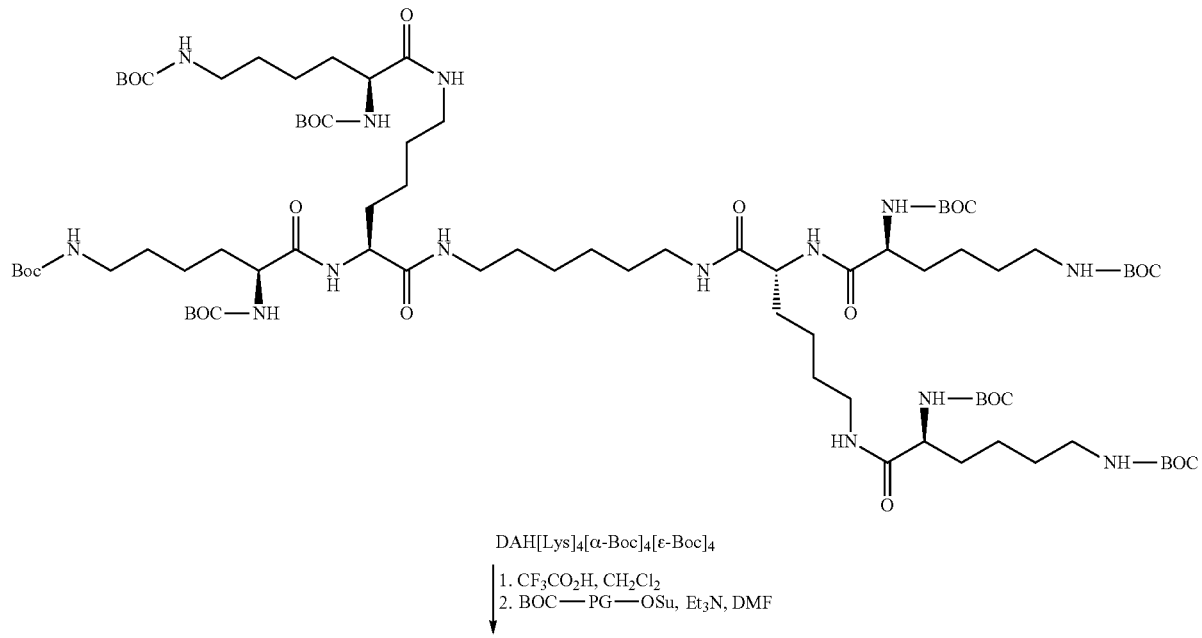

DAH[Lys]$_4$[α-Boc]$_4$[ε-Boc]$_4$

1. CF$_3$CO$_2$H, CH$_2$Cl$_2$
2. BOC—PG—OSu, Et$_3$N, DMF

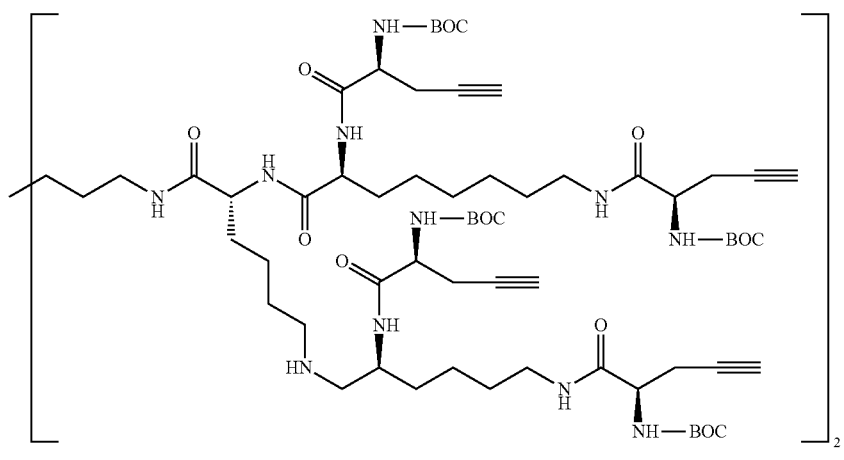

DAH[Lys]4[BOC-PG]8

Trifluoroacetic acid (4 mL) is added to a stirred suspension of DAH[Lys]$_4$-[α-Boc]$_4$[ε-Boc]$_4$ (0.139 g; 82.4 mmol) in dichloromethane (4 mL) and the resulting solution is stirred at ambient temperature for 1.5 hours. The solution is concentrated and the crude salt is taken up in N,N-dimethylformamide (4 mL) and triethylamine (368 μL; 2.7 mmol) added. To this solution is added a solution of Boc-L-propargylglycine succinimidyl ester (726 μmol) in N,N-dimethyl-formamide. The reaction mixture is stirred at room temperature for 22 hours and is then added by pipette to a stirred ice-water (200 mL) solution. The resulting suspension is stirred for 30 minutes and is then collected by filtration. The solid is washed with water and dried. It is re-suspended in acetonitrile (2 mL) and stirred for 30 minutes. The solid is collected, washed with acetonitrile and dried to give the product.

Example 19

DAH[Lys]$_4$[NL]$_8$[mPEG$_{5000}$]$_8$[Alkyne]$_8$

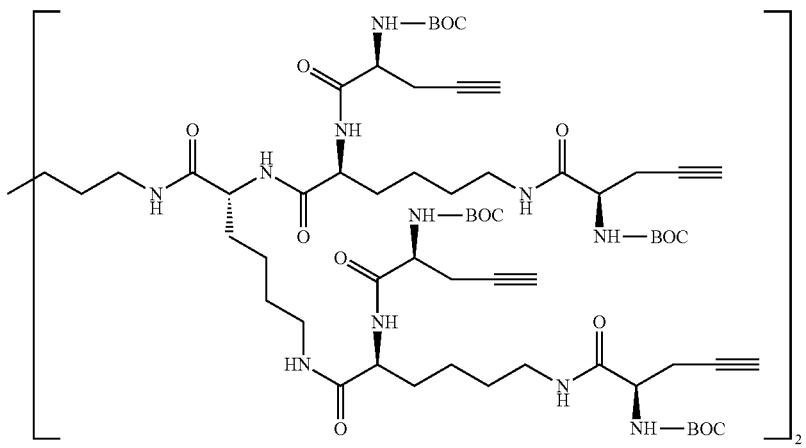

DAH[Lys]4[BOC—PG]8

1. CF$_3$CO$_2$H, CH$_2$Cl$_2$
2. mPEG(5000)-NHS, Et$_3$N, DMF

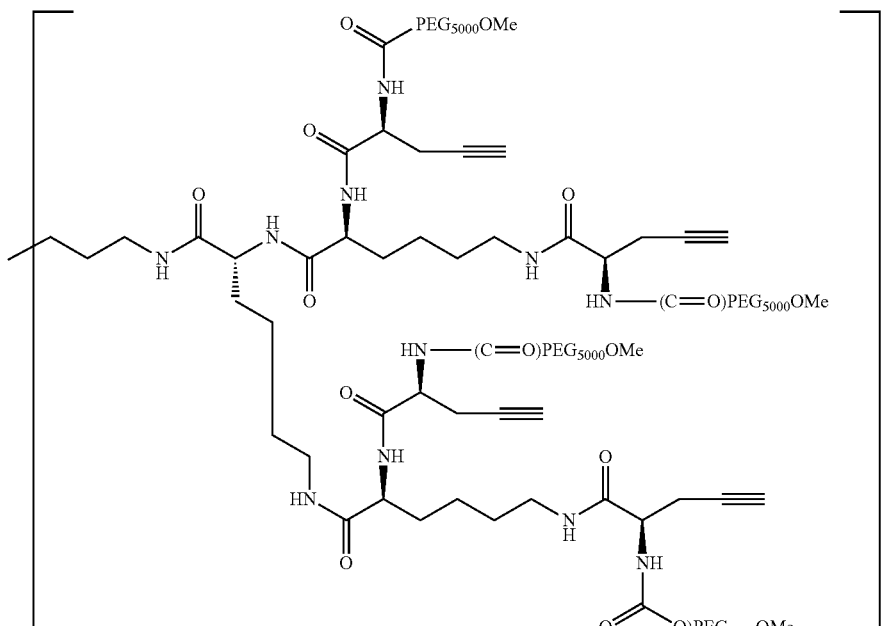

DAH[Lys]4[NL]8[mPEG$_{5000}$]8[alkyne]8

Trifluoroacetic acid is added to a stirred suspension of DAH[Lys]$_4$[BOC-PG]$_8$ in dichloromethane as described for other examples above and the resulting solution is stirred at ambient temperature for 1.5 hours. The solution is concentrated and the crude salt is taken up in N,N-dimethylformamide and triethylamine sufficient to neutralize the salts and allow subsequent coupling is added. To this solution is added a molar excess of monomethoxypolyethylene glycol succinimidyl ester (mw 5000) as a solution in N,N-dimethylformamide. The reaction mixture is stirred at room temperature for 22 hours and is then dialyzed against methanol using a 10,000-mw cutoff dialysis membrane to remove small molecule reagents and byproducts. The dialysate is evaporated to dryness to provide the product.

Example 20

Conjugation of Azido-Linker-Drug with DAH[Lys]$_4$[NL]$_8$[mPEG$_{5000}$]$_8$[Alkyne]$_8$ A solution of sodium ascorbate (1.5 M in water) is added to a blue mixture of 0.1 M CuSO$_4$ in water and 50 mM TBTA in dimethylsulfoxide (DMSO), and the resulting colorless solution is immediately added to a solution of 1 equivalent of the PEGylated alkyne dendrimer DAH[Lys]$_4$[NL]$_8$[mPEG$_{5000}$]$_8$

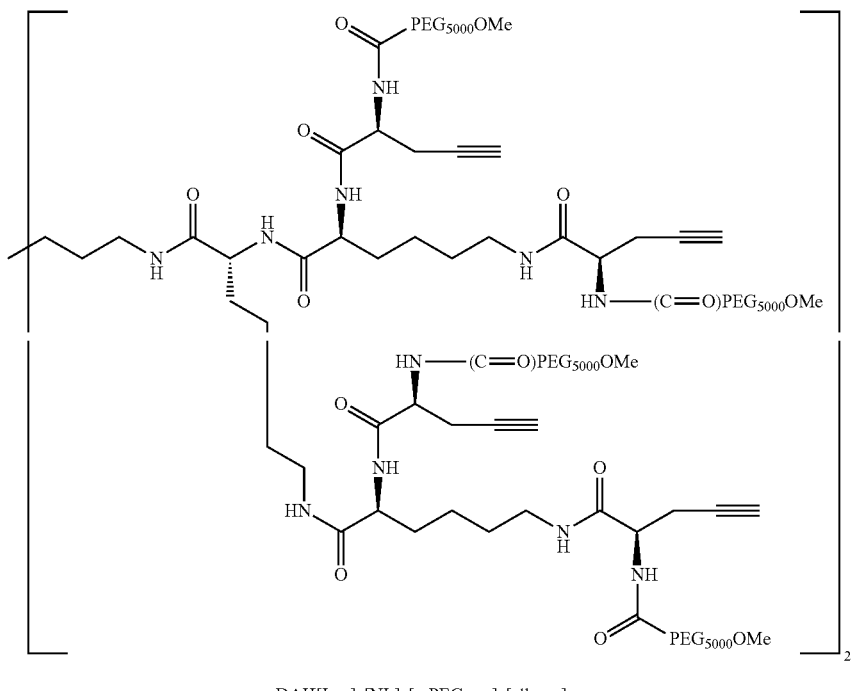

DAH[Lys]$_4$[NL]$_8$[mPEG$_{5000}$]$_8$[alkyne]$_8$

N$_3$-Linker-Drug
sodium ascorbate
CuSO$_4$, TBTA
DMSO/H$_2$O

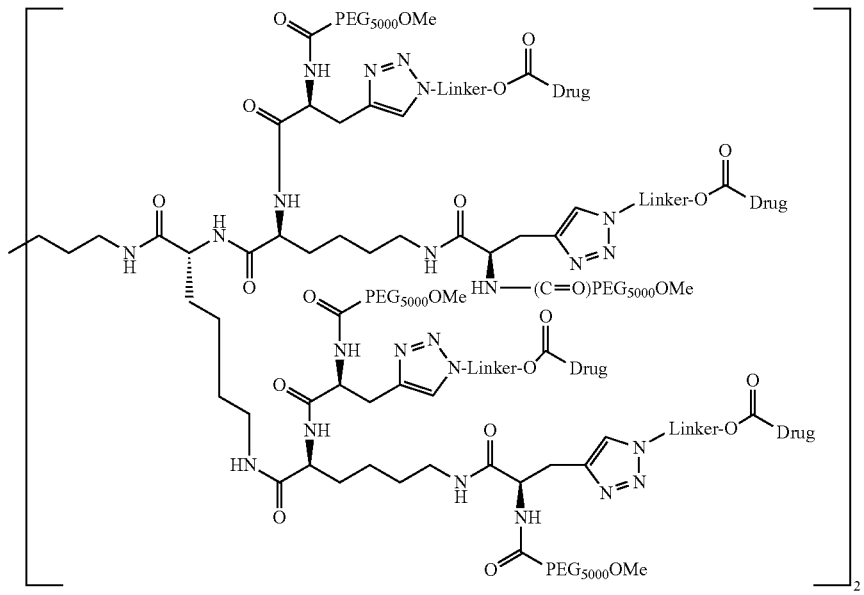

DAH[Lys]$_4$[NL]$_8$[mPEG$_{5000}$]$_8$[linker-drug]$_8$

[Alkyne]₈ and 10 equivalents of azido-linker-drug in 1:2 water/DMSO. The mixture is allowed to react overnight, and is then dialyzed against water until HPLC analysis reveals complete removal of the uncoupled alkynyl-linker-exendin. The dialysate is lyophilized to provide the product.

Examples 21-23 describe coupling of exendin to the polylysine through still a different linker, wherein X is O and Y is absent.

Example 21

Synthesis of an Example Azido-Linker Succinimidyl Carbonate

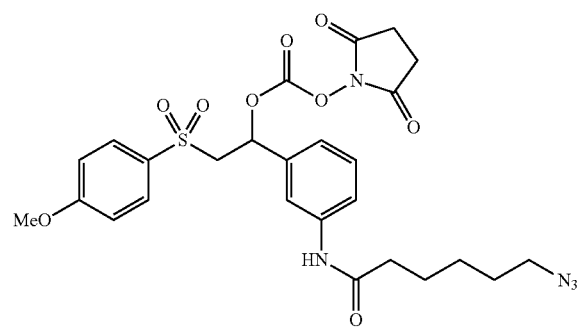 [SMILES: COc1ccc(S(=O)(=O)CC(OC(=O)ON2C(=O)CCC2=O)c2cccc(NC(=O)CCCCCN=[N+]=[N-])c2)cc1]

While the following procedure is given in detail for the 4-methoxyphenylsulfonyl trigger, other azido-linker succinimidyl carbonates comprising arylsulfonyl triggers may be prepared by substitution of 4-methoxythiophenol in Step 1 below with other substituted thiophenols.

Step 1. 2-Bromo-3'-nitroacetophenone (2.98 g, 12.2 mmol) was dissolved in acetonitrile (12 mL). Water (12 mL) then sodium hydrogen carbonate (2.04 g, 24.3 mmol) were added. The resulting biphasic mixture was vigorously stirred and 4-methoxythiophenol (1.5 mL, 12.2 mmol) was added dropwise over 5 minutes. The reaction mixture was stirred at room temperature for 1.5 hours. It was then diluted with water and extracted with ethyl acetate (×3). The combined organic extracts were washed with 1M sodium carbonate and saturated sodium chloride, they were then dried over magnesium sulfate and concentrated under reduced pressure to give an orange oil (3.85 g) which solidified on standing. To the crude material was added ethyl acetate/hexanes (1:4, 20 mL) and the mixture stirred overnight. The solid was collected, washed with ethyl acetate/hexanes (1:4) and dried to yield the sulfide (2.75 g, 74%) as a pale orange solid. ¹H NMR (DMSO-d6) δ3.733□s, 4.53 (2H, s), 6.86 (2H, d, J=8.4 Hz), 7.28 (2H, d, J=8.4 Hz), 7.80 (1H, t, J=8.0 Hz), 8.36 (1H, d, J=7.8 Hz), 8.45 (1H, m), 8.62 (1H, t, J=1.8 Hz).

Step 2. To an ice-cooled stirred solution of the sulfide of Step 1 (2.75 g, 9.07 mmol) in ethyl acetate (75 mL) was added peracetic acid (5.8 mL of a 32 wt % solution in dilute acetic acid, 27.6 mmol) slowly over 10 minutes. The solution was stirred at ice-bath temperature for 10 minutes and then at ambient temperature for 2 hours. The suspension was dissolved by the addition of ethyl acetate (75 mL) and this solution was washed with 1M sodium carbonate (×2), water, 0.1 M sodium hydrosulfite (×2), water, 1 M sodium carbonate and saturated sodium chloride. It was then dried over magnesium sulfate and concentrated under reduced pressure to furnish the sulfone as a white solid (3.04 g, 100%). ¹H NMR (DMSO-d6) δ3.843□s, 5.41 (2H, s), 7.09 (2H, d, J=8.8 Hz), 7.72 (2H, d, J=8.7 Hz), 7.80 (1H, t, J=7.9 Hz), 8.35 (1H, m), 8.47 (1H, ddd, J=0.9 Hz, J=2.3 Hz, J=8.2 Hz), 8.62 (1H, t, J=1.9 Hz).

Step 3. Tin (II) chloride dihydrate (2.69 g, 11.9 mmol) was added to a stirred suspension of the sulfone of Step 2 (1.00 g, 2.98 mmol) in ethanol (30 mL). The reaction mixture was heated at gentle reflux for 30 minutes and the resulting yellow solution allowed to cool to room temperature. The solution was poured onto crushed ice and the pH adjusted to pH 8 with 1 M sodium carbonate. The suspension was equilibrated to room temperature and diluted to ~200 mL volume with water. It was then extracted with ethyl acetate (×3) and the combined organic layers were washed with saturated sodium chloride, dried over magnesium sulfate and concentrated under reduced pressure to produce the aniline (0.813 g, 89%) as a yellow solid. ¹H NMR (DMSO-d6) δ3.823□s, 5.08 (2H, s), 5.36 (2H, br. s), 6.81 (1H, dt, J=1.9 Hz, J=7.2 Hz), 7.04-7.15 (5H, m), 7.79 (2H, d, J=8.8 Hz).

Step 4. To a stirred solution of 6-azidohexanoic acid and oxalyl chloride in anhydrous dichloromethane is added 2 drops of anhydrous N,N-dimethylformamide resulting in gas evolution. The solution is stirred for 15 minutes after which time gas evolution ceases and a further 2 drops of anhydrous N,N-dimethylformamide are added. The solution is stirred for 10 minutes and is then concentrated on the rotary evaporator. The crude acid chloride is dissolved in anhydrous dichloromethane and slowly added to a stirred suspension of the aniline of Step 3 and triethylamine in anhydrous dichloromethane. The resulting solution is stirred at room temperature for 2 hours and is then diluted with ethyl acetate. The solution is washed with water, 1 M sodium carbonate, water and saturated sodium chloride. It is dried over magnesium sulfate and concentrated under reduced pressure to give the crude amide. Purification utilizing a silica gel column provides the amide.

Step 5. To a stirred suspension of the amide of Step 4 in methanol is added in portions over 5 minutes sodium borohydride as described for the preparation of the alkynyl linkers above. The resulting solution is stirred for 35 minutes and then quenched by the addition of saturated ammonium chloride. It is then concentrated on the rotary evaporator, diluted with water and extracted with ethyl acetate (×3). The organic extracts are combined, washed with saturated sodium chloride and dried over magnesium sulfate. The solution is concentrated to afford the alcohol.

Step 6. Pyridine is added to a stirred solution of the alcohol of Step 5 and triphosgene in anhydrous tetrahydrofuran as described for the preparation of the alkynyl linkers above. The resulting suspension is stirred for 30 minutes and is then filtered and the filtrate concentrated under reduced pressure. The crude chloroformate is taken up in anhydrous tetrahydrofuran and N-hydroxysuccinimide followed by pyridine is added. The reaction mixture is stirred at ambient temperature for 35 minutes and is then filtered and concentrated. The residue is dissolved in ethyl acetate and washed with water, 0.1 M hydrochloric acid, saturated sodium hydrogen carbonate, water and saturated sodium chloride. The organic solution is dried over magnesium sulfate and concentrated under reduced pressure to yield the crude product. Purification by silica gel column chromatography affords the succinimidyl carbonate.

Example 22

Preparation of an Example Azido-Linker-Exendin-4 Compound

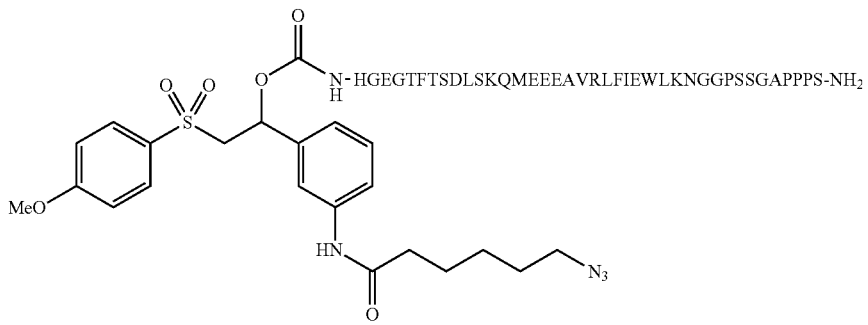

Rink amide-TentaGel resin containing the exendin-4 sequence (HGEGTFTSDLSKQ MEEEAV-RLFIEWLKNG-GPSSGAPPPS—NH$_2$) in protected form is prepared by solid-phase synthesis using standard FMOC/t-Bu solid-phase synthesis techniques. After removal of the last FMOC group and washing the resin three times with dichloromethane to remove excess piperidine, the resin is treated with a solution of 3 equivalents of the azido-Linker succinimidyl carbonate of Example 21 in dichloromethane/DMF and 1.5 equivalents of N-methylmorpholine. After coupling is completed, the resin is washed to remove excess reagents. The linker-exendin is removed from the resin and deblocked by treatment with a cocktail of trifluoroacetic acid, phenol, thioanisole, and 3,6-dioxa-1,8-octanedithiol. The linker-exendin is then purified by reversed-phase HPLC using a gradient of acetonitrile and water containing 0.1% trifluoroacetic acid, and lyophilized.

Example 23

Conjugation of Azido-Linker-Exendin with DAH [Lys]$_4$[NL]$_8$[mPEG$_{5000}$]$_8$[Alkyne]$_8$

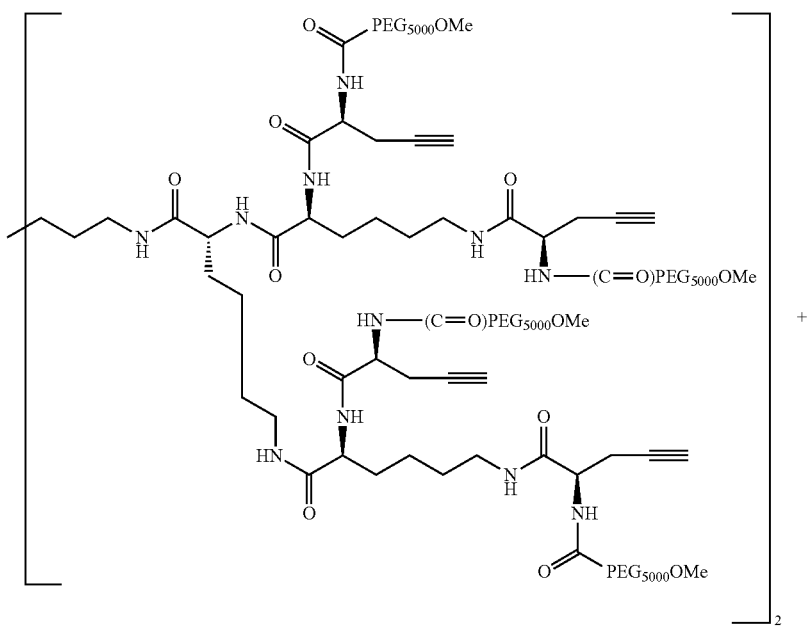

DAH[Lys]$_4$[NL]$_8$[mPEG$_{5000}$]$_8$[alkyne]$_8$

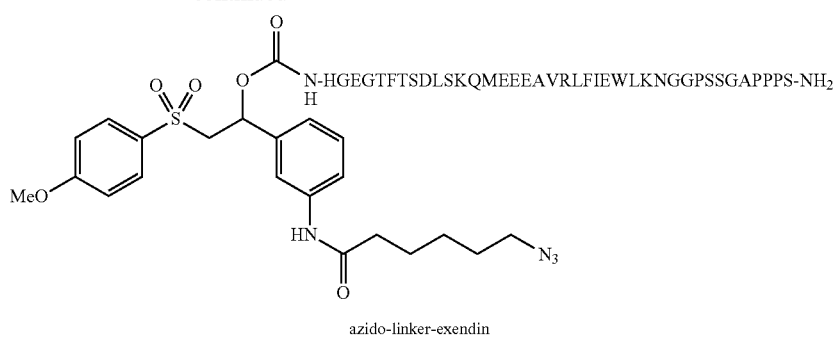
azido-linker-exendin
CuSO₄/TBTA
sodium ascorbate
DMSO/H₂O
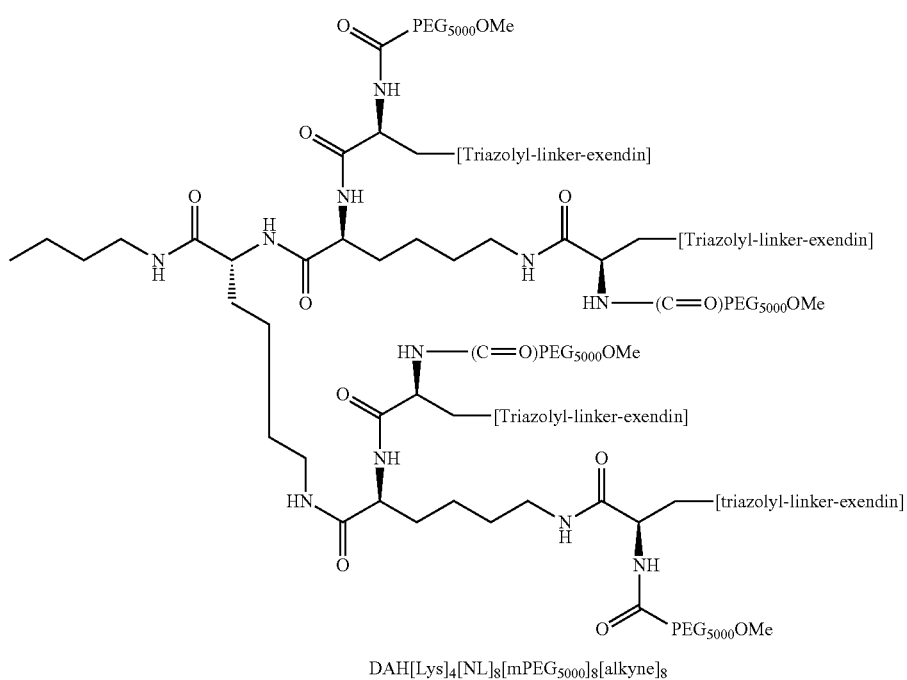
DAH[Lys]₄[NL]₈[mPEG₅₀₀₀]₈[alkyne]₈
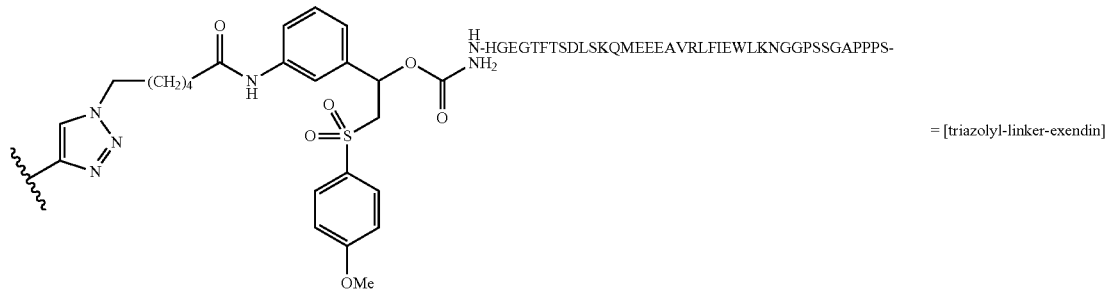
= [triazolyl-linker-exendin]

A solution of sodium ascorbate (1.5 M in water) is added to a blue mixture of 0.1 M CuSO$_4$ in water and 50 mM TBTA in dimethylsulfoxide (DMSO), and the resulting colorless solution is immediately added to a solution of 1 equivalent of the PEGylated alkyne dendrimer DAH[Lys]$_4$[NL]$_8$[mPEG$_{5000}$]$_8$[alkyne]$_8$ and 10 equivalents of azido-linker-exendin in 1:2 water/DMSO. The mixture is allowed to react overnight, and is then dialyzed against water until HPLC analysis reveals complete removal of the uncoupled alkynyl-linker-exendin. The dialysate is lyophilized to provide the product.

Examples 24-26 describe the preparation of a polylysine dendrimer coupled through an azido linker to SN38 wherein X is O and Y is NBCH$_2$.

Example 24

Preparation of an Azido-Linker Chloromethyl Carbamate O-((9-(2-(N-(6-azidohexanoyl)N-methyl)aminomethyl)fluorenyl)methyl)N-phenyl N-chloromethyl carbamate

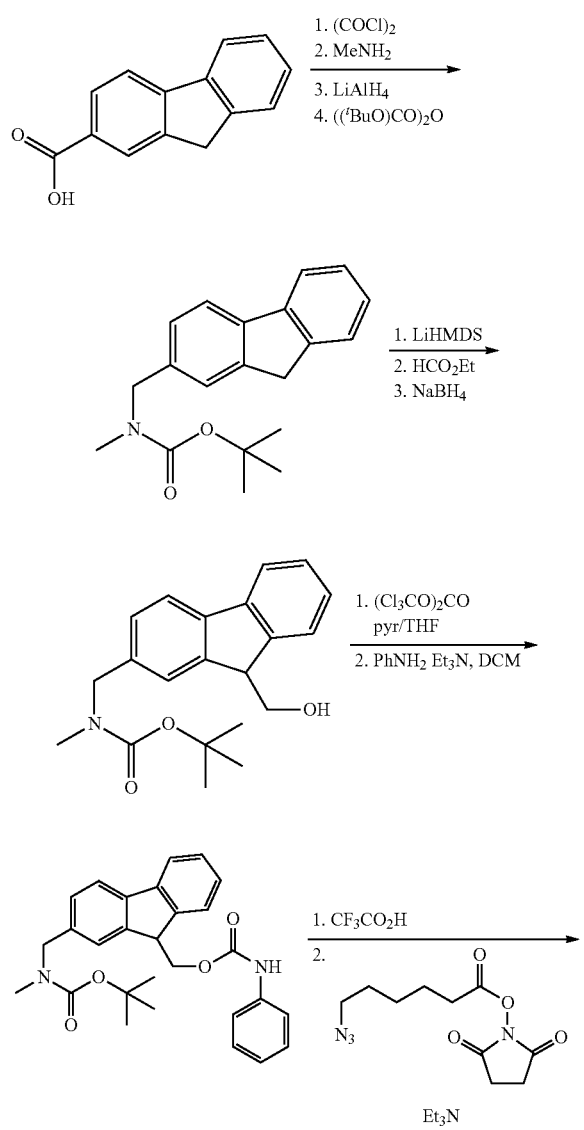

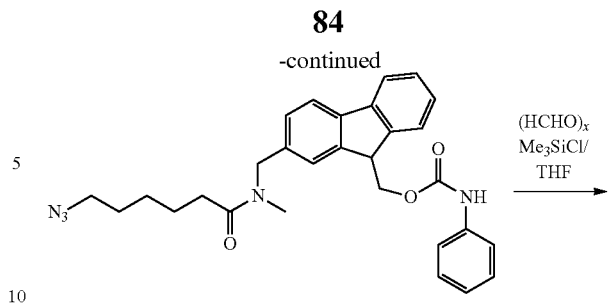

A solution of fluorene-2-carbonyl chloride (prepared from fluorene-2-carboxylic acid and oxalyl chloride) in THF is added to aqueous methylamine (2 molar equivalents) to prepare N-methyl fluorene-2-carboxamide. Reduction of the amide using LiAlH$_4$ in ether provides 2-((methylamino)methyl)fluorene. The amine is protected by reaction with di-tert-butyl dicarbonate to provide 2-((N-$^t$BOC—N-methylamino)methyl)fluorene.

A solution of the 2((N-$^t$BOC-N-methylamino)methyl)fluorene in anhydrous tetrahydrofuran (THF) is cooled to −78° C., then treated with a solution of lithium bis(trimethylsilyl)amide in THF (1.2 molar equivalents). After 1 hr, ethyl formate is added and the mixture is allowed to warm to ambient temperature. The mixture is diluted with ethyl acetate and washed successively with 0.1 N HCl, water, saturated aqueous NaHCO$_3$, and brine, then dried over MgSO$_4$, filtered, and evaporated to provide the 2-((N-$^t$BOC—N-methylamino)methyl)-fluorene-9-carboxaldehyde. This compound is dissolved in methanol and treated with NaBH$_4$ to provide 9-((2-((N-$^t$BOC—N-methylamino)methyl)fluorenylmethanol.

The 9-(2-((N-$^t$BOC-N-methylamino)methyl)fluorenylmethanol is dissolved in THF and treated with triphosgene and pyridine according to the general procedure of Example 2 to provide the chloroformate. The chloroformate is reacted with aniline according to the method of Example 3 to provide O-(9-(2-((N-$^t$BOC-N-methylamino)methyl)fluorenylmethyl)N-phenylcarbamate.

The carbamate is dissolved in trifluoroacetic acid to remove the $^t$BOC protecting group. After evaporation to dryness, the resulting amine is dissolved in THF and treated with N-(6-azidohexanoyl)succinimide and triethylamine (2 equivalents) to provide O-(9-(2-((N-(6-azidohexanoyl)-N-methylamino)methyl)fluorenylmethyl)N-phenylcarbamate.

Reaction of O-(9-(2-((N-(6-azidohexanoyl)-N-methylamino)methyl)fluorenylmethyl)N-phenylcarbamate with paraformaldehyde in 1:1 THF/chlorotrimethylsilane provides the product N-chloromethyl carbamate.

Example 25

Azido-Linker-Drug Compound with SN-38

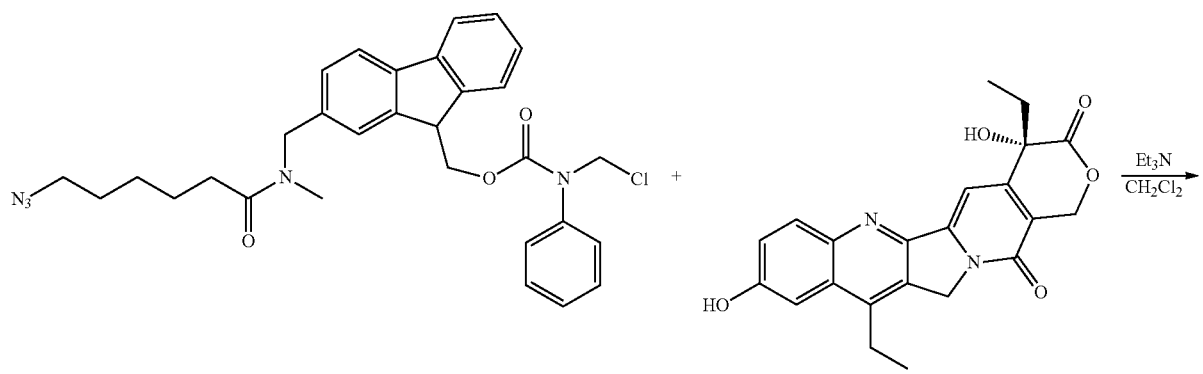

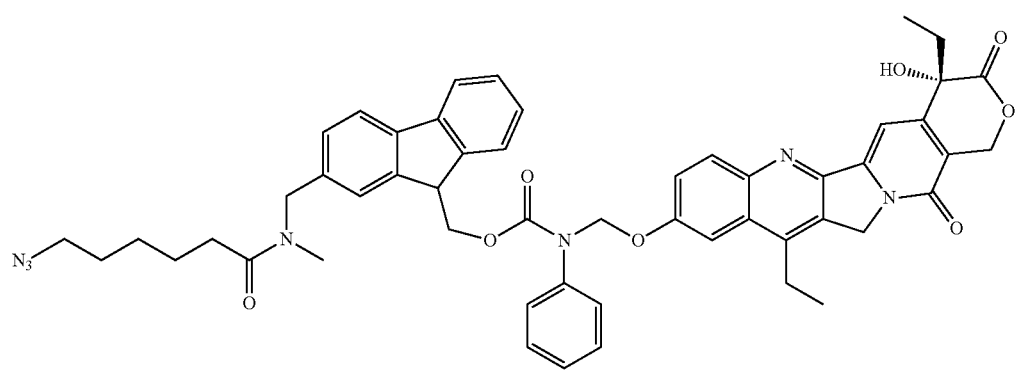

A suspension of the N-chloromethylcarbamate of Example 24 (2 equivalents) and sodium iodide (20 equivalents) in anhydrous acetone is allowed to stir overnight protected from light. The mixture is filtered and evaporated, and the residue is redissolved in anhydrous acetonitrile and added to a solution of SN-38 (1 equivalent) and triethylamine (1 equivalent). After stirring overnight protected from light, the mixture is evaporated to dryness. The residue is redissolved in ethyl acetate, washed with sat. aq. NH₄Cl, water, and brine, then dried over magnesium sulfate, filtered, and evaporated. The product is purified by silica gel chromatography.

Example 26
Conjugation of Azido-Linker-SN38 with DAH[Lys]$_4$[NL]$_8$[mPEG$_{5000}$]$_8$[Alkyne]$_8$
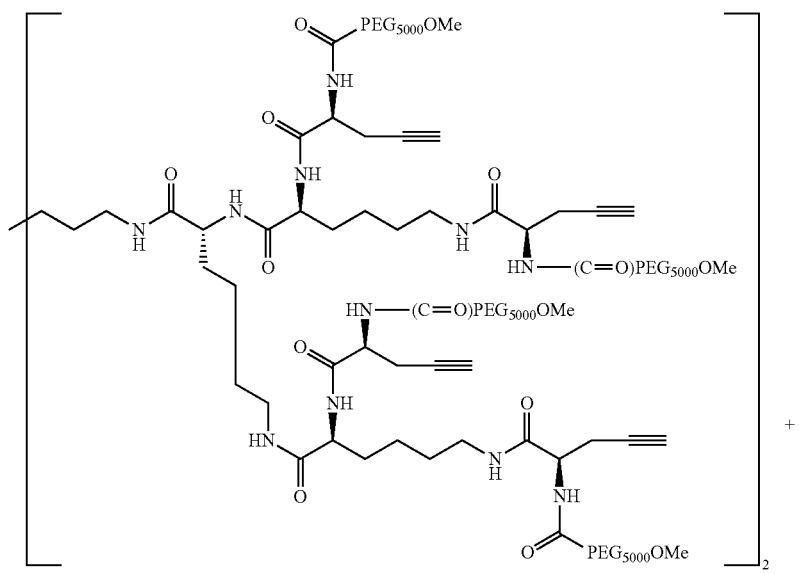
DAH[Lys]$_4$[NL]$_8$[mPEG$_{5000}$]$_8$[alkyne]$_8$
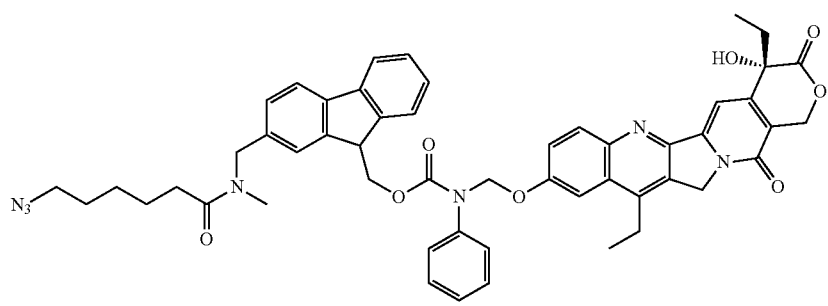
azido linker-SN38
CuSO$_4$/TBTA
sodium ascorbate
DMSO/H$_2$O

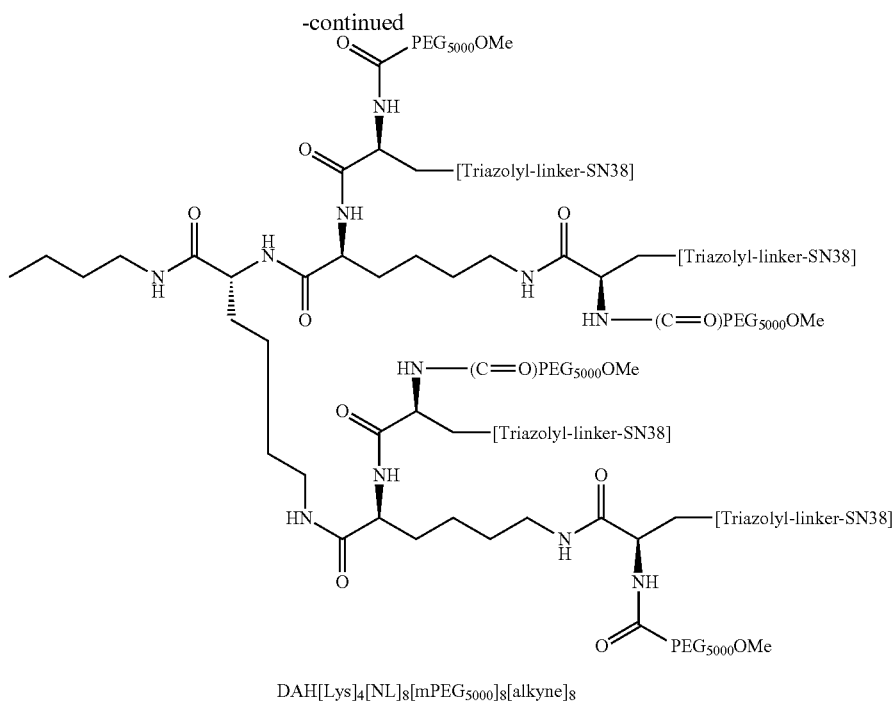

DAH[Lys]$_4$[NL]$_8$[mPEG$_{5000}$]$_8$[alkyne]$_8$

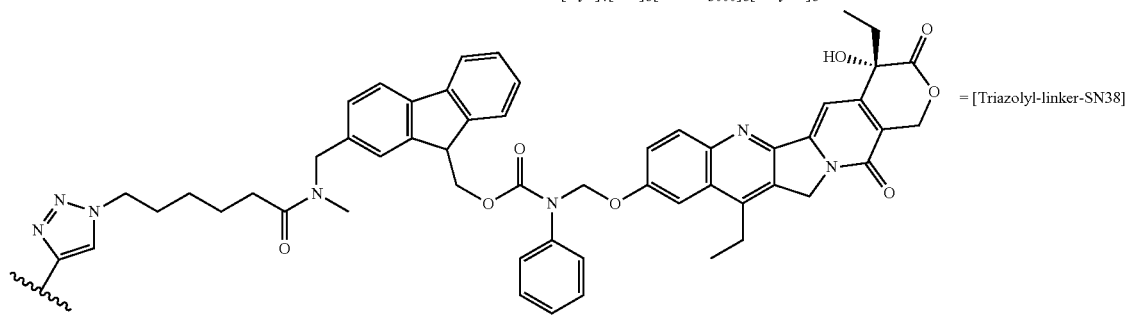

= [Triazolyl-linker-SN38]

A solution of sodium ascorbate (1.5 M in water) is added to a blue mixture of 0.1 M CuSO$_4$ in water and 50 mM TBTA in dimethylsulfoxide (DMSO), and the resulting colorless solution is immediately added to a solution of 1 equivalent of the PEGylated alkyne dendrimer DAH[Lys]$_4$[NL]$_8$[mPEG$_{5000}$]$_8$[alkyne]$_8$ and 10 equivalents of azido-linker-SN38 in 1:2 water/DMSO. The mixture is allowed to react overnight, and is then dialyzed against water until HPLC analysis reveals complete removal of the uncoupled alkynyl-linker-SN38. The dialysate is lyophilized to provide the product.

Example 27

N-(mPEG$_{5000}$-Oxycarbonyl)-L-Azidonorleucine Succinimidyl Ester

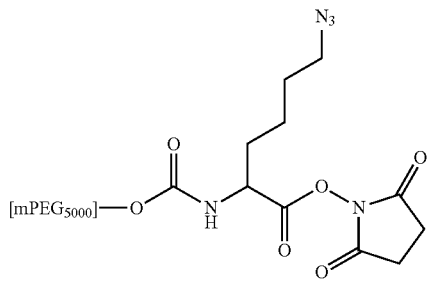

This example supports dendrimer assembly via dendrons in Example 28, method B.

Step 1. A solution of commercial monomethoxypolyethylene glycol succinimidyl carbonate (mw=5,000) in acetonitrile (1 equivalent) is added to a solution of L-azidonorleucine (1 equivalent) in 0.1 M aqueous NaHCO$_3$. After stirring at ambient temperature for 2 hrs, the mixture is acidified with CF$_3$CO$_2$H and evaporated to dryness to provide N-(mPEG$_{5000}$-oxycarbonyl)-L-azidonorleucine. The crude product is purified by precipitation from THF by addition of methyl tert-butyl ether.

Step 2. A solution of the N-(mPEG$_{5000}$-oxycarbonyl)-L-azidonorleucine from Step 1 in dry acetonitrile is treated with N,N'-disuccinimidyl carbonate (1.2 equivalents) and 4-(dimethylamino)pyridine (0.1 equivalent) until gas evolution ceases and a clear solution is obtained. Methyl tert-butyl ether is added to precipitate the PEGylated product, which is collected by vacuum filtration and dried.

Examples 28 and 29 describe preparation of dendrimers and coupling to alkynyl linker drugs, respectively.

Example 28

Solid-Phase Synthesis of Dendrimers

GLy[Lys]$_7$[NL]$_8$[mPEG$_{5000}$]$_8$[N$_3$]$_8$    5

Method A. Linear Synthesis

Step 1. H-Lys-Gly-Resin. TentaGel resin loaded with Fmoc-Glycine is deprotected by treatment with 20% piperidine in DMF, followed by washing the resin 3× with DMF to remove excess piperidine. The resin is treated with a DMF solution containing a 4-fold excess of HBTU-activated N$_\alpha$,N$_\epsilon$-bis(9-fluorenylmethoxycarbonyl)-L-lysine (Fmoc-Lys(Fmoc)-OH) and HOBt, and a 4-fold excess of N,N-diisopropylethylamine is added. Coupling proceeds for 4 hours. After washing the resin 3× with DMF, the resin is treated with 20% piperidine in DMF, followed by washing the resin 3× with DMF to remove excess piperidine.

Step 2. [H-Lys]$_2$-Lys-Gly-Resin. The resin from Step 1 is treated with a DMF solution containing an 8-fold excess of HBTU-activated N$_\alpha$,N$_\epsilon$-bis(9-fluorenylmethoxycarbonyl)-L-lysine (Fmoc-Lys(Fmoc)-OH) and HOBt, and an 8-fold excess of N,N-diisopropylethylamine is added. Coupling proceeds for 4 hours. After washing the resin 3× with DMF, the resin is treated with 20% piperidine in DMF, followed by washing the resin 3× with DMF to remove excess piperidine.

Step 3. [[H-Lys]$_2$-Lys]$_2$-Lys-Gly-Resin. The resin from Step 2 is treated with a DMF solution containing a 4-fold excess of HBTU-activated N$_\alpha$,N$_\epsilon$-bis(9-fluorenylmethoxycarbonyl)-L-lysine (Fmoc-Lys(Fmoc)-OH) and HOBt, and an 4-fold excess of N,N-diisopropylethylamine is added. Coupling proceeds for 4 hours. After washing the resin 3× with DMF, the resin is treated with 20% piperidine in DMF, followed by washing the resin 3× with DMF to remove excess piperidine.

Step 4. [[[ANL]$_2$-Lys]$_2$-Lys]$_2$-Lys-Gly-Resin. The resin from Step 3 is treated with a DMF solution containing a 4-fold excess of Fmoc-L-azidonorleucine succinimidyl ester, and an 4-fold excess of N,N-diisopropylethylamine is added. Coupling proceeds for 4 hours. After washing the resin 3× with DMF, the resin is treated with 20% piperidine in DMF, followed by washing the resin 3× with DMF to remove excess piperidine.

Step 5. [[[mPEG$_{5000}$-ANL]$_2$-Lys]$_2$-Lys]$_2$-Lys-Gly-Resin. The resin from Step 4 is treated with a DMF solution containing a 4-fold excess of monomethoxypolyethylene glycol propionate succinimidyl ester (mw 5000), and an 4-fold excess of N,N-diisopropylethylamine is added. Coupling proceeds for 4 hours. After washing the resin 3× with DMF, the resin is washed 3× with dichloromethane and dried under vacuum.

Step 6. The dendrimer is cleaved from the resin by treatment with CF$_3$CO$_2$H for 4 hours, followed by removal of the resin by filtration and evaporation to provide the dendrimer product.

Method B. Semi-Convergent Synthesis.

Steps 1-3 are as in Method A above.

Step 4. [[[mPEG$_{5000}$-ANL]$_2$-Lys]$_2$-Lys]$_2$-Lys-Gly-Resin. The resin from Step 3 is treated with a DMF solution containing a 4-fold excess of N-(mPEG$_{5000}$-oxycarbonyl)-L-azidonorleucine succinimidyl ester, and an 4-fold excess of N,N-diisopropylethylamine is added. Coupling proceeds for 4 hours.

Step 5. The dendrimer is cleaved from the resin by treatment with CF$_3$CO$_2$H for 4 hours, followed by removal of the resin by filtration and evaporation to provide the dendrimer product.

Example 29

Solid-Phase Conjugation of Alkynyl-Linker-Drugs and Dendrimers

Gly[Lys]$_7$[NL]$_8$[mPEG$_{5000}$]$_8$[triazolyl-linker-exendin]$_8$

A [[[mPEG$_{5000}$-ANL]$_2$-Lys]$_2$-Lys]$_2$-Lys-Gly-Resin from Example 28 (containing 8 equivalents of azido groups) and an alkynyl-linker-exendin compound (for example, that from Example 15 above) (10 equivalents) in 2:1 DMSO/water is treated with a fresh catalyst mixture prepared by addition of sodium ascorbate (1.5 M in water) to a mixture of 0.1 M CuSO$_4$ in water and 50 mM TBTA in dimethylsulfoxide (DMSO). The conjugation mixture is shaken overnight, and the resin is filtered and washed 3× with DMSO, 3× with water, 3× with methanol, and 3× with dichloromethane and dried under vacuum. The dendrimer is cleaved from the resin by treatment with CF$_3$CO$_2$H for 4 hours, followed by removal of the resin by filtration and evaporation to provide the crude product, which is dialyzed against water to remove small-molecule contaminants. The dialysate is lyophilized to provide the product.

Examples 30-34 Describe Preparation of Formula (1) without Linkage to Dendrimer Using Fluorescein as Model Drug—i.e., Compounds of the Formula

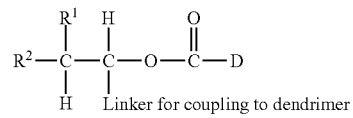

wherein D = fluorescein as a model for drug

Example 30

Preparation of 6-Azidohexanal (1) 6-azido-1-hexanol: a mixture of 6-chloro-1-hexanol (25 g, 183 mmol) and sodium azide (32.5 g, 500 mmol) in 200 mL of water was heated at reflux for 20 h, then cooled to ambient temperature and extracted 3× with ethyl acetate. The combined extracts were washed with brine, dried over MgSO$_4$, filtered, and concentrated to yield the product as a pale yellow oil (28.3 g).

(2) 6-azidohexanal: Solid trichloroisocyanuric acid (4.3 g) was added in small portions to a vigorously stirred mixture of 6-azido-1-hexanol (7.15 g) and sodium bicarbonate (5.0 g) in dichloromethane (100 mL) and water (10 mL). The mixture was stirred for an additional 30 minutes after addition, then filtered through a pad of Celite™. The organic phase was separated and washed successively with sat. aq. NaHCO$_3$ and brine, then dried over MgSO$_4$, filtered, and concentrated to provide the product (5.8 g), which was used without further purification.

Example 31

Preparation of Azidoalcohols of the Formula

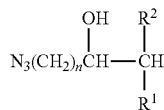

In these reactions, R$^a$ in R$^a$CH$_3$ contains the trigger present in the final product,

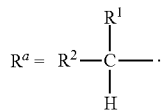

A 1.6 M solution of n-butyllithium (3.1 mL, 5.0 mmol) in hexane was added dropwise to a stirred solution of R$^a$—CH$_3$ (5.0 mmol) in anhydrous tetrahydrofuran (THF) (15 mL) cooled to −78° C. After addition, the cooling bath was removed and the mixture was allowed to warm slowly to 0° C. over approximately 30 min. The mixture was then cooled back to −78° C., and 6-azidohexanal from Example 30 (5.5 mmol) was added. After stirring for 15 minutes, the cooling bath was removed and the mixture was allowed to warm. At the point where the mixture became clear, 5 mL of saturated aq. NH$_4$Cl was added and the mixture was allowed to continue warming to ambient temperature. The mixture was diluted with ethyl acetate and washed successively with water and brine, and then dried over MgSO$_4$, filtered, and evaporated to provide the crude product as an oil. Chromatography on silica gel using a gradient of ethyl acetate in hexane provided the purified products.

Compounds prepared according to this method include:
1-(4-(trifluoromethyl)phenylsulfonyl)-7-azido-2-heptanol

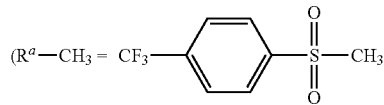

(trifluoromethyl)phenyl methyl sulfone);
1-(4-chlorophenylsulfonyl)-7-azido-2-heptanol (R—CH$_3$=4-chlorophenyl methyl sulfone);
1-(phenylsulfonyl)-7-azido-2-heptanol (R—CH$_3$=phenyl methyl sulfone);
1-(4-methylphenylsulfonyl)-7-azido-2-heptanol (R—CH$_3$=4-methylphenyl methyl sulfone);
1-(4-methoxyphenylsulfonyl)-7-azido-2-heptanol (R—CH$_3$=4-methoxyphenyl methyl sulfone);
1-(2,4,6-trimethylphenylsulfonyl)-7-azido-2-heptanol (R—CH$_3$=2,4,6-trimethylphenyl methyl sulfone);
1-(morpholinosulfonyl)-7-azido-2-heptanol (R—CH$_3$=4-(methylsulfonyl)-morpholine);
1-(methanesulfonyl)-7-azido-2-heptanol (R—CH$_3$=dimethyl sulfone);
1-cyano-7-azido-2-heptanol (R—CH$_3$=4-acetonitrile);
1-(morpholinocarbonyl)-7-azido-2-heptanol (R—CH$_3$=4-acetylmorpholine); and
1-(9-fluorenyl)-6-azido-1-hexanol ("R—CH$_3$"=fluorene).

Example 32

Preparation of Azido-Linker Chloroformates

Pyridine (160 µL) was added dropwise to a stirred solution of the azidoalcohol of Example 31 (1.0 mmol) and triphosgene (500 mg) in 15 mL of anhydrous THF. The resulting suspension was stirred for 10 minutes, then filtered and concentrated to provide the crude chloroformate as an oil.

Compounds prepared according to this method include:
1-(4-(trifluoromethyl)phenylsulfonyl)-7-azido-2-heptyl chloroformate
1-(4-chlorophenylsulfonyl)-7-azido-2-heptyl chloroformate;
1-(phenylsulfonyl)-7-azido-2-heptyl chloroformate;
1-(4-methylphenylsulfonyl)-7-azido-2-heptyl chloroformate;
1-(4-methoxyphenylsulfonyl)-7-azido-2-heptyl chloroformate;
1-(2,4,6-trimethylphenylsulfonyl)-7-azido-2-heptyl chloroformate;
1-(morpholinosulfonyl)-7-azido-2-heptyl chloroformate;
1-(methanesulfonyl)-7-azido-2-heptyl chloroformate;
1-cyano-7-azido-2-heptyl chloroformate;
1-(morpholinocarbonyl)-7-azido-2-heptyl chloroformate; and
1-(9-fluorenyl)-6-azido-1-hexyl chloroformate.

Also prepared according to this method was 6-azidohexyl chloroformate, starting from 6-azidohexanol.

Example 33

Preparation of Azido-Linker Hydroxysuccimidyl CHS) Carbonates

A solution of the chloroformate from Example 32 in 15 mL of dry THF was treated successively with N-hydroxysuccinimide (350 mg) and pyridine (250 µL) for 10 minutes. The mixture was then concentrated, and the residue was redissolved in ethyl acetate. After washing with 0.1 N HCl, water, sat. NaHCO$_3$, water, and brine, the solution was dried over MgSO$_4$, filtered, and evaporated. In some cases, the HS carbonate spontaneously crystallized, and was recrystallized from ethyl acetate/hexane. In other cases, the crude HS carbonate was first chromatographed on silica gel using a gradient of ethyl acetate in hexane, followed by crystallization. All compounds were crystalline with the exception of that obtained from 1-(methanesulfonyl)-7-azido-2-heptanol.

Compounds prepared according to this method include:
O-[1-(4-(trifluoromethyl)phenylsulfonyl)-7-azido-2-heptyl]-O'-succinimidyl carbonate;
O-[1-(4-chlorophenylsulfonyl)-7-azido-2-heptyl]-O'-succinimidyl carbonate;
O-[1-(phenylsulfonyl)-7-azido-2-heptyl]-O'-succinimidyl carbonate;
O-[1-(4-methylphenylsulfonyl)-7-azido-2-heptyl]-O'-succinimidyl carbonate;
O-[1-(4-methoxyphenylsulfonyl)-7-azido-2-heptyl]-O'-succinimidyl carbonate;
O-[1-(2,4,6-trimethylphenylsulfonyl)-7-azido-2-heptyl]-O'-succinimidyl carbonate;
O-[1-(morpholinosulfonyl)-7-azido-2-heptyl]-O'-succinimidyl carbonate;

O-[1-(methanesulfonyl)-7-azido-2-heptyl]-O'-succinimidyl carbonate;

O-[1-cyano-7-azido-2-heptyl]-O'-succinimidyl carbonate;

O-[1-(morpholinocarbonyl)-7-azido-2-heptyl]-O'-succinimidyl carbonate; and

O-[1-(9-fluorenyl)-6-azido-1-hexyl]-O'-succinimidyl carbonate.

Also prepared according to this method was O-[6-azidohexyl]-O'-succinimidyl carbonate, starting from 6-azidohexyl chloroformate.

Example 34

Preparation of Linked Fluoresceins of the Formula

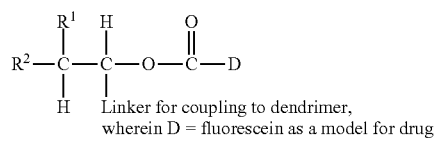

Linker for coupling to dendrimer, wherein D = fluorescein as a model for drug

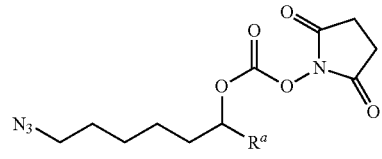

+

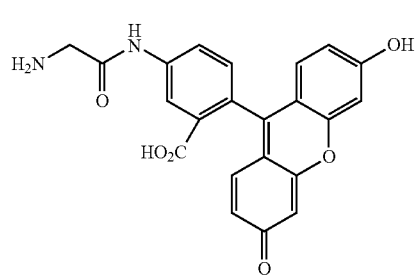

→

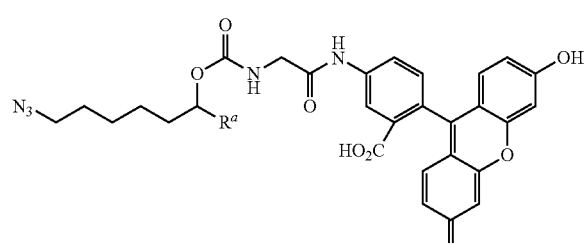

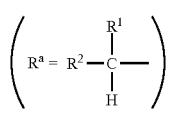

A solution of 25 mM azide-linker-HS of Example 33 in DMSO (100 μL) was added to a 10 mg/mL solution of 5-(aminoacetamido)fluorescein (Invitrogen) in DMSO (115 μL). After 1 h at ambient temperature, the mixture was analyzed by reversed-phase HPLC, indicating complete consumption of azide-linker-HS and formation of a single linked fluorescein product. The solutions were used without purification.

Examples 35-42 Describe the Preparation of PEGylated Dendrimer

Example 35

Preparation of Boc-Lys(Boc)-HEGA

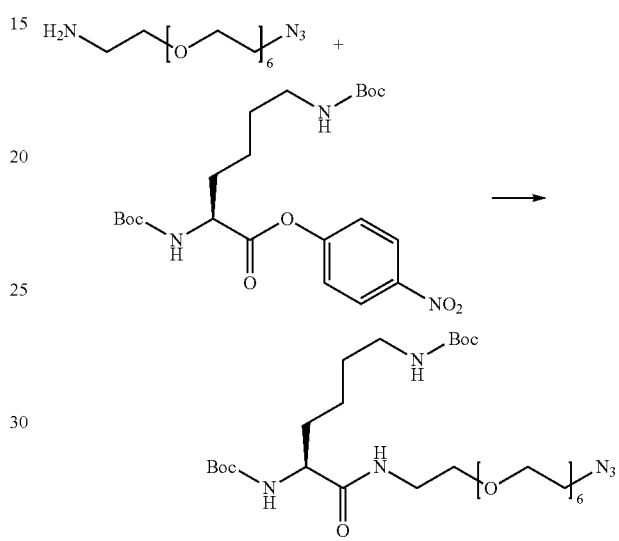

A solution of 20-azido-3,6,9,12,15,18-hexaoxaicosan-1-amine (362 mg, 1.0 mmol) in THF (5 mL) was added to a solution of $N_\alpha,N_\epsilon$-bis(tert-butoxycarbonyl)-L-lysine 4-nitrophenyl ester {Boc-Lys(Boc)-OPNP} (580 mg, 1.2 mmol) in THF (5 mL) followed by $Et_3N$ (288 μL, 209 mg, 2.1 mmol). The resulting mixture was allowed to stir for 2 h, then 1 N NaOH (3 mL) was added. Stirring was continued for 1.5 h, then the THF was removed under vacuum. The resulting suspension was extracted with ethyl acetate. The extract was washed with 0.5 N NaOH and water, then dried over $MgSO_4$, filtered and concentrated to dryness to give the product (610 mg) as a pale yellow oil.

Example 36

Preparation of H-Lys-HEGA

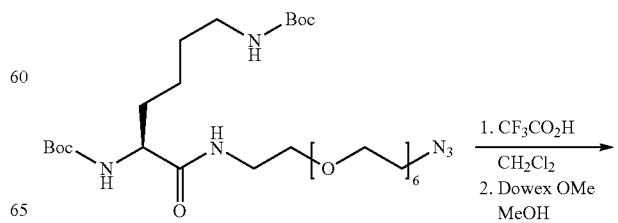

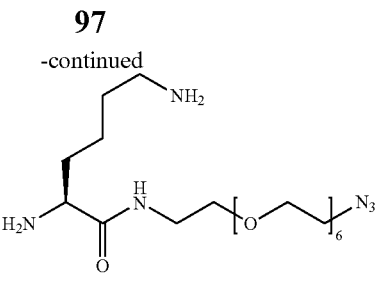

Trifluoroacetic acid (5 mL) was added to a solution of Boc-Lys(Boc)-HEGA (Example 35, 600 mg, 0.88 mmol) in dichloromethane (5 mL). The resulting mixture was allowed to stir at room temperature for 1.5 h. The mixture was then concentrated under reduced pressure to give 1310 mg of residue estimated to comprise 890 mg of free trifluoroacetic acid. This material was dissolved in methanol (25 mL) and treated with 24 mL of methanol-washed Dowex® (Dow Chemical Co.) Monosphere™ 550A for 0.5 h. The resin was removed by filtration, and the filtrate was concentrated to dryness to give the product (420 mg) as a viscous clear oil.

Example 37

Preparation of [Boc-Lys(Boc)]$_2$Lys-HEGA

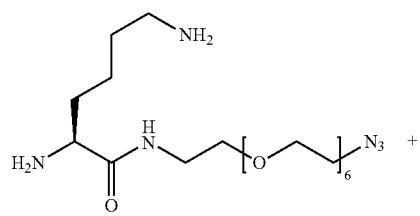

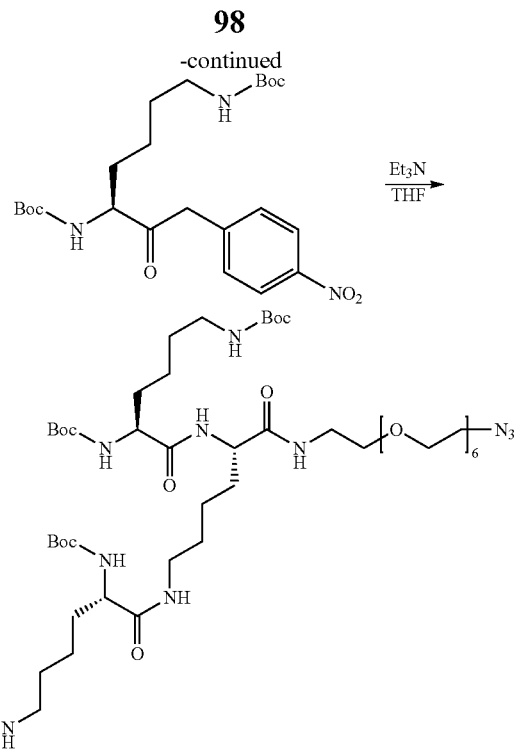

To a solution of H-Lys-HEGA (Example 36, 400 mg, 0.836 mmol) in THF (6 mL) was added Boc-Lys(Boc)-OPNP (938 mg, 2.0 mmol) followed by Et$_3$N (466 μL, 338 mg, 3.3 mmol). The resulting mixture was allowed to stir for 6.5 h, then 1 N NaOH was added (4 mL). Stirring was continued for 4 h. The resulting suspension was diluted with ethyl acetate (100 mL). The extract was washed with 0.5 N NaOH, then with 0.1 N HCl, then water, then dried over MgSO$_4$ and concentrated to dryness to give the product (722 mg, 76%) as sticky white solid.

Example 38

Preparation of [Lys]$_2$Lys-HEGA

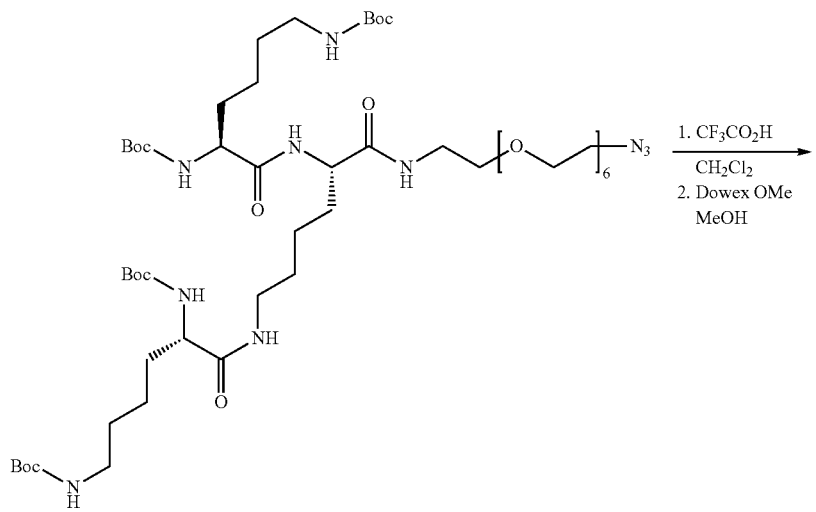

-continued

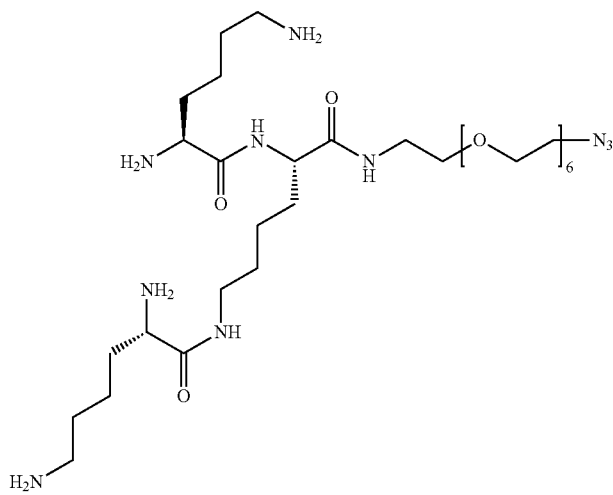

Trifluoroacetic acid (3 mL) was added to a solution of [Boc-Lys(Boc)]$_2$Lys-HEGA (Example 37, 499 mg, 0.44 mmol) in dichloromethane (3 mL). The resulting mixture was allowed to stir at room temperature for 3.5 h. The mixture was then concentrated under reduced pressure to give 1120 mg of residue estimated to comprise ~800 mg of free trifluoroacetic acid. This material was dissolved in methanol (20 mL) and treated with 20 mL of methanol washed Dowex® (Dow Chemical Co.) Monosphere™ 550A for 20 min. The resin was removed by filtration, and the filtrate was concentrated to dryness to give the product (323 mg) as a pale yellow oil.

Example 39

Preparation of [Boc-Lys(Boc)]$_4$[Lys]$_2$Lys-HEGA

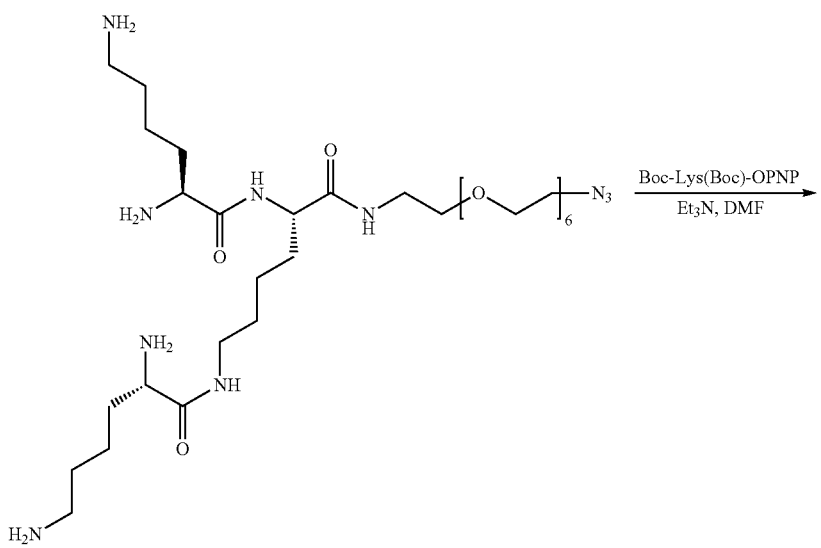

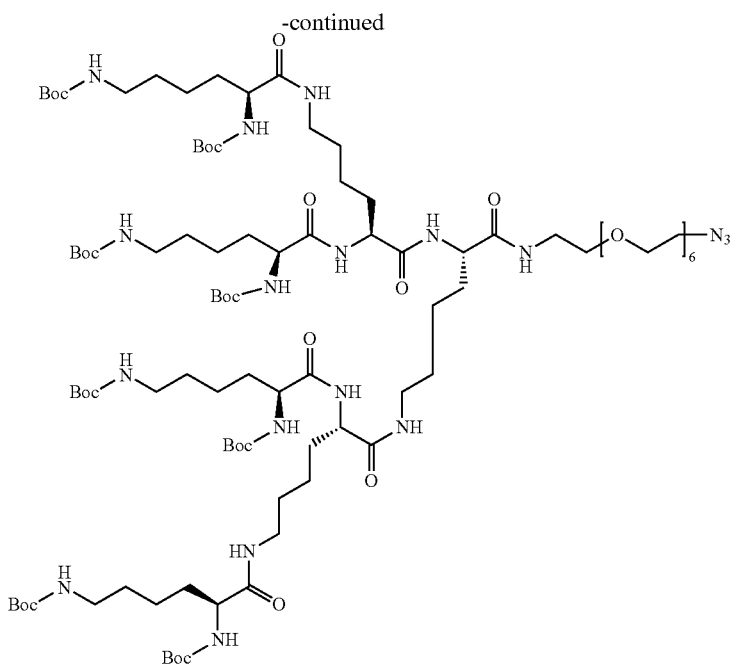

To a solution of [Lys]₂Lys-HEGA (Example 38, 300 mg, 0.41 mmol) in DMF (10 mL) was added Boc-Lys(Boc)-OPNP (916 mg, 2.0 mmol, 4.9 equiv) followed by Et₃N (455 μL, 330 mg, 3.3 mmol). The resulting mixture was allowed to stir for 23 h, then 1 N NaOH was added (4 mL). Stirring was continued for 3 h. The resulting suspension was diluted with ethyl acetate (150 mL). The extract was washed with 0.5 N NaOH, then with 0.1 N HCl, then water, then brine, then dried over MgSO₄, filtered and concentrated to dryness to give the product (730 mg, 87%) as white solid.

Example 40

Preparation of [Lys]₄[Lys]₂Lys-HEGA

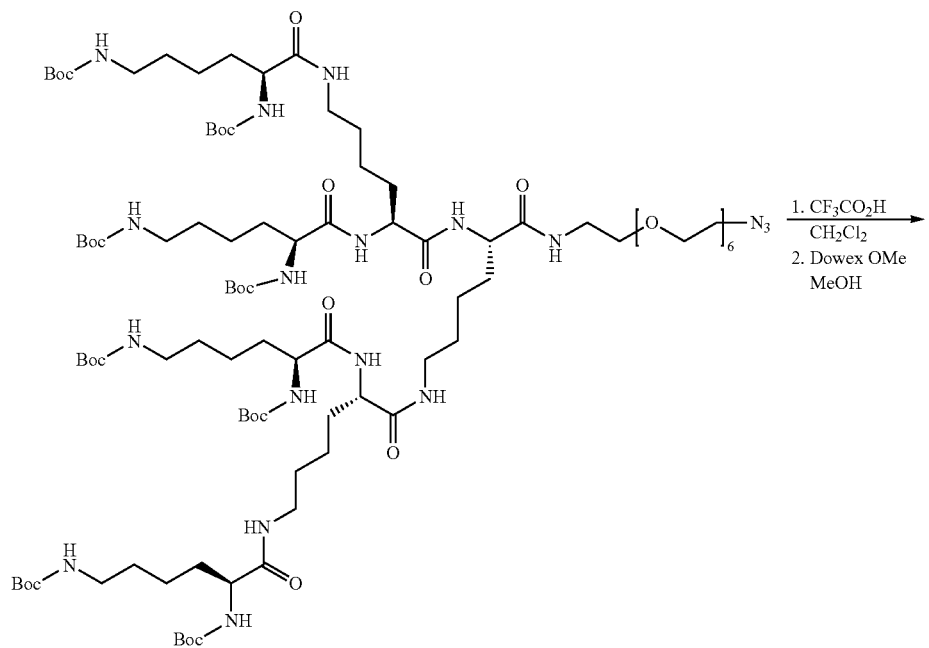

-continued

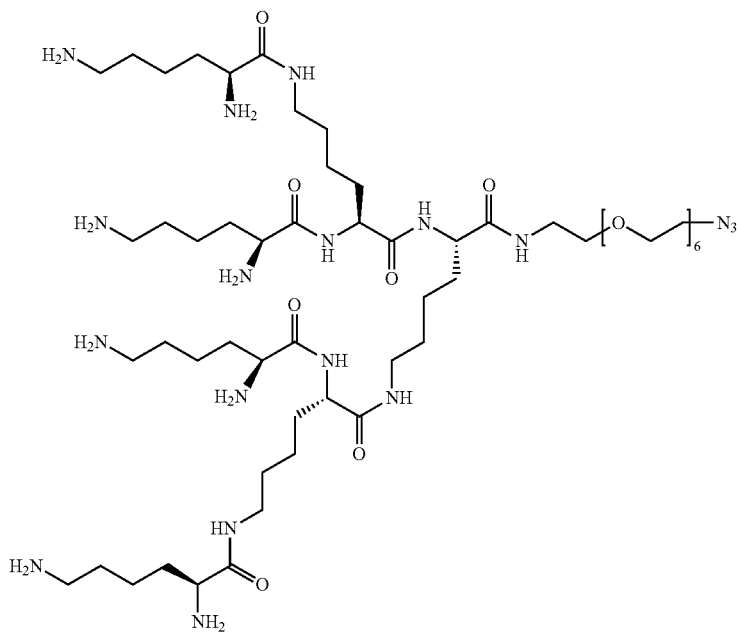

Trifluoroacetic acid (4 mL) was added to a solution of [Boc-Lys(Boc)]$_4$[Lys]$_2$Lys-HEGA (Example 39, 200 mg) in dichloromethane (4 mL). The resulting mixture was allowed to stir at room temperature for 1.5 h. The mixture was then concentrated under reduced pressure to give 786 mg of residue estimated to comprise ~664 mg of free trifluoroacetic acid. This material was dissolved in methanol (30 mL) and treated with 20 mL of methanol washed Dowex® (Dow Chemical Co.) Monosphere™ 550A (strong base anion exchange resin) for 30 min. The resin was removed by filtration, and the filtrate was concentrated to dryness to give the product (120 mg) as a sticky white solid.

Example 41

[Lys]$_4$[Lys]$_2$Lys-HEG-[mPEG$_{40kD}$]

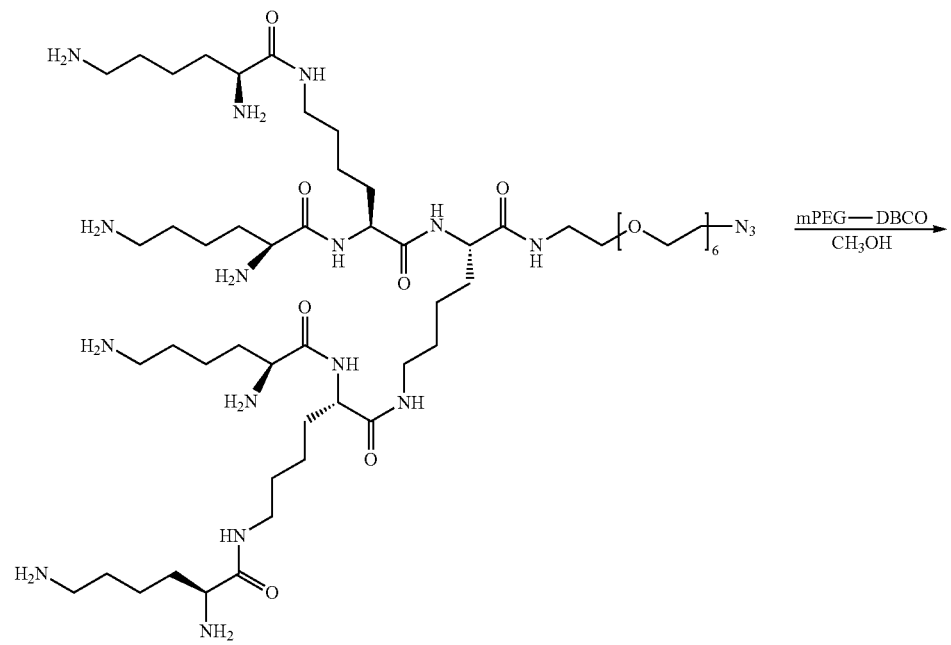

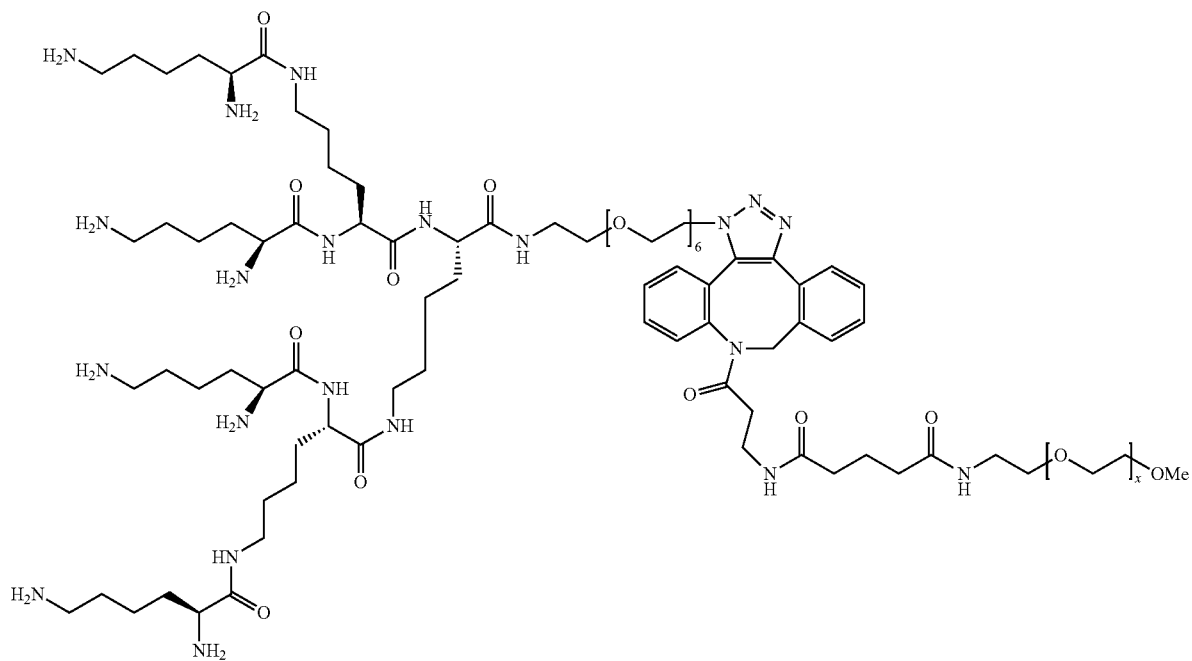

A 1.8 mM solution of [Lys]$_4$[Lys]$_2$Lys-HEGA (Example 40) in methanol (1.1 mL, 2 μmol) was mixed with a 1.2 mM solution of linear mPEG$_{40kD}$-DBCO (DBCO is a linking group, see Example 58) in methanol (0.825 mL, 1 μmol). The resulting mixture was allowed to stir for 6 h, dialyzed against methanol (Spectra/Por® (Spectrum Laboratories) 2 membrane; 12-14 kDa-cutoff), and concentrated to dryness to give the PEGylated dendrimer (39 mg) as a white solid.

Example 42

Preparation of [DBCO-Lys(DBCO)]$_4$[Lys]$_2$Lys-HEG-[mPEG$_{40kD}$]

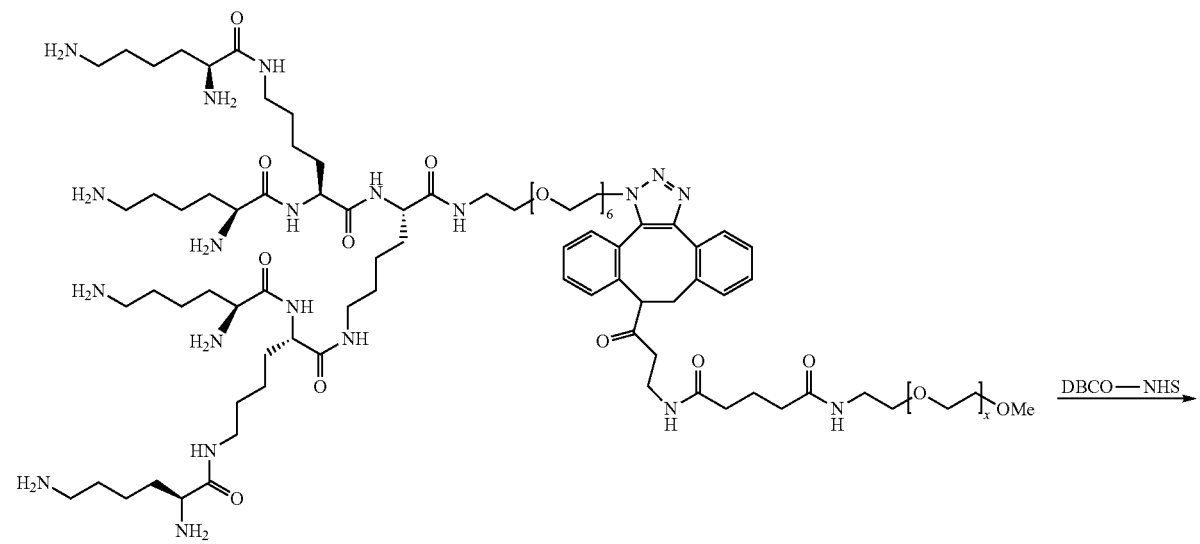

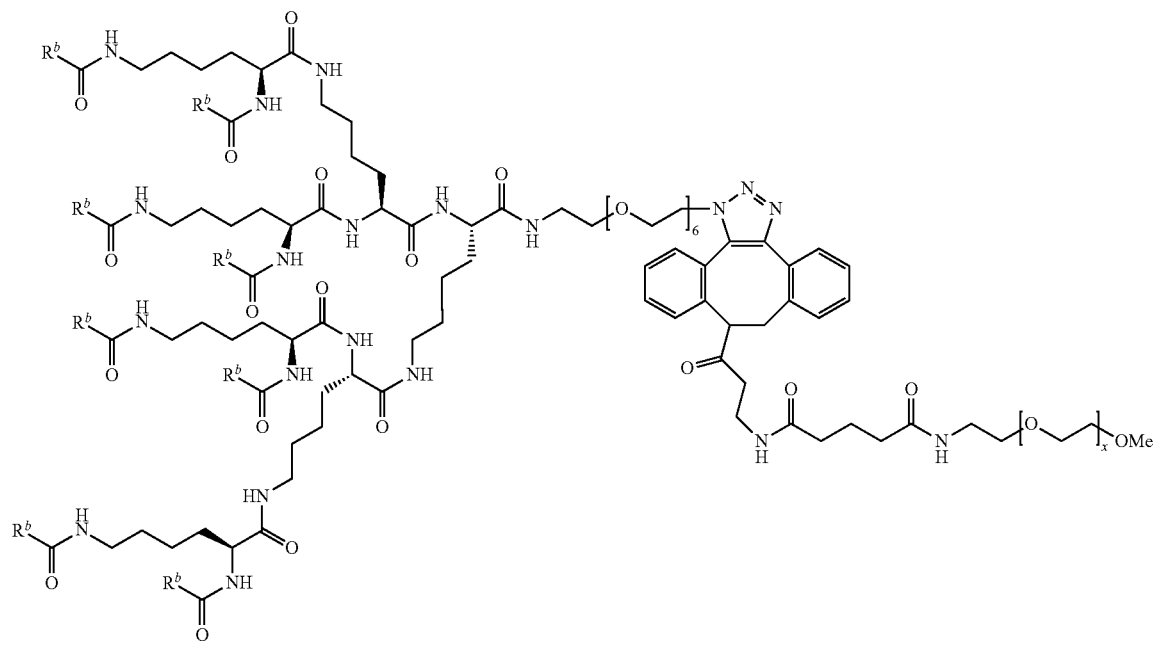

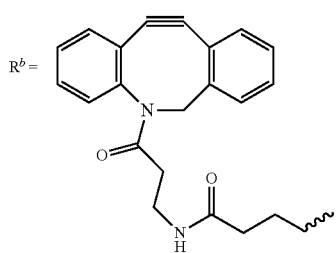

A 9.1 mM solution of DBCO—NHS (Click Chemistry Tools, 1660 μL, 15.1 μmol) was added to a solution of [Lys]$_4$[Lys]$_2$Lys-HEG-[mPEG$_{40kD}$] (Example 41, 39 mg, 0.946 μmol) in THF (1.9 mL). After stirring for 24 h the reaction mixture was diluted with methanol (4 mL), and dialyzed twice against methanol using a Spectra/Por® (Spectrum Laboratories) 2 membrane (12-14 kDa-cutoff). The mixture was filtered through a 0.2 μm filter to remove precipitated materials and further dialyzed twice against 50% methanol followed by methanol. Some precipitate formed during the 50% methanol dialysis and redissolved during the methanol dialysis. The solution was concentrated to dryness to give the product (30.1 mg).

Example 43
Preparation of Fluorescein-Dendrimer-PEG Conjugates
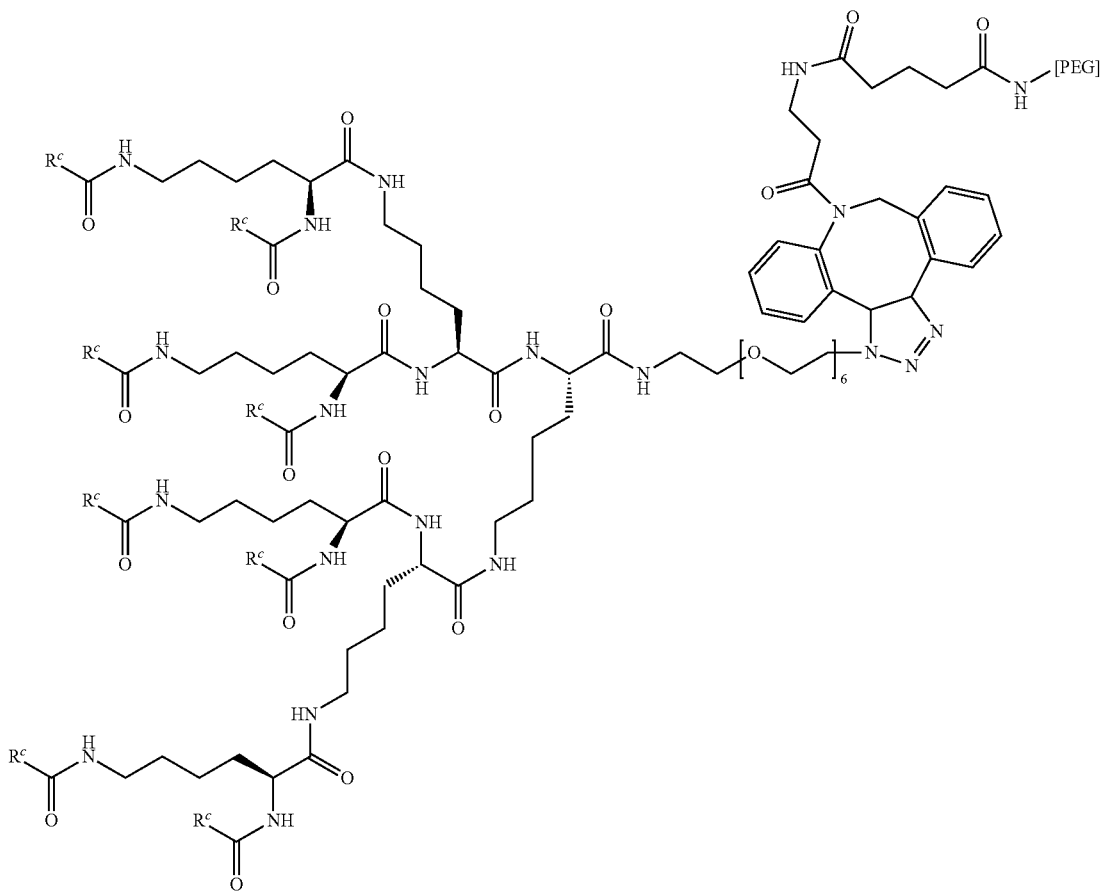
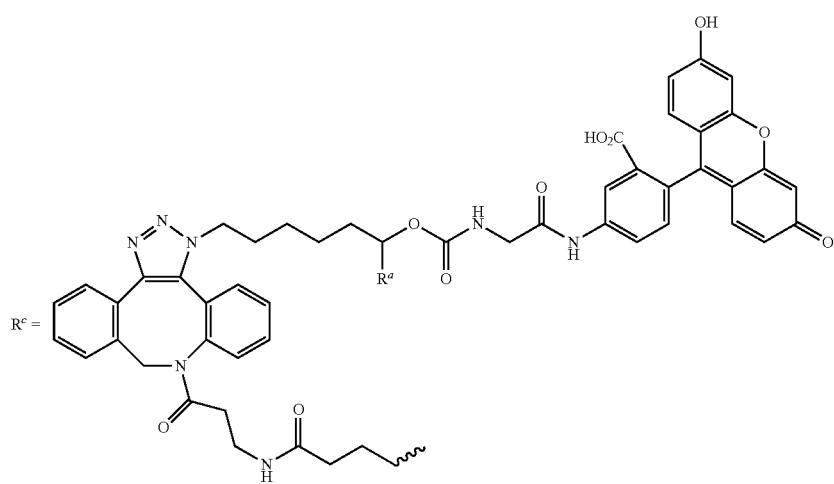

wherein $R^a$ is

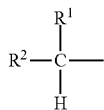

wherein $R^1$=phenyl-SO$_2$CH$_2$; $R^1$=(4-chlorophenyl)-SO$_2$CH$_2$, and $R^1$=morpholino-SO$_2$CH$_2$, and $R^2$ is H.

A mixture of acetic acid in methanol (5% v/v, 0.83 mL), a 0.81 mM methanol solution of [DBCO-Lys(DBCO)]$_4$[Lys]$_2$Lys-HEG-[mPEG$_{40kD}$] (Example 42, 0.170 mL, 0.17 mop, and a 11.7 mM solution of the linked fluorescein azide of Example 34 in DMSO (0.140 mL, 1.64 mol) was allowed to sit at ambient temperature for 70 h. The presence of excess azide was verified by size exclusion HPLC. The reaction mixture was dialyzed once against 50% methanol+0.5% v/v acetic acid using a Spectra/Por® (Spectrum Laboratories) 2 membrane (12-14 kDa-cutoff), then three times against methanol+0.2% v/v acetic acid. The dialysis mixture was concentrated to dryness to give the product as a dark orange-yellow solid.

Compounds prepared according to this method thus include PEGylated dendrimers wherein $R^a$ is

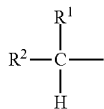

wherein $R^1$=phenyl-SO$_2$CH$_2$; $R^1$=(4-chlorophenyl)-SO$_2$CH$_2$, and $R^1$=morpholino-SO$_2$CH$_2$, and $R^2$ is H. Thus the product is of the formula

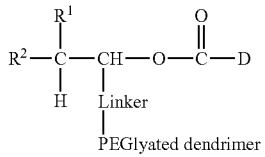

wherein D is modeled by fluorescein

Example 44

Fluorescein Release from Fluorescein-Dendrimer-PEG Conjugates

Figure 7:
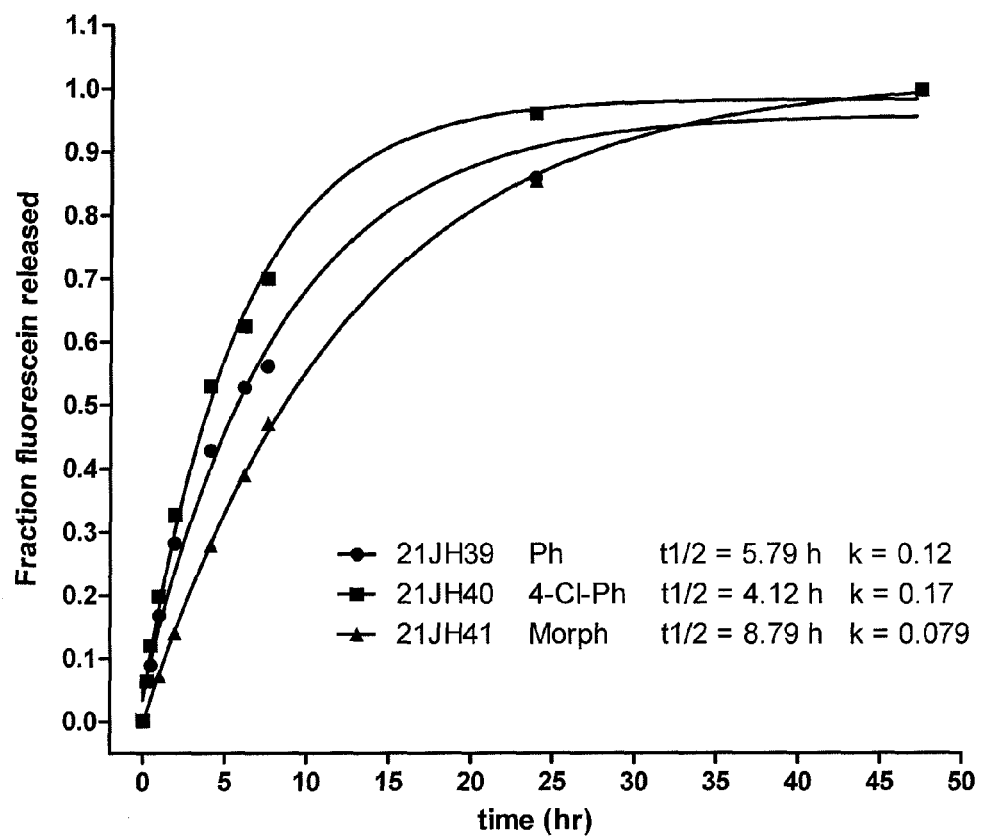
FIG. 7 shows the time course of release of fluorescein from PEGylated polylysine dendrimer.

The fluorescein-dendrimer-PEG conjugates of Example 43 were dissolved in 0.1 M bicine, pH 8.5, 37° C. to a concentration of ~20 µM total fluorescein. Aliquots were periodically removed and analyzed by HPLC to determine released 5-(aminoacetamido)fluorescein. Results are shown in FIG. 7.

Examples 45-46 Describe Synthesis of a More Complex Dendrimer

Example 45

Preparation of [Boc-Lys(Boc)]$_8$[Lys]$_4$[Lys]$_2$Lys-HEGA

To a suspension of [Lys]$_4$[Lys]$_2$Lys-HEGA (Example 40, 75 mg, 0.060 mmol) in 1:1 DMF:DMSO (12 mL) was added Et$_3$N (0.133 mL, 96.6 mg, 0.955 mmol) followed by Boc-Lys(Boc)-OPNP (270 mg, 0.578 mmol). The resulting mixture was allowed to stir for 25 h, during which time all of the starting material became soluble. Next 1 N NaOH (2 mL) was added to the reaction mixture for 3 h. The reaction mixture was then diluted with 200 mL of ethyl acetate, washed with 0.5 N NaOH (200 mL in small portions), then with 0.1 N HCl (200 mL in small portions), then with water, and finally brine. The extract was dried over MgSO$_4$ and concentrated to dryness to give the product (205 mg) as a white solid.

Example 46

Preparation of [Lys]$_8$[Lys]$_4$[Lys]$_2$Lys-HEGA

Trifluoroacetic acid (8 mL) was added to a solution of protected dendrimer [Boc-Lys(Boc)]$_8$[Lys]$_4$[Lys]$_2$Lys-HEGA (Example 45, 98 mg, 0.025 mmol) in DCM (8 mL). The resulting mixture was allowed to stir for 2 h at room temperature then concentrated under vacuum to give 360 mg of residue. The residue was dissolved in methanol (15 mL) and treated methanol-washed Dowex® (Dow Chemical Co.) Monosphere™ 550A (10 mL) for 20 minutes. The resin was removed by filtration and the filtrate concentrated to provide the product.

Examples 47-56 Describe Preparation of Fluorescein as Model Drug Coupled to PEGylated Dendrimers

Example 47

Preparation of N-(tert-butoxycarbonyl)-N'-(2,4-dinitrophenyl)-1,4-butanediamine

To a stirred solution of N-Boc-1,4-butanediamine (0.400 g; 2.12 mmol) and 1-fluoro-2,4-dinitrobenzene (280 µL; 2.23 mmol) in anhydrous tetrahydrofuran (THF) (10 mL) was added triethylamine (886 µL; 6.36 mmol). The reaction solution was stirred at ambient temperature for 17 hours and was then concentrated. The residue was dissolved in ethyl acetate and washed with water, saturated NaHCO$_3$ and saturated NaCl. The organic solution was dried over MgSO$_4$ and concentrated to give a yellow oil (1.12 g). Purification using a Thomson Instruments Single StEP™ silica gel column (25 g) and eluting with 20% ethylacetate/80% hexanes followed by 50% ethyl acetate/50% hexanes produced the product as a yellow oil (0.751 g, 100%). $^1$H NMR (d$_6$-DMSO) δ 1.36 (9H, s), 1.44 (2H, m) 1.58 (2H, m), 2.93 (2H, m), 3.46 (2H, m), 6.82 (1H, t, J=5.6 Hz), 7.23 (1H, d, J=9.5 Hz), 8.27 (1H, dd, J=2.7 Hz, J=9.6 Hz), 8.85 (2H, m).

Example 48

Preparation of Boc-Lys(Boc)-DAB-DNP

The Boc protected amine (0.751 g; 2.12 mmol) was dissolved in anhydrous dichloromethane (10 mL) and trifluoroacetic acid (10 mL) was added. The resulting solution was stirred at room temperature for 2 hours and was concentrated. Ethyl acetate was added and the mixture was concentrated. The brown solid thus obtained was dissolved in anhydrous N,N-dimethylformamide (DMF, 4 mL) and triethylamine (740 µL; 5.31 mmol) was added. To this solution was added a solution of Boc-Lys(Boc)-OPNP (1.19 g; 2.55 mmol) in anhydrous DMF (4 mL) and the solution stirred at room temperature for 18 hours. It was then poured into water (100 mL) and extracted with ethyl acetate (3×). The combined extracts were washed with water (2×) and saturated NaCl and were dried over MgSO$_4$ and concentrated to give an orange oil (2.00 g). Purification using a Thomson Instruments Single StEP™ silica gel column (25 g) and eluting with 50% ethylacetate/50% hexanes followed by 70% ethyl acetate/30% hexanes produced Boc-Lys(Boc)-DAB-DNP as a yellow solid (0.985 g, 79%). $^1$H NMR (DMSO) δ 1.34-1.61 (28H, m), 2.82 (2H, m), 3.07 (2H, m), 3.47 (2H, m), 3.77 (1H, m), 6.74 (2H, m), 7.23 (1H, d, J=9.7 Hz), 7.78 (1H, t, J=6.0 Hz), 8.24 (1H, dd, J=2.8 Hz, J=9.5 Hz), 8.85 (2H, m).

Example 49

Preparation of [Boc-Lys(Boc)]$_2$Lys-DAB-DNP

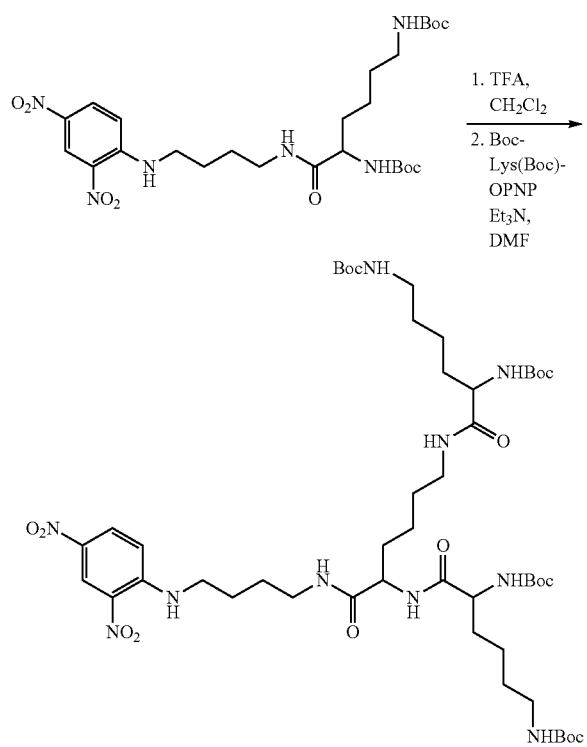

Boc-Lys(Boc)-DAB-DNP (0.500 g; 0.858 mmol) was dissolved in anhydrous dichloromethane (5 mL) and trifluoroacetic acid (5 mL) was added. The resulting solution was stirred at room temperature for 2 hours and was concentrated. Ethyl acetate was added and the mixture was concentrated. The brown oil thus obtained was dissolved in anhydrous DMF (5 mL) and triethylamine (598 μL; 4.29 mmol) added. To this solution was added a solution of Boc-Lys(Boc)-OPNP (0.963 g; 4.29 mmol) in anhydrous DMF (5 mL) and the solution stirred at room temperature for 18 hours. Additional triethylamine (188 μL; 1.35 mmol) was added and the reaction stirred for a further 3 hours. It was then slowly added to ice-water (250 mL) and extracted with ethyl acetate (3×). The combined extracts were washed with water (2×) and saturated NaCl and were dried over MgSO$_4$ and concentrated to give an orange oil (0.844 g). Purification using a Thomson Instruments Single StEP™ silica gel column (25 g) and eluting with 50% ethylacetate/50% hexanes followed by 100% ethyl acetate then 2% methanol/98% ethyl acetate and finally 5% methanol/95% ethyl acetate produced [Boc-Lys(Boc)]$_2$Lys-DAB-DNP as a yellow solid (0.367 g, 42%).

Example 50

Preparation of [Boc-Lys(Boc)]$_4$-[Lys]$_2$Lys-DAB-DNP

[Boc-Lys(Boc)]$_2$Lys-DAB-DNP (0.670 g; 0.645 mmol) was dissolved in anhydrous dichloromethane (7 mL) and trifluoroacetic acid (7 mL) added. The resulting solution was stirred at room temperature for 2 hours and was concentrated on the roto-vap. Ethyl acetate was added and the mixture was concentrated. The brown oil thus obtained was dissolved in anhydrous DMF (7 mL) and triethylamine (115 μL; 8.25 mmol) added. To this solution was added a solution of Boc-Lys(Boc)-OPNP (1.45 g; 3.10 mmol) in anhydrous DMF (7 mL). A further aliquot of triethylamine (400 μL; 2.87 mmol) was added and the solution stirred at room temperature for 18 hours, at which time HPLC analysis showed the reaction to be complete. The reaction mixture was added to water (160 mL) and extracted with ethyl acetate (3×). The combined extracts were washed with water (2×), 1M Na$_2$CO$_3$, and saturated NaCl and were dried over MgSO$_4$ and concentrated to give a yellow solid (1.68 g). Purification using a Thomson Instruments Single StEP™ silica gel column (40 g) and eluting 100% ethyl acetate then 5% methanol/95% ethyl acetate and finally 7.5% methanol/92.5% ethyl acetate produced [Boc-Lys(Boc)]$_4$[Lys]$_2$Lys-DAB-DNP as a yellow solid (0.600 g, 48%). $^1$H NMR (DMSO-d6) 1.15-1.59 (117H, m, Calc 118H), 2.73-2.98 (17H, m, Calc. 18H), 3.48 (2H, m), 3.81 (4H, m), 3.99 (3H, m), 6.66 (2H, d, J=8.2 Hz), 6.73 (4H, br. s), 6.89 (2H, d, J=7.0 Hz), 7.22 (1H, d, J=9.8 Hz), 7.65-7.7.95 (7H, m), 8.23 (1H, dd, J=2.7 Hz, J=9.5 Hz), 8.84 (2H, m). MS (ESI+) found 977.12 (M+2H)/2$^+$, data deconvoluted to give mw 1952.24; calc for C$_{92}$H$_{162}$N$_{18}$O$_{27}$ 1951.19.

Example 51

Preparation of [Lys]$_4$[Lys]$_2$Lys-DAB-DNP

A solution of [Boc-Lys(Boc)]$_4$[Lys]$_2$Lys-DAB-DNP (Example 50; 0.2 g, 0.1 mmol) in trifluoroacetic acid (2 mL) was stirred at room temperature for 6.5 hours. The solution was concentrated and then ethyl acetate was added and the solution, again, concentrated. The residue (0.505 g) was dissolved in methanol (15 mL) and methanol washed Dowex® (Dow Chemical Co.) 550A Monosphere™ resin (~10 mL) was added. The mixture was stirred gently for 1 hour and then filtered. The resin was washed with methanol and the filtrate concentrated to give [Lys]$_4$[Lys]$_2$Lys-DAB-DNP as a dark orange oil (0.092 g).

Example 52

Preparation of [Boc-Lys(Tfa)]$_8$[Lys]$_4$[Lys]$_2$Lys-DAB-DNP

A solution of Boc-Lys(Tfa)-OSu (0.366 g, 0.83 mmol) in DMF (1 mL) was added to a solution of [Lys]$_4$[Lys]$_2$Lys-DAB-DNP (Example 51; 0.10 g, 86.6 μmol) and triethylamine (97 μL, 696 μmol) in DMF (3 mL). The solution was stirred at ambient temperature for 1.5 hours and was added slowly to water (25 mL) with stirring. The solid was collected by filtration and washed with water and acetonitrile. The solid was re-suspended in acetonitrile and the mixture stirred for 1 hour. The solid was collected by filtration, washed with acetonitrile and dried to give the product as a yellow solid (0.161 g; 50%).

Example 53

Preparation of [Boc-Lys]$_8$[Lys]$_4$[Lys]$_2$Lys-DAB-DNP

The dendrimer [Boc-Lys(Tfa)]$_8$[Lys]$_4$[Lys]$_2$Lys-DAB-DNP (Example 52; 0.025 g; 6.67 µmol) was dissolved in methanol (1 mL) and 1 M sodium hydroxide (160 µL; 160 mmol) was added. The reaction was kept at 37° C. for 1.5 hours and was then diluted with water (2 mL). This solution was loaded onto a 1-g Bond-Elut™ (Varian) C$_{18}$ solid phase extraction column and the column was washed with water and water+0.1% TFA. The product was eluted with 1:1 water/acetonitrile+0.1% TFA and the product containing fractions pooled and diluted with methanol. This solution was treated with methanol-washed Dowex® (Dow Chemical Co.) 550A Monosphere™ resin for 1 h and was then filtered and concentrated to give the product as an orange glassy solid (0.022 g).

Example 54

Preparation of PEG-Coated Dendrimer [Boc-Lys(mPEG$_{5kD}$)]$_8$[Lys]$_4$[Lys]$_2$Lys-DAB-DNP A solution of [Boc-Lys]$_8$[Lys]$_4$[Lys]$_2$Lys-DAB-DNP (Example 53; 0.020 g; 7.4 µmol) and triethylamine (16.5 µL; 118 µmol) in N,N-dimethylformamide (1.5 mL) was treated with 5-kDa monomethoxy-polyethylene glycol succinimidyl carboxymethyl ester (JenKem technology, 0.591 g; 118 µmol) and the solution stirred at ambient temperature for 22 hours. The reaction mixture was diluted with water (10 mL) and dialysed (MWCO 12-14 kDa) against water (1 L) for 24 hours with a change of solvent after 6 hours. The water was replaced with methanol (1 L) and the dialysis continued for a further 6 hours. The retentate was concentrated and the crude product was taken up in tetrahydrofuran (2.5 mL). This solution was added slowly to a stirred solution of methyl tert-butyl ether (25 mL). After 1 hour the precipitated solid was collected by filtration, washed with methyl tert-butyl ether and dried to give the PEG-coated dendrimer as a yellow solid (0.463 g).

Example 55

Preparation of DBCO-Activated PEG-Coated Dendrimer

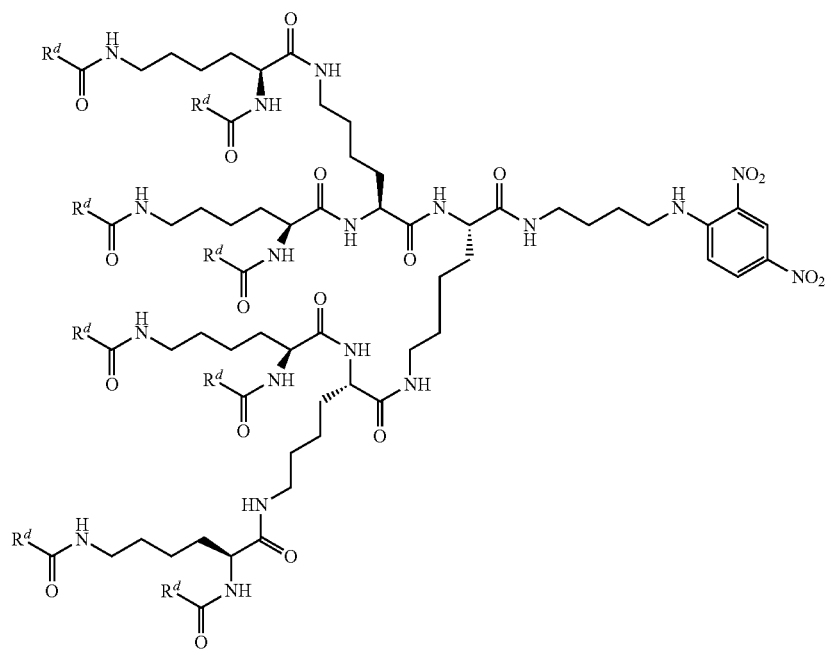

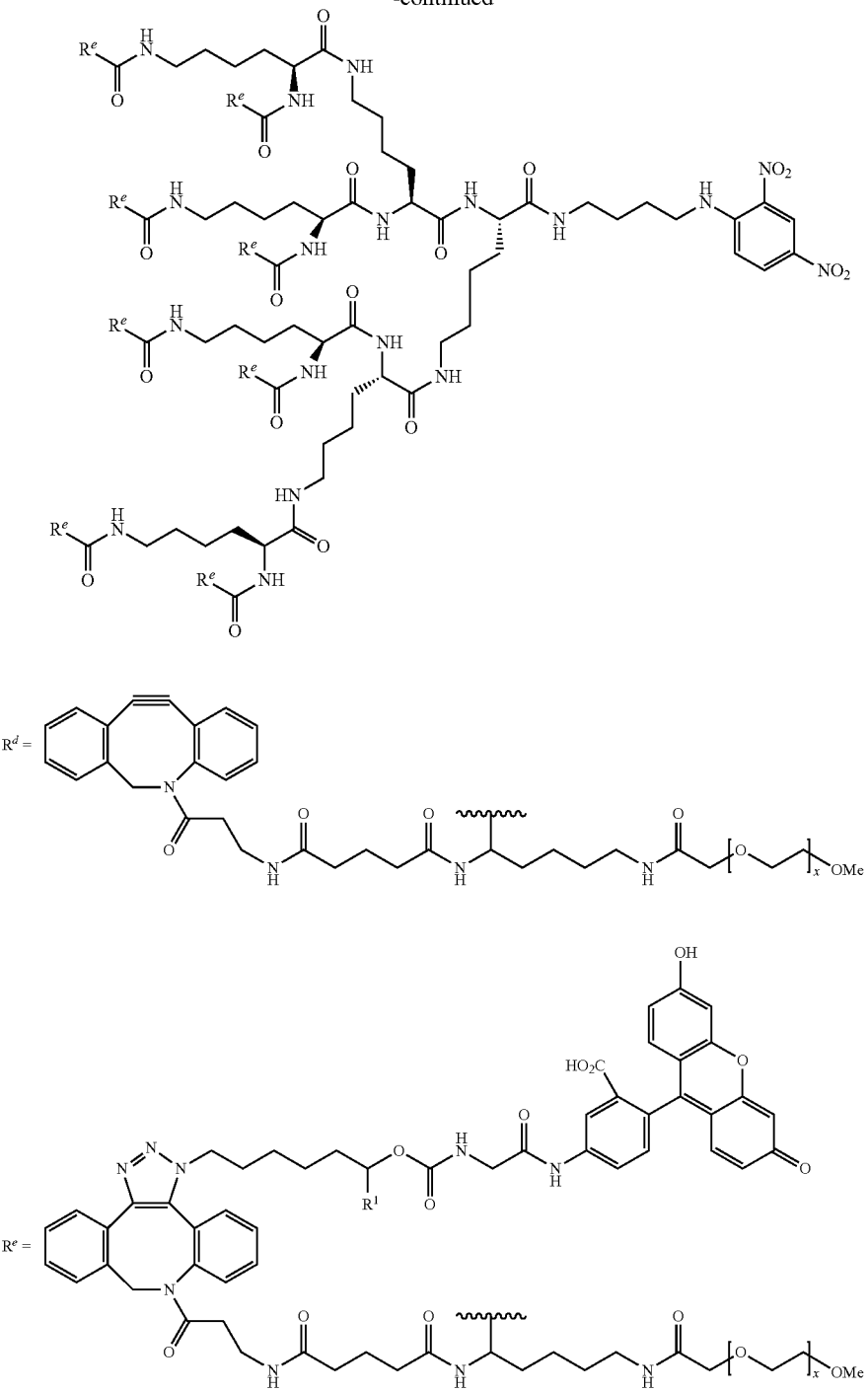

[DBCO-Lys(mPEG$_{5kD}$)]$_8$[Lys]$_4$[Lys]$_2$Lys-DAB-DNP

Trifluoroacetic acid (0.5 mL) was added to a solution of [Boc-Lys(mPEG$_{5kD}$)]$_8$-[Lys]$_4$[Lys]$_2$Lys-DAB-DNP (0.1 g) in 0.5 mL of dichloromethane. After 6 h, the mixture was concentrated to give a yellow oil (0.271 g). This was dissolved in methanol and treated with 10 mL of methanol-washed Dowex® (Dow Chemical Co.) 550A Monosphere™ resin for 1 h and was then filtered and concentrated to give the product as an pale yellow solid (68 mg). Analysis by UV absorbance indicated a total of 0.752 µmol of DNP.

To a stirred solution of DAB[DNP][Lys]$_8$[α-Boc]$_8$[ε-NHC(O)PEG$_{5K}$]$_8$ (0.752 µmol) in acetonitrile (1 mL) was added triethylamine (2 µL; 14.7 µmol) and DBCO—NHS (0.006 g; 12.5 µmol) and the solution stirred at ambient temperature for 6.5 hours. To the reaction solution was then added 10 mL of 10 mM taurine in HEPES pH 7.0 and the solution stirred for 17 hours. This solution was dialysed (MWCO 12-14K) against water (1 L) for 7.5 hours with a change of solvent after 4.5 hours. The water was replaced with methanol (1 L) and the dialysis continued for 17 hours. The retentate was concentrated and the crude product was taken up in tetrahydrofuran (1.5 mL) and slowly added to a stirred solution of methyl t-butyl ether (15 mL). After 1 hour the solid was collected, washed with methyl t-butyl ether and dried to give the product (0.057 g) as a pale yellow solid.

Example 56

Preparation of Fluorescein-Conjugated to PEG-Coated Dendrimer

To 500 μL of a 0.2 mM solution of [DBCO-Lys (mPEG$_{5kD}$)]$_8$[Lys]$_4$[Lys]$_2$Lys-DAB-DNP in tetrahydrofuran was added 103 μL of the 11.7 mM linked fluorescein azide solution in DMSO prepared in Example 34. The reaction solution was incubated in the dark for 17 hours at which time HPLC analysis indicated complete consumption of the fluorescein azide. A further 50 μL aliquot of the linked fluorescein azide was added and the reaction incubated in the dark for 24 hours. HPLC analysis now showed residual fluorescein azide. The reaction solution was diluted with water (2 mL) and was

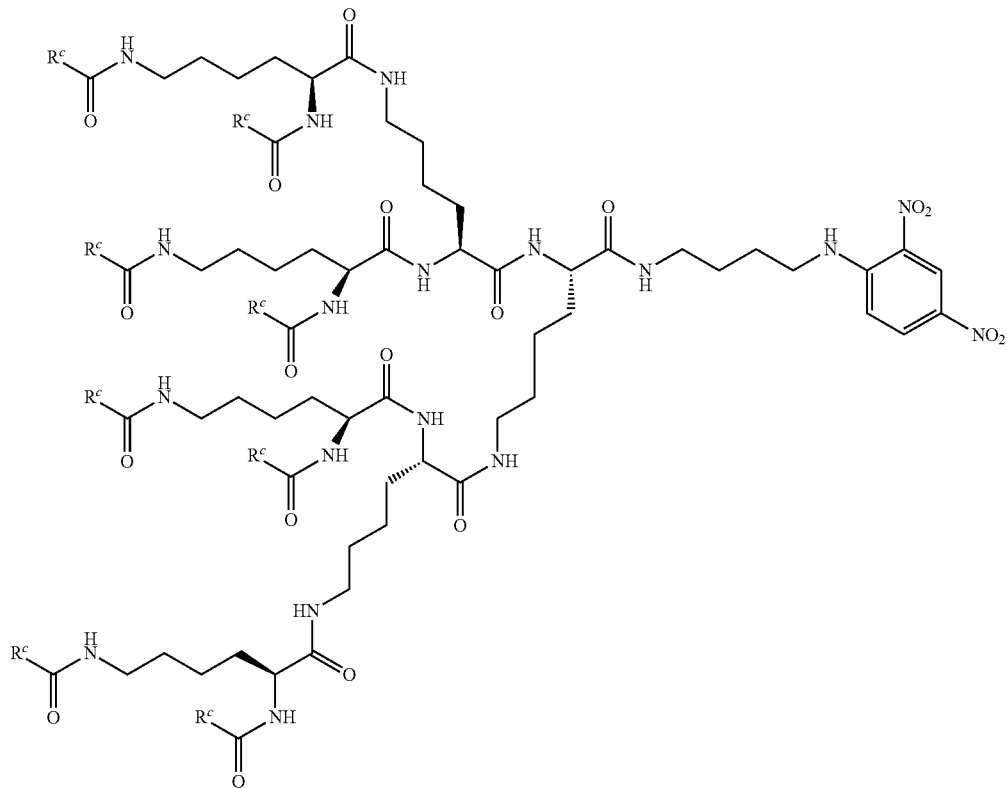

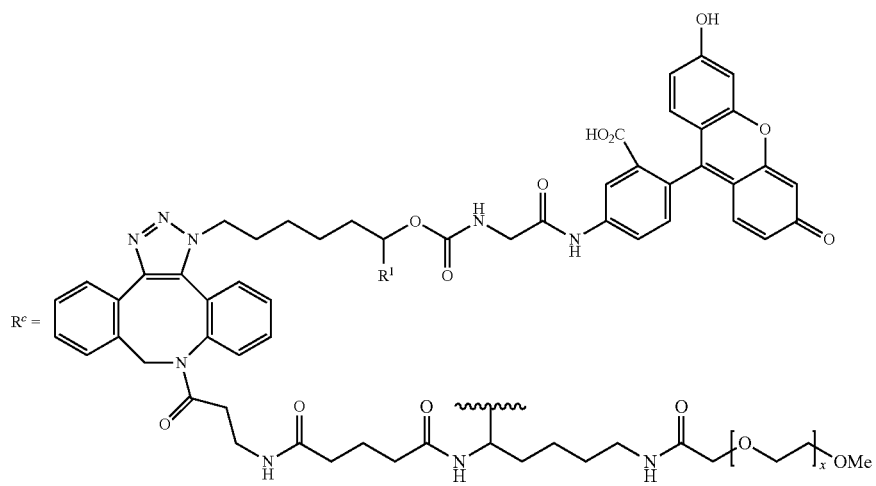

dialysed (MWCO 12-14K) against 10 mM sodium acetate, pH 5, (250 mL) for 22 hours in the dark. The buffer was replaced with methanol (250 mL) and the dialysis continued for 7 hours with a change of solvent after 4 hours. The retentate was concentrated on the roto-vap. Compounds include those wherein $R^1$ is phenylsulfonyl, 4-chlorophenylsulfonyl and morpholinosulfonyl.

Example 57

Release of Fluorescein from PEG-Coated Dendrimer Conjugates

Figure 8:
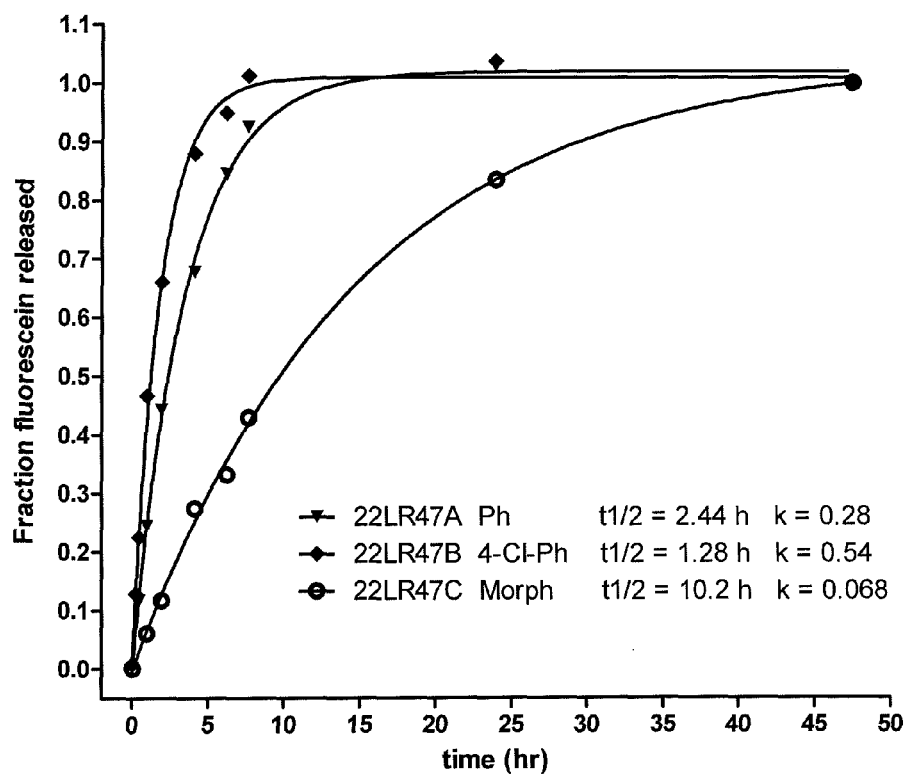
FIG. 8 shows the kinetics of release of fluorescein from coupling to a PEG-coated polylysine dendrimer.

The fluorescein-dendrimer-PEG conjugates of Example 56 were dissolved in 0.1 M bicine, pH 8.5, 37° C. to a concentration of ~20 μM total fluorescein. Aliquots were periodically removed and analyzed by HPLC to determine released 5-(aminoacetamido)fluorescein. Results are shown in FIG. 8.

Example 58

Preparation of mPEG$_{40kD}$-DBCO

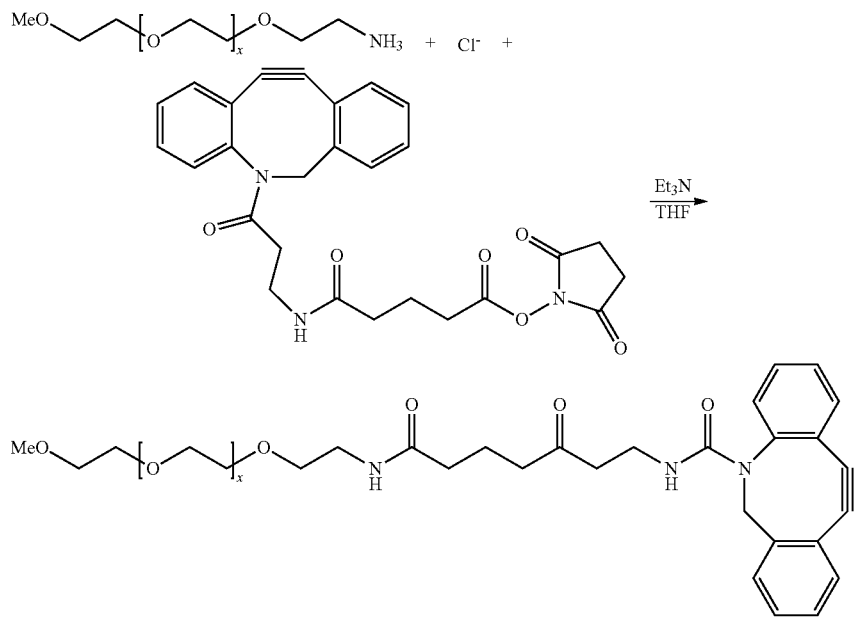

A solution of 40-kDa monomethoxy polyethylene glycol amine hydrochloride (JenKem Technology, 2 g, 50 μmol), triethylamine (20 μL), and 6-aza-5,9-dioxo-9-(1,2-didehydrodibenzo[b,f]azocin-5(6H)-yl)nonanoic acid succinimidyl ester ("DBCO—NHS", Click Chemistry Tools, Macon, Ga.) (50 mg, 100 μmol) in 25 mL of THF was stirred for 24 h at ambient temperature. The product was precipitated by addition of the reaction mixture to 100 mL of methyl tert-butyl ether (MTBE). The precipitate was collected by vacuum filtration, then redissolved in THF and the precipitation in MTBE was repeated to provide 1.98 g of product free of residual DBCO—NHS as determined by HPLC analysis.

Example 59

Kinetics of Release

Rates of release of the drug from the conjugates of the invention can readily be determined by methods known in the art including chromatographic methods, such as HPLC. Where, for example, a fluorescent marker is used as a model system for the drug, the fluorescence attributable to freed fluorescent compound is readily determined as compared to fluorescence emitted by the conjugate.

The in vivo release of drug from the conjugates of the invention may be measured by determining the pharmacokinetics of the conjugates as compared with the pharmacokinetics of a non-releasable conjugate of the same size. Such data are preferably obtained in rats as compared to mice as they exhibit more favorable clearance rates for the high molecular weight conjugates of the invention.

Figure 9A:
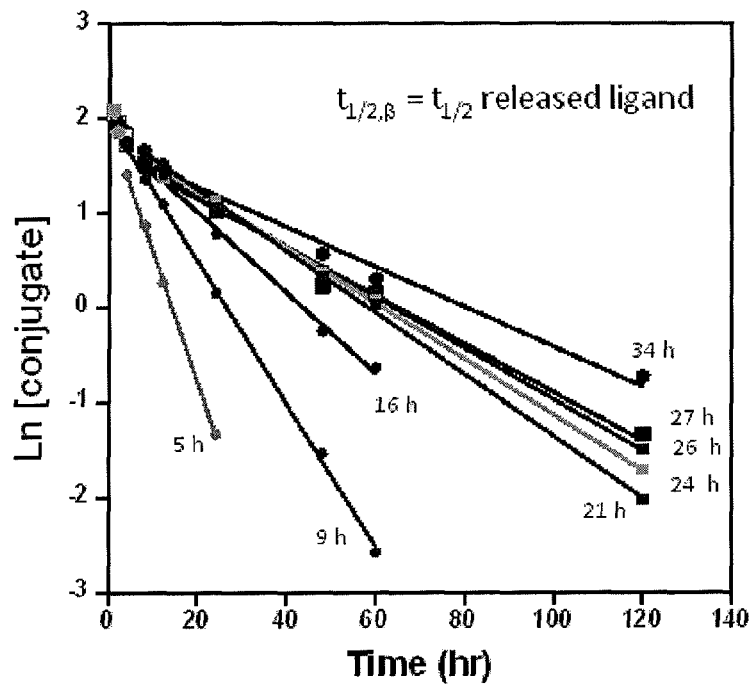
FIGS. 9a and 9b show, respectively, raw data showing concentration of various conjugates in plasma in a rat model system and the calculated release rate of the drug from the conjugate depending on the nature of the trigger. These data demonstrate the control over drug release rates using beta-elimination linkers.
Figure 9B:
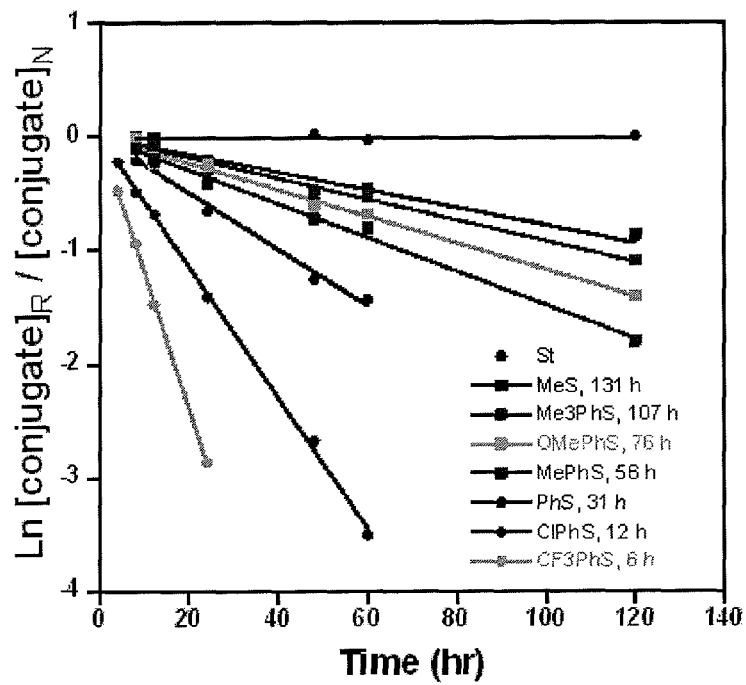

In more detail, the conjugates are administered to a model subject such as a rat, for example, by intravenous administration, and blood samples are periodically taken and plasma isolated. The level of conjugate in the plasma as a function of time is then determined. This may be done by chromatographic separation (for example, HPLC analysis after deproteinization coupled to UV, fluorescence, or mass spectrometric detection), or in appropriate cases by a direct assay such as ELISA, bioactivity, or fluorescence. As noted above, macromolecular conjugates adhere to a one-compartment model, conjugates of the invention can disappear from the plasma by one of two mechanisms: release of drug from the conjugate, and clearance of the intact conjugate (e.g., by renal filtration). The rate of loss of a releasable conjugate from the plasma is thus the sum of the rates of loss by release of the drug and by clearance of the conjugate. In contrast, the rate of loss of a non-releasable conjugate is just the rate of clearance of the conjugate from the plasma, since no drug is released. Thus, the rate of drug release from a conjugate of the invention can be calculated as the difference in rates of loss of the releasable conjugate from that of a corresponding non-releasable conjugate. This may be done by directly taking the difference in rates or this can be calculated from the slope of a plot of ln (R/N) versus time, where R is the concentration of releasable conjugate and N is the concentration of non-releasable conjugate, as shown in FIGS. 9a and 9b. As shown in panel a, the raw data simply show the logarithm (ln) of the concentration of various conjugates and of a stable conjugate as a function of time. Panel b shows the difference in release rates of various releasable conjugates which are obtained by the calculation described above. The stable conjugate, of course, shows zero release rate whereas release rates of drug from various embodiments of the trigger for release in sample conjugates are shown.

Figure 10:
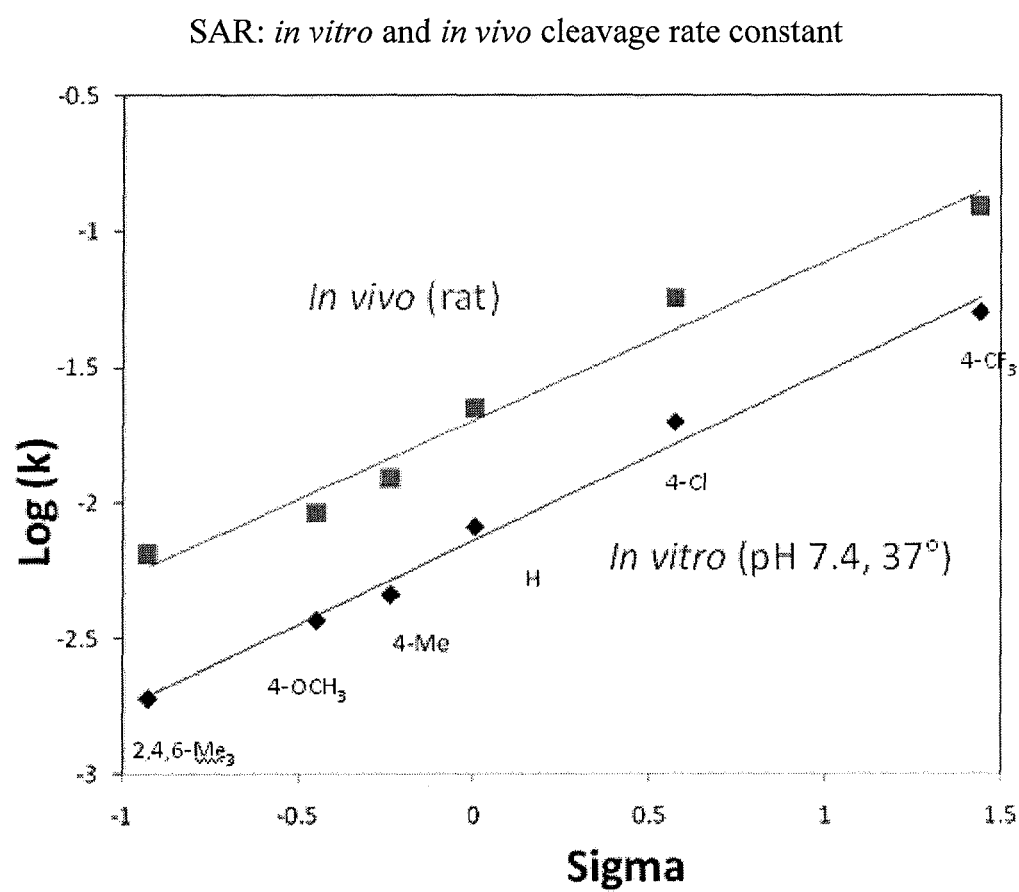
FIG. 10 shows a comparison of in vivo and in vitro release rates of drugs as a function of the Hammett constants associated with the trigger.

FIG. 10 shows that the variation of the rate constant as a function of the nature of the trigger in vitro and in vivo follow the same pattern which correlates as expected with the Hammett constants associated with the trigger.

The invention claimed is:

1. A dendrimer coupled to a multiplicity of substituents of the formula

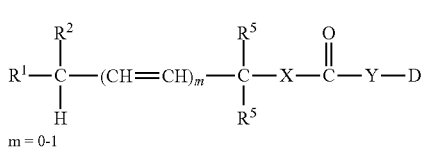

(2)

$m = 0\text{-}1$ at least one or both $R^1$ and $R^2$ is independently CN; $NO_2$;
  optionally substituted aryl;
  optionally substituted heteroaryl;
  optionally substituted alkenyl;
  optionally substituted alkynyl;
  $COR^3$ or $SOR^3$ or $SO_2R^3$ wherein
    $R^3$ is H or optionally substituted alkyl;
    aryl or arylalkyl, each optionally substituted;
    heteroaryl or heteroarylalkyl, each optionally substituted; or
    OR or $NR_2$ wherein each R is independently H or optionally substituted alkyl;
  $SR^4$ wherein
    $R^4$ is optionally substituted alkyl;
    aryl or arylalkyl, each optionally substituted; or
    heteroaryl or heteroarylalkyl, each optionally substituted;
wherein $R^1$ and $R^2$ may be joined to form a 3-8 member ring; and
wherein one and only one of $R^1$ and $R^2$ may be H or may be alkyl, arylalkyl or heteroarylalkyl, each optionally substituted;
each $R^5$ is independently H or is alkyl, alkenylalkyl, alkynylalkyl, aryl, arylalkyl, heteroaryl or heteroarylalkyl, each optionally substituted;
D is a residue of a drug or prodrug coupled through O, S, or N;
Y is absent and X is O or S; or
Y is $NBCH_2$ and X is O;
wherein B is alkyl, aryl, arylalkyl, heteroaryl or heteroarylalkyl, each optionally substituted; and
wherein said coupling to the dendrimer is through any of $R^1$, $R^2$, $R^5$ or B.

2. The dendrimer of claim 1 wherein when X is O or S and Y is absent said dendrimer is coupled to $R^1$, $R^2$, $R^5$ or B through one or more connecter residues.

3. The dendrimer of claim 1 wherein said dendrimer has a minimum G of 3 wherein G is the number of generations included in the dendrimer where the core of the dendrimer is assigned G=0.

4. The dendrimer of claim 1 wherein the dendrimer is poly L-lysine (PLL) or polyamidoamine (PAMAM).

5. The dendrimer of claim 1 which further comprises a multiplicity of coupled inert protective polymers.

6. The dendrimer of claim 5 wherein the protective polymer is polyethylene glycol (PEG).

7. The dendrimer of claim 1 wherein the drug is a peptide, a nucleic acid or a small molecule.

8. The dendrimer of claim 1 wherein one of $R^1$ and $R^2$ is CN, or
  wherein at least of one $R^1$ and $R^2$ comprises phenyl or phenylene.

9. The dendrimer of claim 1 wherein one of $R^1$ and $R^2$ is $SO_2R^3$ and the other is H.

10. The dendrimer of claim 1 wherein m is 0.

11. A dendrimer coupled to a multiplicity of substituents of the formula

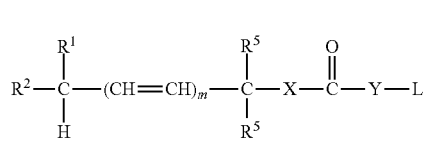

(3)

$m = 0\text{-}1$ at least one, or both $R^1$ and $R^2$ is independently CN; $NO_2$;
  optionally substituted aryl;
  optionally substituted heteroaryl;
  optionally substituted alkenyl;
  optionally substituted alkynyl;
  $COR^3$ or $SOR^3$ or $SO_2R^3$ wherein
    $R^3$ is H or optionally substituted alkyl;
    aryl or arylalkyl, each optionally substituted;
    heteroaryl or heteroarylalkyl, each optionally substituted; or
    OR or $NR_2$ wherein each R is independently H or optionally substituted alkyl;
  $SR^4$ wherein
    $R^4$ is optionally substituted alkyl;
    aryl or arylalkyl, each optionally substituted; or
    heteroaryl or heteroarylalkyl, each optionally substituted;
wherein $R^1$ and $R^2$ may be joined to form a 3-8 member ring; and
wherein one and only one of $R^1$ and $R^2$ may be H or may be alkyl, arylalkyl or heteroarylalkyl, each optionally substituted;
each $R^5$ is independently H or is alkyl, alkenylalkyl, alkynylalkyl, aryl, arylalkyl, heteroaryl or heteroarylalkyl, each optionally substituted;
Y is absent and X is O or S; or
Y is $NBCH_2$ and X is O;
wherein B is alkyl, aryl, arylalkyl, heteroaryl or heteroarylalkyl, each optionally substituted; and
L is a nucleofuge,
wherein said coupling to the dendrimer is through any of $R^1$, $R^2$, $R^5$ or B.

12. The dendrimer of claim 11 wherein when X is O or S and Y is absent said dendrimer is coupled to $R^1$, $R^2$, $R^5$ or B through one or more connecter residues.

13. The dendrimer of claim 11 wherein when X is O or S and Y is absent said dendrimer has a minimum G of 3 wherein G is the number of generations included in the dendrimer where the core of the dendrimer is assigned G=0.

14. The dendrimer of claim 11 wherein the dendrimer is poly L-lysine (PLL) or polyamidoamine (PAMAM).

15. The dendrimer of claim 1 which is further coupled to at least one protective inert polymer.

16. The dendrimer of claim 15 wherein the protective polymer is polyethylene glycol (PEG).

17. A method to prepare the dendrimer of claim 1 which method comprises (a) reacting a compound of the formula

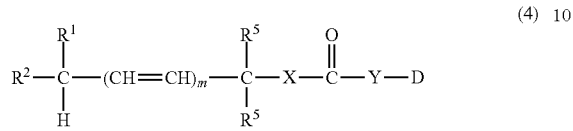
(4)

wherein m, $R^1$, $R^2$, $R^5$, X, Y, m and D are as defined in claim 1; and wherein one of $R^1$, $R^2$, $R^5$ and B comprises a functional group or connecter that couples formula (4) to a dendrimer with a dendrimer under conditions whereby said dendrimer is coupled to said compound, or (b) reacting the dendrimer of claim 11 with a drug or prodrug under conditions whereby said drug or prodrug is coupled to said dendrimer.

18. A compound of the formula $M\text{-}(J\text{-}D)_m$ wherein M is a dendrimer, D is a drug and J is a joining moiety that releases D by a beta elimination mechanism, wherein m is an integer of at least 8.

* * * * *